US010624947B2

(12) United States Patent
Kao et al.

(10) Patent No.: US 10,624,947 B2
(45) Date of Patent: Apr. 21, 2020

(54) BACTERICIDAL PEPTIDES AND USES THEREOF

(71) Applicant: INDIANA UNIVERSITY RESEARCH AND TECHNOLOGY CORPORATION, Indianapolis, IN (US)

(72) Inventors: C. Cheng Kao, Bloomington, IN (US); Dean Rowe-Magnus, Bloomington, IN (US); Antonio Cembellin Prieto, Bloomington, IN (US)

(73) Assignee: Indiana University Research and Technology Corporation, Indianapolis, IN (US)

( * ) Notice: Subject to any disclaimer, the term of this patent is extended or adjusted under 35 U.S.C. 154(b) by 0 days.

(21) Appl. No.: 16/146,165

(22) Filed: Sep. 28, 2018

(65) Prior Publication Data

US 2019/0054140 A1 Feb. 21, 2019

Related U.S. Application Data

(63) Continuation-in-part of application No. PCT/US2017/024766, filed on Mar. 29, 2017.

(60) Provisional application No. 62/657,222, filed on Apr. 13, 2018, provisional application No. 62/314,608, filed on Mar. 29, 2016.

(51) Int. Cl.
*A61K 38/17* (2006.01)
*A61P 31/04* (2006.01)

(52) U.S. Cl.
CPC .............. *A61K 38/17* (2013.01); *A61P 31/04* (2018.01)

(58) Field of Classification Search
None
See application file for complete search history.

(56) References Cited

U.S. PATENT DOCUMENTS

| | | | |
|---|---|---|---|
| 10,138,282 B2 | 11/2018 | Kao et al. | |
| 2004/0170642 A1 | 9/2004 | Fritz et al. | |
| 2005/0058689 A1 | 3/2005 | McDaniel | |
| 2010/0239611 A1 | 9/2010 | Van Drunen Littel et al. | |
| 2010/0316643 A1 | 12/2010 | Eckert et al. | |
| 2011/0250626 A1 | 10/2011 | Williams et al. | |
| 2013/0252880 A1* | 9/2013 | Kallenbach | A61K 38/10 514/2.4 |
| 2014/0296137 A1 | 10/2014 | Rajamani et al. | |

FOREIGN PATENT DOCUMENTS

WO  WO2010-013039  *  1/2010

OTHER PUBLICATIONS

UniProt sequence P54228 (CTHL6_BOVIN)(<https://www.uniprot.org/uniprot/P54228>Oct. 1, 1996).*
GenBank sequence AKA21233.1 (<https://www.ncbi.nlm.nih.gov/protein/aka21233>May 10, 2014).*
LifeTein (https://www.lifetein.com/Peptide-Synthesis-Amidation-Acetylation.html ;Aug. 7, 2014).*
International Search Report and Written Opinion of PCT/US17/24766, dated Sep. 5, 2017.
Hoiby et al., "Antiobiotic resistance of bacterial biofilms," International Journal of Antimicrobial Agents, 35 92010), 322-332.
Kao et al., "Cathelicidin Antimicrobial Peptides with Reduced Activation of Toll-Like Receptor Signaling Have Potent Bactericidal Activity against Colistin-Resistant Bacteria," Antimicrobial Peptides, Sep./Oct. 2016, vol. 7, Issue 5, 1-5.
Li et al., "In Vitro Susceptibility of Characterized B-Lactamase-Producing Strains Tested with Avibactam Combinations," Antimicrobial Agents and Chemotherapy, Mar. 2015, vol. 59, No. 3, 1789-1793.
Liu et al., "Emergence of plasmid-mediated colistin resistance mechanism MCR-1 in animals and human beings in China: a microbial and molecular biological study," www.thelancet.com/infection vol. 16, Feb. 2016, 161-168.
"M100-S25 Performance Standards for Antimicrobial Susceptibility Testing; Twenty-Fifth Information Supplement," Clinical and Laboratory Standards Institute, vol. 35, No. 3, 3 pages.
Mediavilla et al., "Colistin- and Carbapenem-Resistant *Escherichia coli* Harboring mcr-1 and blaNDM-5, Causing a Complicated Urinary Tract Infection in a Patient from the United States," American Society for Microbiology, Jul./Aug. 2016, vol. 7, Issue 4, 4 pages.
Nguyen et al., "The expanding scope of antimicrobial peptide structures and their modes of action," Trends in Biotechnology, Sep. 2011, vol. 29, No. 9, 464-472.
Rhouma et al., "Colistin in Pig Production: Chemistry, Mechanism of Antibacterial Action, Microbial Resistance Emergence, and One Health Perspective," Frontiers in Microbiology, Nov. 2016, vol. 7, Article 1789. 22 pages.
Sanchez et al., "Klebsiella pneumoniae Antimicrobial Drug Resistance, United Staets, 1998-2010," Emerging Infectious Diseases, vol. 19, No. 1, Jan. 2013, 133-136.
Starks et al., "Pathogenesis of Infection by Clinical and Environmental Strains of Vibrio vulnificus in Iron-Dextran-Treated Mice," Infection and Immunity, Oct. 2000, vol. 68, No. 10, 5785-2793.
Wang, G., "Structures of Human Host Defense Cathelicidin LL-37 and Its Smallest Antimicrobial Peptide KR-12 in Lipid Micelles," The Journal of Biological chemistry, vol. 283, No. 47, 32637-32643.
Wright et al, "Role of Iron in the Pathogenesis of Vibrio vulnificus Infections," Infection and Immunity, Nov. 1981, vol. 34, No. 2, 503-507.
Zanetti, M., "Cathelicidins, multifunctional peptides of the innate immunity," Journal of Leukocyte Biology, vol. 75, Jan. 2004, 39-48.
Zasloff, M., "Defending the epithelium," Nature Medicine, vol. 12, No. 6, Jun. 2006, 607-608.

(Continued)

*Primary Examiner* — James H Alstrum-Acevedo
*Assistant Examiner* — Tara L Martinez
(74) *Attorney, Agent, or Firm* — Barnes & Thornburg LLP

(57) ABSTRACT

Antimicrobial compositions having bactericidal activity are described. Also described is a method of treating bacterial infections using compositions comprising antimicrobial peptides or variants thereof.

20 Claims, 23 Drawing Sheets

Specification includes a Sequence Listing.

(56) References Cited

OTHER PUBLICATIONS

Acosta-Smith et al., "Bovine Lactoferrin and Lactoferrin-Derived Peptides Inhibit the Growth of Vibrio cholera and Other Vibrio species," Front Microbial, 2018, 8, 2633, pp. 1-14.
International Search Report and Written Opinion of the International Searching Authority for the International Application No. PCT/US19/27454, dated Aug. 26, 2019, 18 pgs.

* cited by examiner

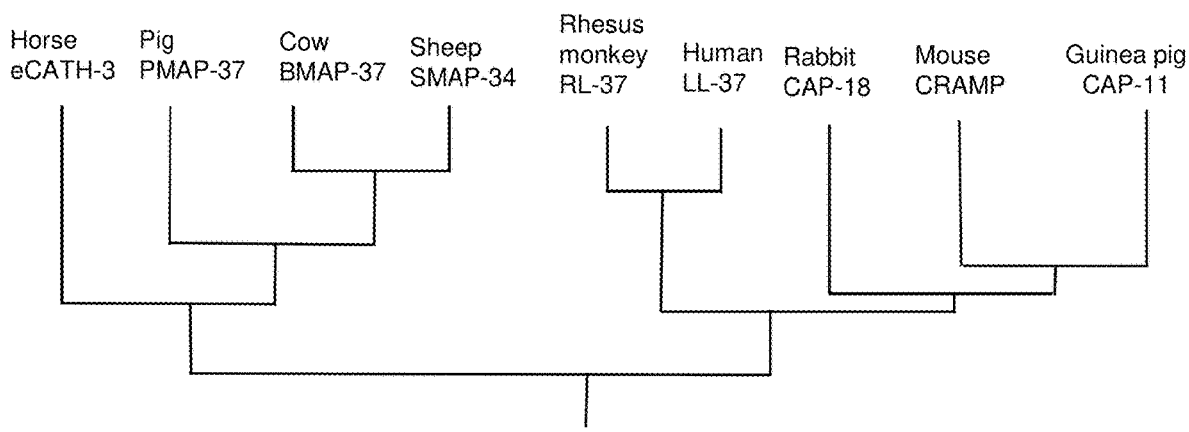

FIG. 3A

| Peptide | #AAs | Sequence |
|---------|------|----------|
| LL-37 | 37 | LLGDFFRKSKEKIGKEFKRIVQRIKDFLRNLVPRTES |
| RL-37 | 37 | RLGNFFRKVKEKIGGGLKKVGQKIKDFLGNLVPRTAS |
| CAP-18 | 37 | GLRKRLRKFRNKIKEKLKKIGQKIQGLLPKLAPRTDY |
| CRAMP | 34 | GLLRKGGEKIGEKLKKIGQKIKNFFQKLVPQPEQ |
| CAP-11 | 43 | GLRKKFRKTRKRIQKLGRKIGKTGRKVWKAWREYGQIPYPCRI |
| SMAP-34 | 34 | GLFGRLRDSLQRGGQKILEKAERIWCKIKDIFR |
| BMAP-34 | 34 | GLFRRLRDSIRRGQQKILEKARRIGERIKDIFRG |
| PMAP-37 | 37 | GLLSRLRDFLSDRGRRLGEKIERIGQKIKDLSEFFQS |
| eCATH-3 | 40 | KRFHSVGSLIQRHQQMIRDKSEATRHGIRIITRPKLLLAS |

Jpred 4 prediction

FIG. 3B

|         |                                           | # strains inhibited |      |       |       |      |       |
|---------|-------------------------------------------|---------------------|------|-------|-------|------|-------|
| Peptide | Sequence                                  | K.p.                | S.m. | E.cl. | E.co  | P.a. | Total |
| SMAP-29  | RGLRRLGRKIAHGVKKYGPTVLRIIRIAG | 4/4 | 1/3 | 2/2 | 5/6 | 4/4 | 16/19 |
| SMAP-29B | RGLRRLGRKIAHGVKKCGPTVLRIIRIAG | 4/4 | 1/3 | 2/2 | 5/6 | 4/4 | 16/19 |
| SMAP-29D | RGLRRLGRKIAHGVKKLGPTVLRIIRIAG | 4/4 | 1/3 | 2/2 | 5/6 | 4/4 | 16/19 |
FIG. 4A
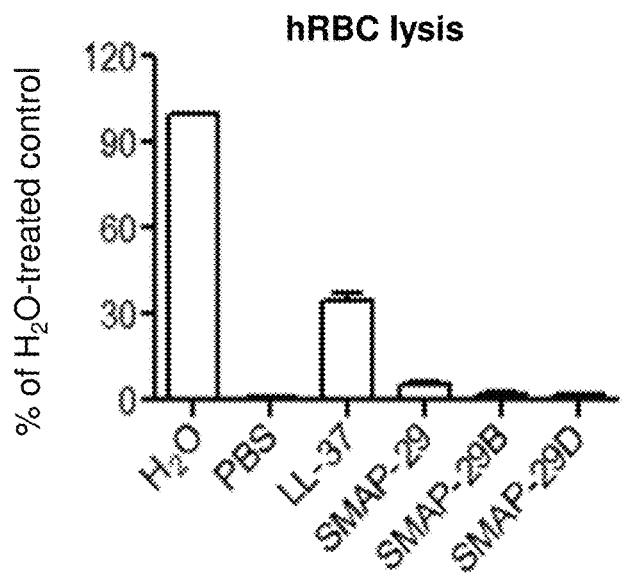
FIG. 4B
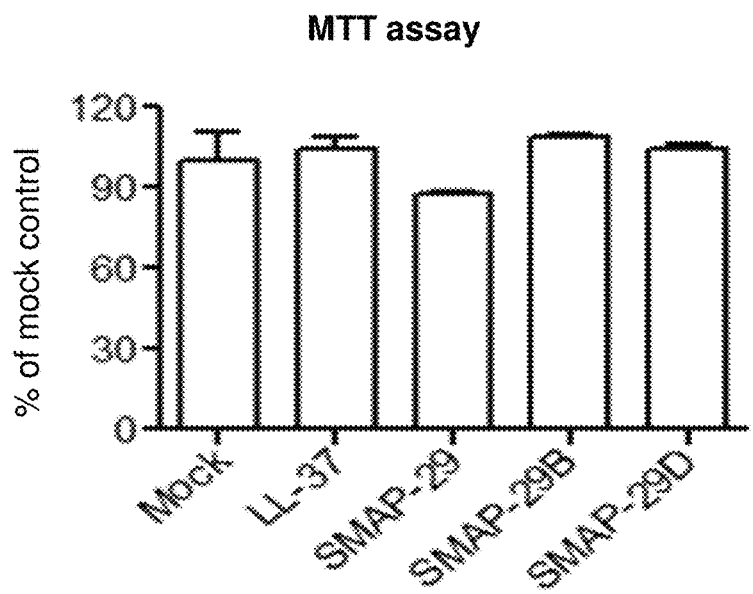
FIG. 4C

|          |                              |      |      | # strains inhibited | | | |
| Peptide  | Sequence                     | K.p. | S.m. | E.cl. | E.co | P.a. | Total |
|----------|------------------------------|------|------|-------|------|------|-------|
| BMAP-27  | GRFKRFRKKFKKLFKKLSPVIPLLHLG  | 4/4  | 3/3  | 2/2   | 6/6  | 4/4  | 19/19 |
| BMAP-27A | GRFKRLRKKFKKLFKKLSPVIPLLHLG  | 4/4  | 3/3  | 2/2   | 6/6  | 4/4  | 19/19 |
| BMAP-27B | GRFKRLRKKLKKLFKKLSPVIPLLHLG  | 4/4  | 3/3  | 2/2   | 6/6  | 4/4  | 19/19 |
| BMAP-27C | GRAKRLRKKLKKLAKKLSPVIPLLHLG  | 4/4  | 2/3  | 2/2   | 6/6  | 4/4  | 17/19 |
FIG. 5A
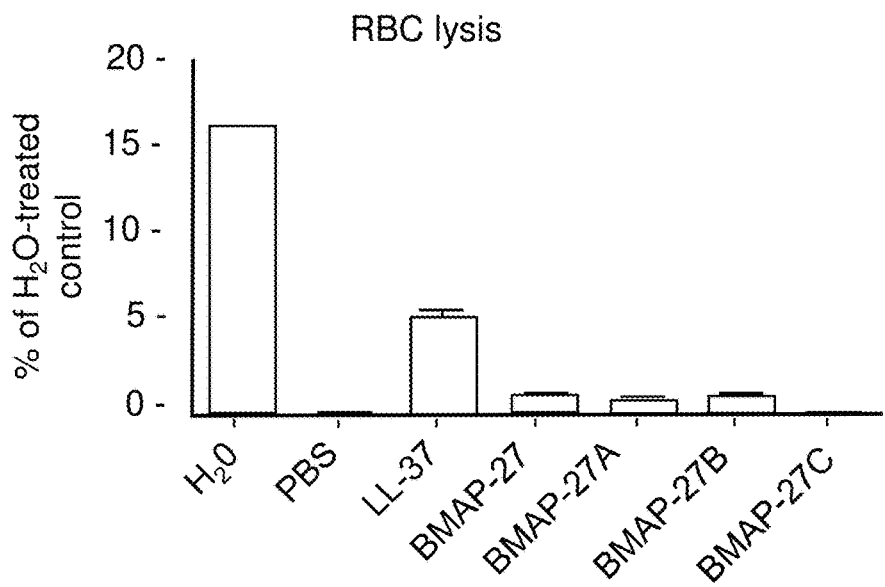
FIG. 5B
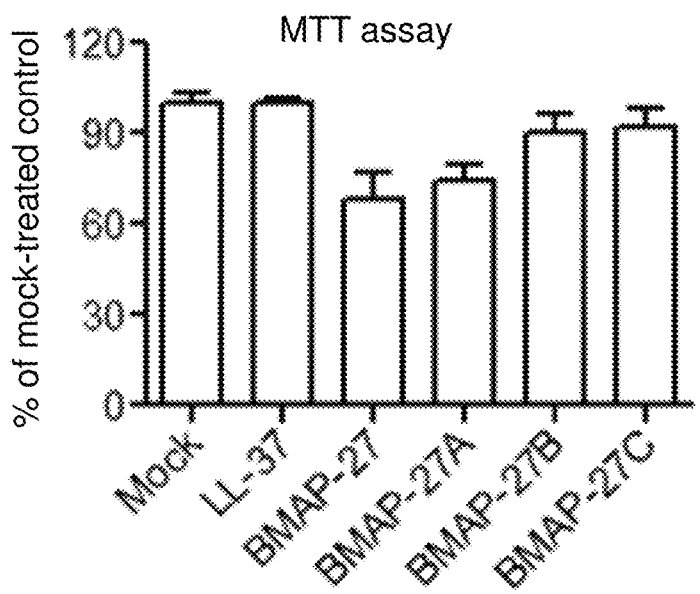
FIG. 5C

| Time (min) | | 0 | 5 | | 30 | 180 |
|---|---|---|---|---|---|---|
| | | CFU/ml (SD) | CFU/ml (SD) | Fold reduction from T₀ | CFU/ml (SD) | CFU/ml (SD) |
| SMAP-29D (2 µM) | | | | | | |
| Species | E. cloacae 4080 | 2.4 x 10⁶ (2.3 x 10⁵) | 2.9 x 10⁴ (5.9 x 10³) | 87 | 5.3 x 10² (4.1 x 10²) | < 40 |
| | E. coli IU342 | 1.0 x 10⁶ (1.1 x 10⁵) | 6.4 x 10³ (8.5 x 10²) | 156 | 3.3 x 10² (1.4 x 10²) | < 40 |
| | K. pneumoniae 8893 | 1.1 x 10⁶ (2.8 x 10⁵) | 9.4 x 10³ (9.9 x 10²) | 117 | 3.5 x 10² (7.0 x 10¹) | < 40 |
| | K. pneumoniae C-2 | 0.96 x 10⁶ (9.6 x 10⁴) | 1.7 x 10⁴ (2.1 x 10³) | 56 | 1.2 x 10³ (7.0 x 10²) | < 300 |
| BMAP-27B (2 µM) | | | | | | |
| Species | E. cloacae 4080 | 4.8 x 10⁵ (2.4 x 10⁴) | < 200 | 2400 | < 25 | < 20 |
| | E. coli IU342 | 1.7 x 10⁵ (5.6 x 10³) | < 200 | 850 | < 25 | < 20 |
| | K. pneumoniae 8893 | 2.1 x 10⁵ (2.8 x 10⁴) | < 200 | 1050 | < 25 | < 20 |
| | K. pneumoniae C-2 | 6.5 x 10⁵ (2.3 x 10⁴) | 2.6 x 10⁵ (5.7 x 10³) | 25 | 80 | < 20 |

| V. angustum | CFU/mL | Fold Reduction |
|---|---|---|
| Mock 1 | $1.9 \times 10^6$ | 1 |
| Mock 2 | $2.3 \times 10^6$ | 1 |
| 0.1 μM SMAP-29D | 212 | > 8,900 |
| 0.5 μM SMAP-29D | 94 | > 20,212 |
| 1.0 μM SMAP-29D | 113 | > 16,814 |
| 0.1 μM BMAP-27B | 168 | > 13,690 |
| 0.5 μM BMAP-27B | 27 | > 85,185 |
| 1.0 μM BMAP-27B | 26 | > 88,461 |

FIG. 8

| *V. fischeri* | Dilution | CFU | CFU/mL | Fold reduction |
|---|---|---|---|---|
| Mock | 2000x | 416 | 8.3x10^5 | 1 |
| SMAP-29D, 1 μM | 40x | 0 | <40 | > 20,750 |
| SMAP-29D 1 μM | 20X | 0 | <20 | > 41,500 |
| SMAP-29D 2 μM | 20X | 0 | <20 | > 41,500 |
| Mock | 100x | 480 | 9.6x10^5 | 1 |
| BMAP-27B, 0.5 μM | 40X | TMTC | TMTD | - |
| BMAP-27B 1 μM | 20X | 0 | <20 | > 48,000 |
| BMAP-27B 2 μM | 20X | 0 | <20 | > 48,000 |

FIG. 9

|  | CFU/ml |
|---|---|
| *E. coli* Top10pHNSHP45 | $1.7 \times 10^6$ ($4.8 \times 10^5$) |
| + Colistin | $1.3 \times 10^6$ ($1.3 \times 10^5$) |
| + BMAP-27B | $< 20$ ($5.8 \times 10^1$) |
| + SMAP-29D | $<1.1 \times 10^2$ ($5.2 \times 10^2$) |
| *E. coli* Top10 | $1.3 \times 10^6$ ($2.2 \times 10^5$) |
| + Colistin | $7.6 \times 10^2$ ($3.9 \times 10^2$) |
| + BMAP-27B | $1.3 \times 10^2$ ($5.8 \times 10^1$) |
| + SMAP-29D | $1.2 \times 10^3$ ($5.2 \times 10^2$) |

\* All cultures treated with 2 µM peptide.

| Peptide | Sequence | CFU/ml | Fold reduc. |
|---|---|---|---|
| Mock | | $5.4 \times 10^5$ | - |
| BMAP-27B | GRFKRLRKKLKKLFKKLSPVIPLLHLG | $1.6 \times 10^2$ | > 3000 |
| BMAP24 | GRFKRFRKKLKKLFKKLSPVIPLL--- | $1.0 \times 10^2$ | > 4000 |
| B22 | ----FRKKLKKLFKKLSPVIPLLKLG | $2.9 \times 10^2$ | > 3500 |

FIG. 13

BACTERICIDAL PEPTIDES AND USES THEREOF

CROSS-REFERENCE TO RELATED APPLICATIONS

This application is a continuation-in-part of PCT International Application No. PCT/US2017/024766, filed on Mar. 29, 2017, and claims the benefit under 35 USC § 119(e) of U.S. Provisional Application No. 62/657,222, filed on Apr. 13, 2018, and 62/314,608, filed on Mar. 29, 2016, the entire disclosures of which are incorporated herein by reference.

SEQUENCE LISTING

The instant application contains a Sequence Listing which has been submitted electronically in ASCII format and is hereby incorporated by reference in its entirety. The ASCII copy, created on Sep. 28, 2018, is named 29920-277325_SL.txt and is 18,432 bytes.

BACKGROUND

Foodborne illness is a significant problem worldwide. The Center for Disease Control and Prevention (CDC) estimates that 1 in 6 Americans get sick by consuming contaminated foods or beverages. In a large part due to the use of antibiotics in nontherapeutic growth of food animals, antibiotic-resistant bacteria that contaminate food are an increasing concern.

*Vibrios* are Gram-negative bacteria that occur naturally in marine environments. Among various foodborne pathogens, *Vibrios* are recognized as a potential fish pathogen that are capable of spreading quickly when fish are in close contact to one another. Upon infection by *Vibrios*, the infected fish may display lethargy, loss of appetite, and/or have necrotic sores. To date, a common method for preventing a *Vibrios* infection and for treating fish infected by *Vibrios* is to provide antibiotics in the water.

According to the Center for Disease Control (CDC), *Vibrio* bacteria live in saltwater. As such, consuming raw or undercooked shellfish, particularly oysters, can lead to vibriosis. It is documented that *Vibrios* are associated with uncooked shellfish and fish, which has had particularly significant consequences on foodborne illness. For example, several species of *Vibrio*, including *Vibrio parahaemolyticus*, are known to cause illness. Other potential human pathogens include *V. vulnificus* and *V. cholera* that can cause gastrointestinal illness. Symptoms consist of mild to moderate diarrhea, but can sometimes be severe, especially if the bacteria enter the bloodstream.

In view of the infection risks, safe shellfish preparation is necessary to avoid illness, especially among high risk people. High risk groups include people with weakened immune systems and people with chronic liver disease. Therefore, proper preparation, for example sterilization, of related food products that are sensitive to *Vibrios* infections is a desired development for control such bacteria mediated foodborne diseases.

Resistance to antimicrobial drugs is a natural phenomenon. As bacteria and other microbes are exposed to antibiotics, they will eventually develop resistance through random mutations and by acquiring resistance genes from other bacteria. Therefore, continually developing new drugs and judicious use of the available drugs is required.

Antibiotic resistance can arise through the overuse, or improper use, of antibiotics in both humans and animals. On the animal side, the concern centers on antibiotics provided to entire herds to either prevent disease or promote growth. In half of the countries in the world, including the United States and Canada, antibiotics are still used as growth promoters.

Resistance that arises in animals could affect humans in two ways. Food-borne pathogens could develop their resistance in animals before going on to infect people via the food supply. Or resistance genes could be transferred from animal bacteria to human pathogens through a process known as horizontal gene transfer, where genetic material is swapped between neighboring bacteria. In either scenario, food production safety and human health will be jeopardized by antibiotic resistant bacteria.

In order to contain effectively the foodborne, there are needs to develop novel effective alternatives to inhibit bacteria's growth and spread, hence prevent their potential harm to human health. This application provides one of such alternative.

SUMMARY

This disclosure provides compositions of antimicrobial peptides. In some embodiments, the antimicrobial peptides effectively kill various Gram-negative bacteria, particularly members of the Enterobacteriacea, including *Vibrios* bacterial strains within the genus.

In some embodiments, an antimicrobial peptide comprises an amino acid sequence of $X_1X_2X_3X_4X_5X_6RKKX_7KKLX_8KKLSPVIPLLX_9X_{10}X_{11}$ (SEQ ID NO: 20), wherein $X_1$ is a non-polar amino acid or absent, $X_2$ is a basic amino acid or absent, $X_3$ is a non-polar amino acid or absent, $X_4$ is a basic amino acid or absent, $X_5$ is a basic amino acid or absent, $X_6$ is a non-polar amino acid, $X_7$ is a non-polar amino acid, $X_8$ is a non-polar amino acid, $X_9$ is a basic amino acid or absent, $X_{10}$ is a non-polar amino acid or absent, and $X_{11}$ is a non-polar amino acid or absent; or a pharmaceutically acceptable salt thereof. In some embodiments, the antimicrobial peptide is C-terminally amidated.

In some embodiments, an antimicrobial peptide comprises an amino acid sequence of RGLRRLGRKIAHGVKKX$_{12}$GPTVLRIIRIAGX$_{13}$ (SEQ ID NO: 21), wherein $X_{12}$ is a polar amino acid or a non-polar amino acid and $X_{13}$ is a polar amino acid or absent; or a pharmaceutically acceptable salt thereof. In some embodiments, the antimicrobial peptide is chemically modified at the c-terminus with an amide This disclosure identifies effective compositions for killing bacteria, including those found in seafood. These compositions are selected from the peptides group consisting of SEQ ID NOs: 11-13 (BMAP-27A, BMAP-27B and BMAP-27C), SEQ ID NOs: 15-17 (SMAP-29B, SMAP-29C and SMAP-29D), SEQ ID NOs: 18-19 (BMAP-24 and B22), and SEQ ID NOs: 28-30.

In one preferred embodiment, the aforementioned peptide is BMAP-27A.

In one preferred embodiment, the aforementioned peptide is BMAP-27B.

In one preferred embodiment, the aforementioned peptide is BMAP-27C.

In another preferred embodiment, the aforementioned peptide is SMAP-29B.

In another preferred embodiment, the aforementioned peptide is SMAP-29C.

In another preferred embodiment, the aforementioned peptide is SMAP-29D.

In another preferred embodiment, the aforementioned peptide is BMAP-24.

In another preferred embodiment, the aforementioned peptide is B22.

In another preferred embodiment, the aforementioned peptide is B22a.

In another preferred embodiment, the aforementioned peptide is B22m1.

In another preferred embodiment, the aforementioned peptide is B22m2.

In another preferred embodiment, the aforementioned peptide is C-terminally amidated.

In another preferred embodiments, the N-terminus, the C-terminus, or both the N-terminus and C-terminus are substituted.

In another preferred embodiment, the aforementioned peptide is N-terminally pegylated and C-terminally amidated.

In another preferred embodiment, the aforementioned peptide is N-terminally acylated and C-terminally pegylated.

In another preferred embodiment, the aforementioned peptide is AB22a.

In another preferred embodiment, the aforementioned peptide is AB22P.

In another preferred embodiment, the aforementioned peptide is PB22N.

This disclosure further provides a method to sanitize raw seafood. The method comprises the steps of:
identifying a seafood source that is infected by Gram-negative bacteria;
providing the aforementioned seafood source with effective amount of at least one peptide selected from the group consisting of SEQ ID NOs: 11-13 (BMAP-27A, BMAP-27B and BMAP-27C) SEQ ID NOs: 15-17 (SMAP-29B, SMAP-29C and SMAP-29D), SEQ ID NOs. 18-19 (BMAP-24 and B22), and SEQ ID NOs: 28-30, wherein the selected peptide kills aforementioned Gram-negative bacteria in the food source.

In one preferred embodiment, the aforementioned Gram-negative bacteria are *Vibrios*.

The make and use of these peptides to sterilize raw fish and shellfish for food consumption are within the scope of the protection.

In one preferred embodiment, the aforementioned Gram-negative bacteria are a species in the *Vibrios* genus, an *Escherichia coli*, an *Enterobacter cloacae*, a *Klebsiella pneumoniae*, a *Pseudomonas aeruginosa*, a *Serratia marcescens*, or a mixture thereof.

In one preferred embodiment, the aforementioned Gram-negative bacteria are selected from the group consisting of *V. cholerae* (the causative agent of cholera), *V. parahaemolyticus*, *V. vulnificus*, and *V. fischeri*. In one preferred embodiment, the aforementioned Gram-negative bacteria are *V. fischeri*.

In one preferred embodiment, the aforementioned seafood is a fish or shellfish.

In one preferred embodiment, the aforementioned at least one peptide is degradable to amino acids along with said seafood consumption.

In one preferred embodiment, the aforementioned peptide is BMAP-27A.

In one preferred embodiment, the aforementioned peptide is BMAP-27B.

In one preferred embodiment, the aforementioned peptide is BMAP-27C.

In another preferred embodiment, the aforementioned peptide is SMAP-29B.

In another preferred embodiment, the aforementioned peptide is SMAP-29C.

In another preferred embodiment, the aforementioned peptide is SMAP-29D.

In another preferred embodiment, the aforementioned peptide is BMAP-24.

In another preferred embodiment, the aforementioned peptide is B22.

In another preferred embodiment, the aforementioned peptide is B22a.

In another preferred embodiment, the aforementioned peptide is B22m1.

In another preferred embodiment, the aforementioned peptide is B22m2.

In another preferred embodiment, the aforementioned peptide is C-terminally amidated.

In another preferred embodiment, the aforementioned peptide is AB22a.

In another preferred embodiment, the aforementioned peptide is AB22P.

In another preferred embodiment, the aforementioned peptide is PB22N.

This disclosure further provides a method of treating Gram-negative bacteria infected animals. The method comprises providing the infected animals effective amount of at least one peptide selected from the group consisting of SEQ ID NOs: 11-13 (BMAP-27A, BMAP-27B and BMAP-27C), SEQ ID NOs: 15-17 (SMAP-29B, SMAP-29C and SMAP-29D), SEQ ID NOs: 18-19 (BMAP-24 and B22), SEQ ID NOs: 28-30; and SEQ ID NOs: 32-34.

In one preferred embodiment, the aforementioned infected animals are grown from fresh water aquaculture.

In one preferred embodiment, the aforementioned Gram-negative bacteria are *V. fischeri*.

In another embodiment in accordance with the present disclosure, a method of killing Gram-negative bacteria, the method comprises contacting a Gram-negative bacteria with an antimicrobial peptide in accordance with the present disclosure; or a pharmaceutically acceptable salt thereof.

In another embodiment in accordance with the present disclosure, a method of treating a Gram-negative bacterial infection in a subject in need thereof, the method comprises administering to the subject an effective amount of an antimicrobial peptide according to the present disclosure; or a pharmaceutically acceptable salt thereof.

The following numbered embodiments are contemplated and are non-limiting:

1. An antimicrobial peptide comprising an amino acid sequence of (SEQ ID NO: 20)
$X_1X_2X_3X_4X_5X_6RKKX_7KKLX_8KKLSPVIPLLX_9X_{10}X_{11}$ wherein $X_1$ is a non-polar amino acid or absent, $X_2$ is a basic amino acid or absent, $X_3$ is a non-polar amino acid or absent, $X_4$ is a basic amino acid or absent, $X_5$ is a basic amino acid or absent, $X_6$ is a non-polar amino acid, $X_7$ is a non-polar amino acid, $X_8$ is a non-polar amino acid, $X_9$ is a basic amino acid or absent, $X_{10}$ is a non-polar amino acid or absent, $X_{11}$ is a non-polar amino acid or absent; or a pharmaceutically acceptable salt thereof.

2. The antimicrobial peptide of clause 1, wherein the antimicrobial peptide comprises an amino acid sequence of (SEQ ID NO: 24)
$X_1X_2X_3X_4X_5X_6RKKX_7KKLX_8KKLSPVIPLLX_9X_{10}X_{11}$ wherein X₁ is G or absent, X₂ is R or absent, X₃ is F, A, or absent, X₄ is K or absent, X₅ is R or absent, X₆ is F or L, X₇ is F or L, X₈ is F or A, X₉ is H, K, or absent, X₁₀ is L or absent, X₁₁ is G or absent, provided that when X₇ is F, X₆ is L; or a pharmaceutically salt thereof.

3. The antimicrobial peptide of clause 1, wherein the antimicrobial peptide comprises an amino acid sequence of

```
                                              (SEQ ID NO: 22)
X₆RKKX₇KKLX₈KKLSPVIPLLX₉X₁₀X₁₁
``` wherein X₆ is a non-polar amino acid, X₇ is a non-polar amino acid, X₈ is a non-polar amino acid, X₉ is a basic amino acid, X₁₀ is a non-polar amino acid, and X₁₁ is a non-polar amino acid; or a pharmaceutically acceptable salt thereof.

4. The antimicrobial peptide of clause 3, wherein the antimicrobial peptide comprises an amino acid sequence of

```
                                              (SEQ ID NO: 25)
X₆RKKX₇KKLX₈KKLSPVIPLLX₉X₁₀X₁₁
``` wherein X₆ is F or L, X₇ is F or L, X₈ is F or A, X₉ is H or K, X₁₀ is L, X₁₁ is G, provided that when X₇ is F, X₆ is L; or a pharmaceutically salt thereof.

5. The antimicrobial peptide of clause 1, wherein the antimicrobial peptide comprises an amino acid sequence of

```
                                              (SEQ ID NO: 23)
X₁X₂X₃X₄X₅X₆RKKX₇KKLX₈KKLSPVIPLL
``` wherein X₁ is a non-polar amino acid, X₂ is a basic amino acid, X₃ is a non-polar amino acid, X₄ is a basic amino acid, X₅ is a basic amino acid, X₆ is a non-polar amino acid, X₇ is a non-polar amino acid, and X₈ is a non-polar amino acid; or a pharmaceutically acceptable salt thereof.

6. The antimicrobial peptide of clause 5, wherein the antimicrobial peptide comprises an amino acid sequence of

```
                                              (SEQ ID NO: 26)
X₁X₂X₃X₄X₅X₆RKKX₇KKLX₈KKLSPVIPLL
``` wherein X₁ is G, X₂ is R, X₃ is F or A, X₄ is K, X₅ is R, X₆ is F or L, X₇ is F or L, X₈ is F or A, provided that when X₇ is F, X₆ is L; or a pharmaceutically salt thereof.

7. The antimicrobial peptide of any one of clauses 1-6, wherein X₇ is L; or a pharmaceutically acceptable salt thereof.

8. The antimicrobial peptide of clause 1 or 2, wherein the antimicrobial peptide comprises a sequence that is at least 90%, at least 93%, or at least 95% identical to a sequence selected from the group consisting of SEQ ID NO: 11, SEQ ID NO: 12, SEQ ID NO: 13, SEQ ID NO: 18, and SEQ ID NO: 19; or a pharmaceutically acceptable salt thereof.

9. The antimicrobial peptide of clause 1 or 2, wherein the antimicrobial peptide comprises a sequence that is at least 90%, at least 93%, or at least 95% identical to a sequence selected from the group consisting of SEQ ID NO:12, SEQ ID NO:13, SEQ ID NO:18, and SEQ ID NO:19; or a pharmaceutically acceptable salt thereof.

10. The antimicrobial peptide of any one of clauses 1-8, wherein the antimicrobial peptide comprises SEQ ID NO:11; or a pharmaceutically acceptable salt thereof.

11. The antimicrobial peptide of any one of clauses 1-8 or 10, wherein the antimicrobial peptide consists of the amino acid sequence of SEQ ID NO:11; or a pharmaceutically acceptable salt thereof.

12. The antimicrobial peptide of any one of clauses 1-9, wherein the antimicrobial peptide comprises SEQ ID NO:12; or a pharmaceutically acceptable salt thereof.

13. The antimicrobial peptide of any one of clauses 1-9 or 12, wherein the antimicrobial peptide consists of the amino acid sequence of SEQ ID NO:12; or a pharmaceutically acceptable salt thereof.

14. The antimicrobial peptide of any one of clauses 1-9, wherein the antimicrobial peptide comprises SEQ ID NO:13; or a pharmaceutically acceptable salt thereof.

15. The antimicrobial peptide of any one of clauses 1-9 or 14, wherein the antimicrobial peptide consists of the amino acid sequence of SEQ ID NO:13.

16. The antimicrobial peptide of any one of clauses 1-2 or 5-9, wherein the antimicrobial peptide comprises SEQ ID NO:18; or a pharmaceutically acceptable salt thereof.

17. The antimicrobial peptide of any one of clauses 1-2, 5-9, or 16, wherein the antimicrobial peptide consists of the amino acid sequence of SEQ ID NO:18; or a pharmaceutically acceptable salt thereof.

18. The antimicrobial peptide of any one of clauses 1-2 or 7-9, wherein the antimicrobial peptide comprises SEQ ID NO:19; or a pharmaceutically acceptable salt thereof.

19. The antimicrobial peptide of any one of clauses 1-4, 7-9, or 18, wherein the antimicrobial peptide consists of the amino acid sequence of SEQ ID NO:19; or a pharmaceutically acceptable salt thereof.

20. The antimicrobial peptide of any one of clauses 1-19 further comprising a reporter; or a pharmaceutically acceptable salt thereof.

21. The antimicrobial peptide of clause 20, wherein the reporter is a fluorophore; or a pharmaceutically acceptable salt thereof.

22. A pharmaceutically acceptable salt of any one of clauses 1-21.

23. An antimicrobial peptide comprising an amino acid sequence of

```
                                              (SEQ ID NO: 21)
RGLRRLGRKIAHGVKKX₁₂GPTVLRIIRIAGX₁₃
``` wherein X₁₂ is a polar amino acid or a non-polar amino acid and X₁₃ is a polar amino acid or absent; or a pharmaceutically acceptable salt thereof.

24. The antimicrobial peptide of clause 19, wherein the antimicrobial peptide comprises an amino acid sequence of

```
                                              (SEQ ID NO: 27)
RGLRRLGRKIAHGVKKX₁₂GPTVLRIIRIAGX₁₃
``` wherein X₁₂ is Y, C, or L and X₁₃ is C or absent, provided that when X₁₂ is Y, X₁₃ is C; or a pharmaceutically acceptable salt thereof.

25. The antimicrobial peptide of clause 23 or 24, wherein X₁₂ is C or L; or a pharmaceutically acceptable salt thereof.

26. The antimicrobial peptide of any one of clauses 23-25, wherein the antimicrobial peptide comprises a sequence that is at least 90%, at least 93%, or at least 95% identical to a sequence selected from the group consisting of SEQ ID NO:15, SEQ ID NO:16, and SEQ ID NO:17; or a pharmaceutically acceptable salt thereof.

27. The antimicrobial peptide of any one of clauses 23-26, wherein the antimicrobial peptide comprises SEQ ID NO:15; or a pharmaceutically acceptable salt thereof.

28. The antimicrobial peptide of any one of clauses 23-27, wherein the antimicrobial peptide consists of the amino acid sequence of SEQ ID NO:15; or a pharmaceutically acceptable salt thereof.

29. The antimicrobial peptide of any one of clauses 23-26, wherein the antimicrobial peptide comprises SEQ ID NO:16; or a pharmaceutically acceptable salt thereof.

30. The antimicrobial peptide of any one of clauses 23-26 or 29, wherein the antimicrobial peptide consists of the amino acid sequence of SEQ ID NO:16; or a pharmaceutically acceptable salt thereof.

31. The antimicrobial peptide of any one of clauses 23-26, wherein the antimicrobial peptide comprises SEQ ID NO:17; or a pharmaceutically acceptable salt thereof.

32. The antimicrobial peptide of any one of clauses 23-26 or 31, wherein the antimicrobial peptide consists of the amino acid sequence of SEQ ID NO:17; or a pharmaceutically acceptable salt thereof.

33. The antimicrobial peptide of any one of clauses 23-32 further comprising a reporter; or a pharmaceutically acceptable salt thereof.

34. The antimicrobial peptide of clause 33, wherein the reporter is a fluorophore; or a pharmaceutically acceptable salt thereof.

35. A pharmaceutically acceptable salt of any one of clauses 23-34.

36. A method of killing Gram-negative bacteria, the method comprising
contacting Gram-negative bacteria with an antimicrobial peptide comprising an amino acid according to any one of clauses 1-35; or a pharmaceutically acceptable salt thereof.

37. The method of clause 36, wherein the Gram-negative bacteria are a foodborne bacteria.

38. The method of clause 36 or 37, wherein the Gram-negative bacteria are a species in the *Vibrios* genus, an *Escherichia coli*, an *Enterobacter cloacae*, a *Klebsiella pneumoniae*, a *Pseudomonas aeruginosa*, a *Serratia marcescens*, or a mixture thereof.

39. The method of any one of clauses 36-38, wherein the Gram-negative bacteria are found in seafood.

40. The method of clause 39 wherein the seafood is a fish or shellfish.

41. The method of any one of clauses 36-38, wherein the antimicrobial peptide is degraded to amino acids along with seafood consumption.

42. The method of any one of clauses 36-41, wherein the Gram-negative bacteria are selected from the group consisting of *V. cholerae* (the causative agent of cholera), *V. parahaemolyticus*, *V. vulnificus*, and *V. fischeri*.

43. The method of any one of clauses 36-42, wherein the Gram-negative bacteria are resistant to antibiotics.

44. The method of any one of clauses 36-43, wherein the Gram-negative bacteria are resistant to polymyxins.

45. The method of any one of clauses 36-44, wherein the Gram-negative bacteria are resistant to colistin.

46. A method of treating a Gram-negative bacterial infection in a subject in need thereof, the method comprising
administering to the subject an effective amount of an antimicrobial peptide according to any one of clauses 1-35; or a pharmaceutically acceptable salt thereof.

47. The method of clause 46, wherein the subject is an animal from an aquaculture.

48. The method of clause 46 or 47, wherein the animal from an aquaculture is a fish or a shellfish.

49. The method of clause 46, wherein the subject is a mammal.

50. The method of clause 46 or 49, wherein the subject is a mouse or a human.

51. The method of any one of clauses 46-50, 38 wherein the Gram-negative bacteria are a species in the *Vibrios* genus, an *Escherichia coli*, an *Enterobacter cloacae*, a *Klebsiella pneumoniae*, a *Pseudomonas aeruginosa*, a *Serratia marcescens*, or a mixture thereof.

52. The method of any one of clauses 46-51, wherein the Gram-negative bacteria are selected from the group consisting of *V. cholerae* (the causative agent of cholera), *V. parahaemolyticus*, *V. vulnificus*, and *V. fischeri*.

53. An antimicrobial peptide according to any one of clauses 1-35, or a pharmaceutically acceptable salt thereof, for use in a method of treating a Gram-negative bacterial infection in a subject.

54. Use of an antimicrobial peptide according to any one of clauses 1-35 in the manufacture of a medicament for treating a Gram-negative bacterial infection.

55. A method of providing sterilization to raw seafood, the method comprising
contacting a seafood source with effective amount of at least one antimicrobial peptide of any one of clauses 1-35.

56. An antimicrobial peptide comprising an amino acid sequence of $$X_1X_2X_3X_4X_5X_6RKKX_7KKLX_8KKLSPVIPLLX_9X_{10}X_{11} \quad \text{(SEQ ID NO: 20)}$$

wherein $X_1$ is a non-polar amino acid or absent, $X_2$ is a basic amino acid or absent, $X_3$ is a non-polar amino acid or absent, $X_4$ is a basic amino acid or absent, $X_5$ is a basic amino acid or absent, $X_6$ is a non-polar amino acid, $X_7$ is a non-polar amino acid, $X_8$ is a non-polar amino acid, $X_9$ is a basic amino acid or absent, $X_{10}$ is a non-polar amino acid or absent, $X_{11}$ is a non-polar amino acid or absent; and $X_{11}$ is optionally C-terminally amidated; or a pharmaceutically acceptable salt thereof.

57. The antimicrobial peptide of clause 56, wherein the antimicrobial peptide comprises an amino acid sequence of $$X_6RKKX_7KKLX_8KKLSPVIPLLX_9X_{10}X_{11} \quad \text{(SEQ ID NO: 22)}$$

wherein $X_6$ is a non-polar amino acid, $X_7$ is a non-polar amino acid, $X_8$ is a non-polar amino acid, $X_9$ is a basic amino acid, $X_{10}$ is a non-polar amino acid, $X_{11}$ is a non-polar amino acid, and $X_{11}$ is optionally C-terminally amidated; or a pharmaceutically acceptable salt thereof.

58. The antimicrobial peptide of clause 56, wherein the antimicrobial peptide comprises an amino acid sequence of $$X_6RKKX_7KKLX_8KKLSPVIPLLX_9X_{10}X_{11} \quad \text{(SEQ ID NO: 22)}$$

wherein $X_6$ is a non-polar amino acid, $X_7$ is a non-polar amino acid, $X_8$ is a non-polar amino acid, $X_9$ is a basic amino acid, $X_{10}$ is a non-polar amino acid, $X_{11}$ is a non-polar amino acid, and $X_{11}$ is optionally C-terminally amidated; or a pharmaceutically acceptable salt thereof.

59. The antimicrobial peptide of clause 58, wherein the antimicrobial peptide comprises an amino acid sequence of $$X_6RKKX_7KKLX_8KKLSPVIPLLX_9X_{10}X_{11} \quad \text{(SEQ ID NO: 25)}$$

wherein $X_6$ is F, L or A, $X_7$ is F or L, $X_8$ is F or A, $X_9$ is H or K, $X_{10}$ is L, $X_{11}$ is G, and $X_{11}$ is optionally C-terminally amidated, provided that when $X_7$ is F, $X_6$ is L; or a pharmaceutically salt thereof.

60. The antimicrobial peptide of any one of clauses 56-59, wherein $X_7$ is L; or a pharmaceutically acceptable salt thereof.

61. The antimicrobial peptide of any one of clauses 56-60, wherein $X_9$ is K; or a pharmaceutically acceptable salt thereof.

62. The antimicrobial peptide of any one of clauses 56-58 or 60-61, wherein $X_{10}$ is L; or a pharmaceutically acceptable salt thereof.

63. The antimicrobial peptide of any one of clauses 56-58 or 60-62, wherein $X_{11}$ is G; or a pharmaceutically acceptable salt thereof.

64. The antimicrobial peptide of any one of clauses 56-63, wherein the antimicrobial peptide is C-terminally amidated.

65. The antimicrobial peptide of any one of clauses 56-59, wherein $X_{11}$ is C-terminally amidated.

65a. The antimicrobial peptide of any of the preceding clauses, wherein the N-terminus, the C-terminus, or both the N-terminus and C-terminus are substituted.

65b. The antimicrobial peptide of any of the preceding clauses, wherein peptide is N-terminally pegylated and C-terminally amidated.

65c. The antimicrobial peptide of any of the preceding clauses, wherein the peptide is N-terminally acylated and C-terminally pegylated.

66. The antimicrobial peptide of clause 56, wherein the antimicrobial peptide comprises a sequence that is at least 90%, at least 93%, or at least 95% identical to a sequence selected from the group consisting of SEQ ID NO:11, SEQ ID NO:12, SEQ ID NO:13, SEQ ID NO:18, SEQ ID NO:19, SEQ ID NO:28, SEQ ID NO:29, and SEQ ID NO:30; or a pharmaceutically acceptable salt thereof.

67. The antimicrobial peptide of clause 56, wherein the antimicrobial peptide comprises a sequence that is at least 90%, at least 93%, or at least 95% identical to a sequence selected from the group consisting of SEQ ID NO:19, SEQ ID NO:28, SEQ ID NO:29, and SEQ ID NO:30; or a pharmaceutically acceptable salt thereof.

68. The antimicrobial peptide of clause 56, wherein the antimicrobial peptide comprises a sequence that is at least 90%, at least 93%, or at least 95% identical to a sequence selected from the group consisting of SEQ ID NO:28, SEQ ID NO:29, and SEQ ID NO:30; or a pharmaceutically acceptable salt thereof.

68a. The antimicrobial peptide of clause 56, wherein the antimicrobial peptide comprises a sequence that is at least 90%, at least 93%, or at least 95% identical to a sequence selected from the group consisting of SEQ ID NO:28, SEQ ID NO:29, SEQ ID NO:30; and SEQ ID NOs: 32-34 or a pharmaceutically acceptable salt thereof.

69. The antimicrobial peptide of clause 56, wherein the antimicrobial peptide comprises SEQ ID NO:28; or a pharmaceutically acceptable salt thereof.

70. The antimicrobial peptide of clause 56, wherein the antimicrobial peptide comprises SEQ ID NO:29; or a pharmaceutically acceptable salt thereof.

71. The antimicrobial peptide of clause 56, wherein the antimicrobial peptide comprises SEQ ID NO:30; or a pharmaceutically acceptable salt thereof.

71a. The antimicrobial peptide of clause 56, wherein the antimicrobial peptide comprises SEQ ID NO:32; or a pharmaceutically acceptable salt thereof.

71b. The antimicrobial peptide of clause 56, wherein the antimicrobial peptide comprises SEQ ID NO:33; or a pharmaceutically acceptable salt thereof.

71c. The antimicrobial peptide of clause 56, wherein the antimicrobial peptide comprises SEQ ID NO:34; or a pharmaceutically acceptable salt thereof.

72. The antimicrobial peptide of any one of clauses 56-71 further comprising a reporter; or a pharmaceutically acceptable salt thereof.

73. The antimicrobial peptide of clause 72, wherein the reporter is a fluorophore; or a pharmaceutically acceptable salt thereof.

74. A pharmaceutically acceptable salt of any one of clauses 56-73.

75. An antimicrobial peptide comprising an amino acid sequence of $$X_1X_2X_3X_4X_5X_6RKKX_7KKLX_8KKLSPVIPLLX_9X_{10}X_{11}\text{-}NH_2 \quad (\text{SEQ ID NO: 20})$$

wherein $X_1$ is a non-polar amino acid or absent, $X_2$ is a basic amino acid or absent, $X_3$ is a non-polar amino acid or absent, $X_4$ is a basic amino acid or absent, $X_5$ is a basic amino acid or absent, $X_6$ is a non-polar amino acid, $X_7$ is a non-polar amino acid, $X_8$ is a non-polar amino acid, $X_9$ is a basic amino acid or absent, $X_{10}$ is a non-polar amino acid or absent, $X_{11}$ is a non-polar amino acid or absent; and $X_{11}$ C-terminally amidated; or a pharmaceutically acceptable salt thereof.

76. The antimicrobial peptide of clause 75, wherein the antimicrobial peptide comprises an amino acid sequence of $$X_6RKKX_7KKLX_8KKLSPVIPLLX_9X_{10}X_{11}\text{-}NH_2 \quad (\text{SEQ ID NO: 22})$$

wherein $X_6$ is a non-polar amino acid, $X_7$ is a non-polar amino acid, $X_8$ is a non-polar amino acid, $X_9$ is a basic amino acid, $X_{10}$ is a non-polar amino acid, $X_{11}$ is a non-polar amino acid, and $X_{11}$ is C-terminally amidated; or a pharmaceutically acceptable salt thereof.

77. The antimicrobial peptide of clause 75, wherein the antimicrobial peptide comprises an amino acid sequence of $$X_6RKKX_7KKLX_8KKLSPVIPLLX_9X_{10}X_{11}\text{-}NH_2 \quad (\text{SEQ ID NO: 22})$$

wherein $X_6$ is a non-polar amino acid, $X_7$ is a non-polar amino acid, $X_8$ is a non-polar amino acid, $X_9$ is a basic amino acid, $X_{10}$ is a non-polar amino acid, $X_{11}$ is a non-polar amino acid, and $X_{11}$ is C-terminally amidated; or a pharmaceutically acceptable salt thereof.

78. The antimicrobial peptide of clause 75, wherein the antimicrobial peptide comprises an amino acid sequence of $$X_6RKKX_7KKLX_8KKLSPVIPLLX_9X_{10}X_{11}\text{-}NH_2 \quad (\text{SEQ ID NO: 25})$$

wherein $X_6$ is F, L or A, $X_7$ is F or L, $X_8$ is F or A, $X_9$ is H or K, $X_{10}$ is L, $X_{11}$ is G, and $X_{11}$ is C-terminally amidated, provided that when $X_7$ is F, $X_6$ is L; or a pharmaceutically salt thereof.

79. The antimicrobial peptide of any one of clauses 75-78, wherein $X_7$ is L; or a pharmaceutically acceptable salt thereof.

80. The antimicrobial peptide of any one of clauses 75-79, wherein $X_9$ is K; or a pharmaceutically acceptable salt thereof.

81. The antimicrobial peptide of any one of clauses 75-77 or 79-80, wherein $X_{10}$ is L; or a pharmaceutically acceptable salt thereof.

82. The antimicrobial peptide of any one of clauses 75-77 or 79-81, wherein $X_{11}$ is G; or a pharmaceutically acceptable salt thereof.

83. The antimicrobial peptide of clause 75, wherein the antimicrobial peptide comprises a sequence that is at least 90%, at least 93%, or at least 95% identical to a sequence selected from the group consisting of SEQ ID NO:28, SEQ ID NO:29, and SEQ ID NO:30; or a pharmaceutically acceptable salt thereof.

84. The antimicrobial peptide of clause 75, wherein the antimicrobial peptide comprises SEQ ID NO:28; or a pharmaceutically acceptable salt thereof.

85. The antimicrobial peptide of clause 75, wherein the antimicrobial peptide comprises SEQ ID NO:29; or a pharmaceutically acceptable salt thereof.

86. The antimicrobial peptide of clause 75, wherein the antimicrobial peptide comprises SEQ ID NO:30; or a pharmaceutically acceptable salt thereof.

87. The antimicrobial peptide of any one of clauses 75-86 further comprising a reporter; or a pharmaceutically acceptable salt thereof.

88. The antimicrobial peptide of clause 87, wherein the reporter is a fluorophore; or a pharmaceutically acceptable salt thereof.

89. A pharmaceutically acceptable salt of any one of clauses 75-88.

90. A method of killing Gram-negative bacteria, the method comprising
contacting Gram-negative bacteria with an antimicrobial peptide comprising an amino acid according to any one of clauses 56-89; or a pharmaceutically acceptable salt thereof.

91. The method of clause 90, wherein the Gram-negative bacteria are a foodborne bacteria.

92. The method of clause 90 or 91, wherein the Gram-negative bacteria are a species in the *Vibrios* genus, an *Escherichia coli*, *Enterobacter cloacae*, a *Klebsiella pneumoniae*, a *Pseudomonas aeruginosa*, a member of the Enterobacterioacea, or a mixture thereof.

93. The method of any one of clauses 90-92, wherein the Gram-negative bacteria are found in seafood.

94. The method of clause 93 wherein the seafood is a fish or shellfish.

95. The method of any one of clauses 90-92, wherein the antimicrobial peptide is degraded to amino acids along with seafood consumption.

96. The method of any one of clauses 90-95, wherein the Gram-negative bacteria are selected from the group consisting of *V. cholerae* (the causative agent of cholera), *V. parahaemolyticus*, *V. vulnificus*, and *V. fischeri*.

97. The method of any one of clauses 90-96, wherein the Gram-negative bacteria are resistant to antibiotics.

98. The method of any one of clauses 90-97, wherein the Gram-negative bacteria are resistant to polymyxins.

99. The method of any one of clauses 90-98, wherein the Gram-negative bacteria are resistant to colistin.

100. The method of clause 90, wherein the Gram-negative bacteria are a species of *Escherichia coli*, *Klebsiella pneumoniae*, *Enterobacter cloacae*, *Pseudomonas aeruginosa*, a member of the Enterobacterioacea, or a mixture thereof.

101. The method of clause 100, wherein the Enterobacterioacea is an *Enterobacter cloacae*.

102. The method of any one of clauses 100-101, wherein the Gram-negative bacteria are antibiotic resistant.

103. The method of clause 102, wherein the antibiotic is a carbapenem or polymyxin.

104. The method of clause 103, wherein the polymyxin is colistin.

105. The method of clause 103, wherein the carbapenem is imipenem or meropenem.

106. The method of anyone of clauses 90-105, wherein the Gram-negative bacteria are in a biofilm.

107. The method of anyone of clauses 90-106, wherein the antimicrobial peptide is in a composition with an antibiotic.

108. A composition comprising an antimicrobial peptide from anyone of clauses 1-89 and an antibiotic.

109. A method of treating a Gram-negative bacterial infection in a subject in need thereof, the method comprising:
administering to the subject an effective amount of an antimicrobial peptide according to any one of clauses 56-89; or a pharmaceutically acceptable salt thereof.

110. The method of clause 109, wherein the subject is an animal from an aquaculture.

111. The method of clause 109 or 110, wherein the animal from an aquaculture is a fish or a shellfish.

112. The method of clause 106, wherein the subject is a mammal.

113 The method of clause 112, wherein the subject is a mouse or a human.

114. The method of any one of clauses 109-113 wherein the Gram-negative bacteria are a species of *Vibrios, Escherichia coli, Enterobacter cloacae, Klebsiella pneumoniae, Pseudomonas aeruginosa*, a member of the Enterobacterioacea, or a mixture thereof.

115. The method of any one of clauses 109-114, wherein the Gram-negative bacteria are a species of *Escherichia coli, Klebsiella pneumoniae, Enterobacter cloacae, Pseudomonas aeruginosa*, a member of the Enterobacterioacea, or a mixture thereof.

116. A method of providing sterilization to raw seafood, the method comprising:
contacting a seafood source with effective amount of at least one antimicrobial peptide of any one of clauses 1-89.

BRIEF DESCRIPTIONS OF THE DRAWINGS

The detailed description particularly refers to the accompanying figures in which:

FIGS. 1A-C show a general illustration of antimicrobial peptides. FIG. 1A shows a general illustration showing how antimicrobial peptides may prevent infections (selected from Zasloff, Nature Medicine 2006). FIG. 1B shows a space-filling model of an antimicrobial peptide. FIG. 1C shows a pictorial representation of an antimicrobial peptide (selected from Wang et al., J. Biol. Chem. 2008).

FIGS. 2A-D show a proposed mechanism of bacterial killing by an antimicrobial peptide (adapted from Nguyen et al. 2011. Trends in Biotechnology 29, 464). FIG. 2A shows antimicrobial peptides undergo a conformational change near a bacterial membrane. FIG. 2B shows a toroidal pore formed in the bacterial membrane. FIG. 2C shows a disordered toroidal pore formed in a bacterial membrane. FIG. 2D shows non-lytic membrane depolarization in a bacterial membrane.

FIGS. 3A-B show cathelicidin peptides produced by different animals.

FIG. 3A shows a phylogenetic relationship of cathelicidin peptides from mammals. The Figure is derived from results of Zanetti et al (J. Leuk. Biol. 2004). FIG. 3B shows the names, lengths, and sequences of antimicrobial peptides with the residues predicted to form an alpha-helix underlined (SEQ ID NOS 1-9, respectively, in order of appearance).

FIGS. 4A-D show SMAP-29 and variants thereof kill bacteria and have reduced cytotoxicity. FIG. 4A shows SMAP-29 and variants thereof effectively kill bacteria (SEQ ID NOS 14, 15 and 17, respectively, in order of appearance). The bacterial strains tested are: Klebsiella pneumoniae (K. p.), Serratia marcescens (S. m.), Enterobacter cloacae (E. cl.), Escherichia coli (E. co.), and Pseudomonas aeruginosa (P. a.). FIG. 4B shows RBC lysis does not correlate with antibacterial activity. LL-37, SMAP-29, SMAP-29B, and SMAP-29D all had bactericidal effects but showed decreased RBC lysis compared to the control $H_2O$. FIG. 4C shows the effective antibacterial activity does not correlate with higher mammalian cytotoxicity. Cultured human cells were tested with antimicrobial peptides LL-37, SMAP-29, SMAP-29B, and SMAP-29D. MTT assays indicated no increased cytotoxicity compared to the controls. FIG. 4D shows the ability of SMAP-29 and variants thereof to enhance signal transduction by Toll-like receptor 3 (TLR3) and to suppress signal transduction by Toll-like receptor 4 (TLR4). IL-6 levels secreted by the cells were quantified using an ELISA assay. FIG. 4E shows the ability of the SMAP29 series of peptides for enhancement of signal transduction by TLR3 and to suppress signal transduction by TLR4. IL-6 levels secreted by the cells were quantified using an ELISA assay.

FIGS. 5A-E show BMAP-27 variants thereof kill bacteria and have reduced cytotoxicity. FIG. 5A shows BMAP-27 and variants thereof effectively kill bacteria (SEQ ID NOS 10-13, respectively, in order of appearance). The bacterial strains tested are: Klebsiella pneumonia (K. p.), Serratia marcescens (S. m.), Enterobacter cloacae (E. cl.), Escherichia coli (E. co.), and Pseudomonas aeruginosa (P. a.). FIG. 5B shows RBC lysis does not correlate with antibacterial activity. LL-37, BMAP-27, BMAP-27A, BMAP-27B and BMAP-27C all had bacterial killing effects but showed decreased RBC lysis compared to the control $H_2O$. FIG. 5C shows the effective antibacterial activity does not correlate with higher mammalian cytotoxicity. Cultured human cells were tested with the antimicrobial peptides BMAP-27, BMAP-27A, BMAP-27B, and BMAP-27C. MTT assays indicated no increased cytotoxicity compared to the controls. FIG. 5D shows the ability of BMAP-27 and variants thereof enhance signal transduction by TLR3 and suppress signal transduction by TLR4. IL-6 levels secreted by the cells were quantified using an ELISA assay. FIG. 5E shows the ability of BMAP27 and variants thereof enhance signal transduction by TLR3 and suppress signal transduction by TLR4. IL-6 levels secreted by the cells were quantified using an ELISA assay.

FIGS. 6A-B shows the rate of bacterial killing by the antimicrobial peptides. FIG. 6A shows a comparison of SMAP-29D and BMAP-27B bacterial killing effect as compared the antibiotic Kanamycin. FIG. 6B shows SMAP-29D and BMAP-27B at 2 µM concentration had exponentially reduced bacterial colony forming units within 5 min, measured on the bacteria strains.

FIG. 8 shows SMAP-29D and BMAP-27B killing of V. angustum.

FIG. 9 shows SMAP-29D and BMAP-27B killing of V. fischeri.

Figure 10A:
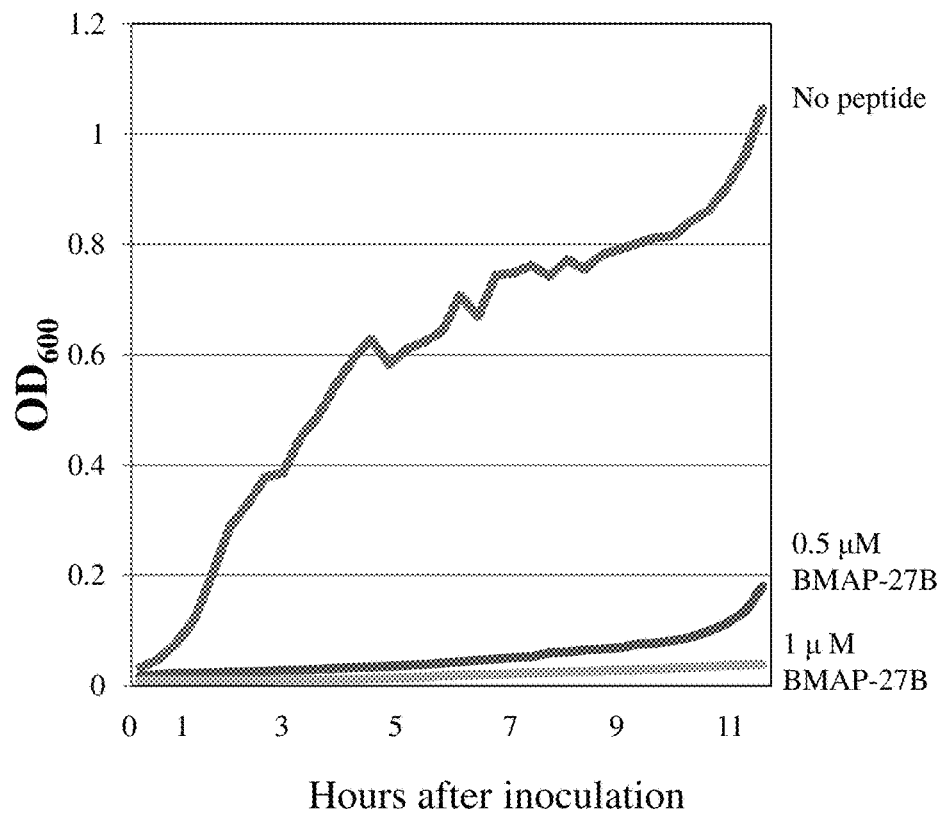
Figure 10B:
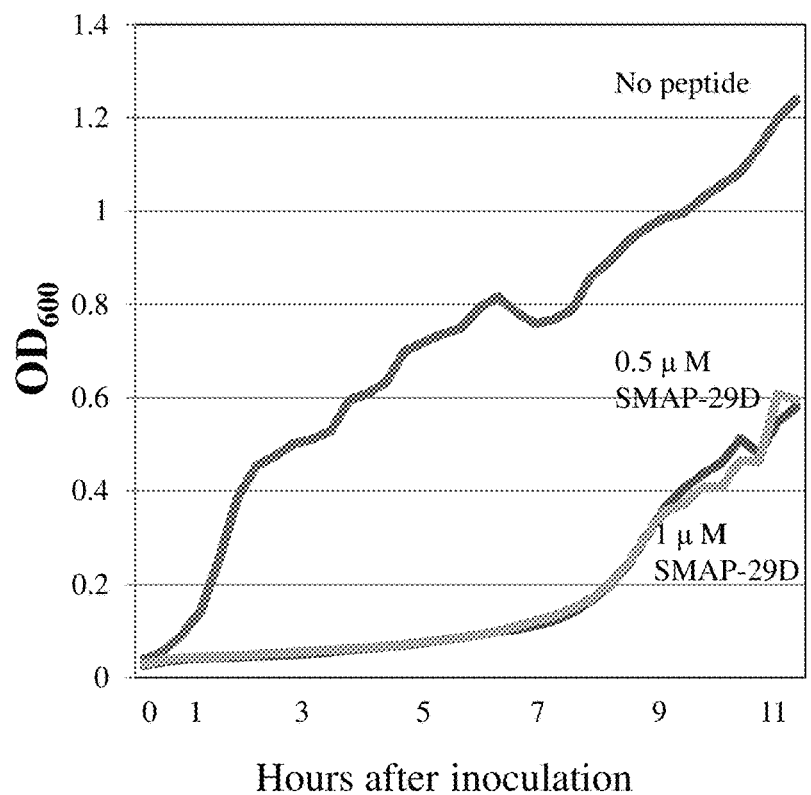

FIGS. 10A-B show V. vulnificus YJ016 growth curve in the absence and presence of antimicrobial peptides. FIG. 10A shows the growth curve in the presence of different concentrations of BMAP-27B. FIG. 10B shows the growth curve in the presence of different concentrations of SMAP-29D.

Figure 11:
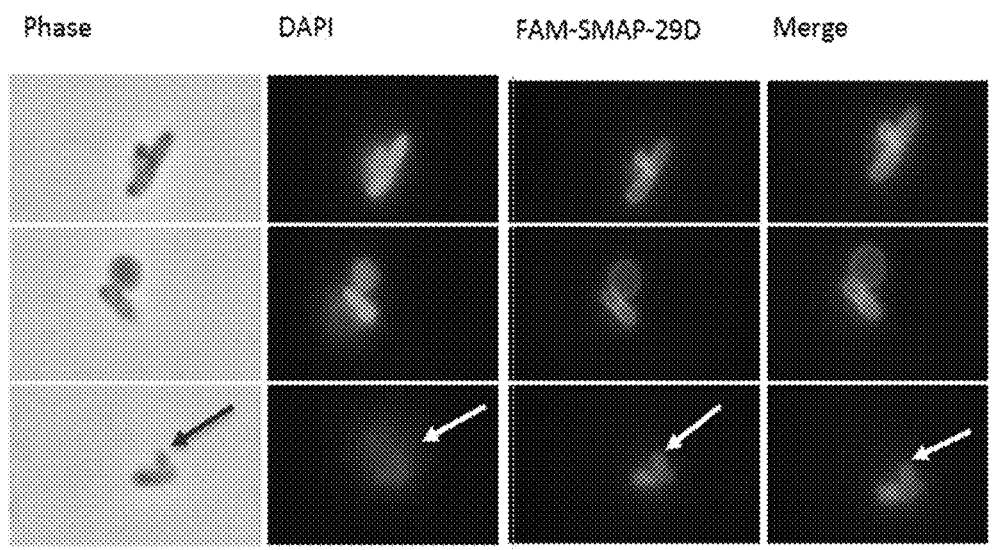

FIG. 11 shows the mechanism of action of the antimicrobial peptides. Phase contrast micrographs shows three representative V. vulnificus cells that were treated for 5 min with 4 µM FAM-labeled SMAP-29D. The DAPI stain is colored blue and the FAM-SMAP-29D green.

Figures 12A, 12B:
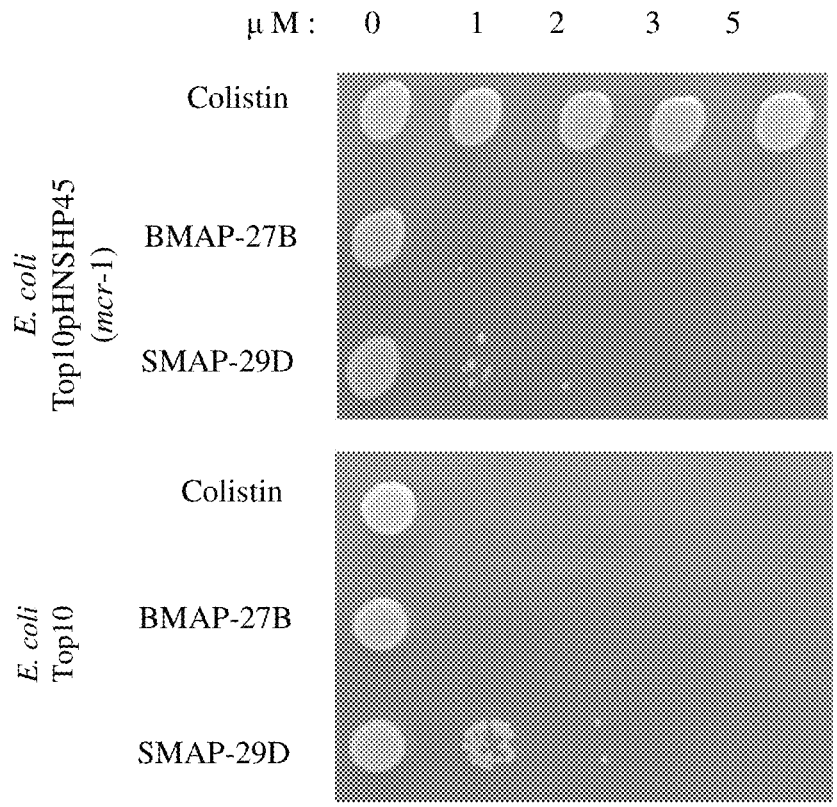

FIGS. 12A-B show BMAP-27B and SMAP-29D can kill colistin-resistant E. coli. FIG. 12A shows colony growth of five Gram-negative bacteria treated with increasing concentrations of BMAP-27B, SMAP-29D, and colistin. $1\times10^5$ CFUs of the bacteria were incubated for 30 min with the concentration of the peptides or colistin shown. Approximately 500 CFUs were then added as a droplet onto non-selective media for 18 h. FIG. 12B shows a quantitative analysis of the viable colonies formed by colistin-resistant bacteria. E. coli Top10/pHNSHP45 or the parental strain Top10 were incubated for 5 with either colistin, BMAP-27B, or SMAP-29D prior to plating to enumerate CFUs on MH agar. The numbers are the means of three independent assays and those in parenthesis are the range for one standard deviation.

FIG. 13 shows an analysis of truncated variants of BMAP-27B for bactericidal activity against E. coli harboring the mcr-1 resistance gene on a plasmid (SEQ ID NOS 12, 18 and 19, respectively, in order of appearance). Each antimicrobial peptide was assayed at a final concentration of 2 µM. The number of viable bacterial colonies were determined by plating on a non-selective media and enumerated. Each result is the average of three independent assays. The fold reduction in the colony forming units (CFU) was calculated by dividing the number of CFUs in the mock-treated sample with the number in the peptide-treated samples.

Figure 14A:
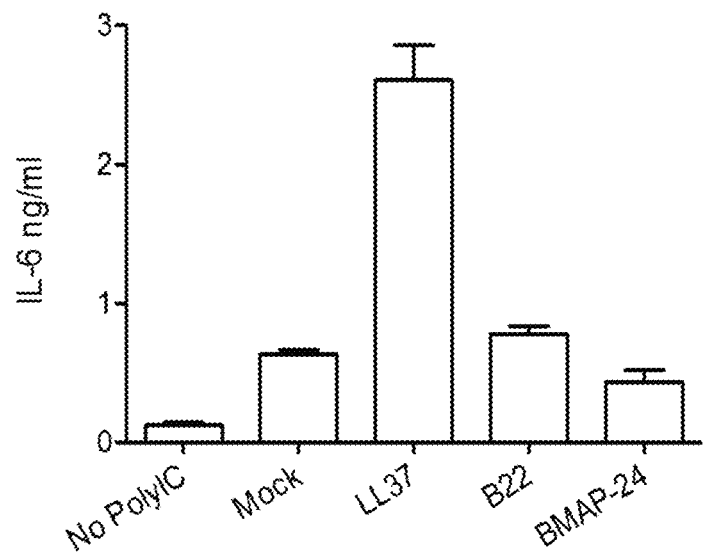
Figure 14B:
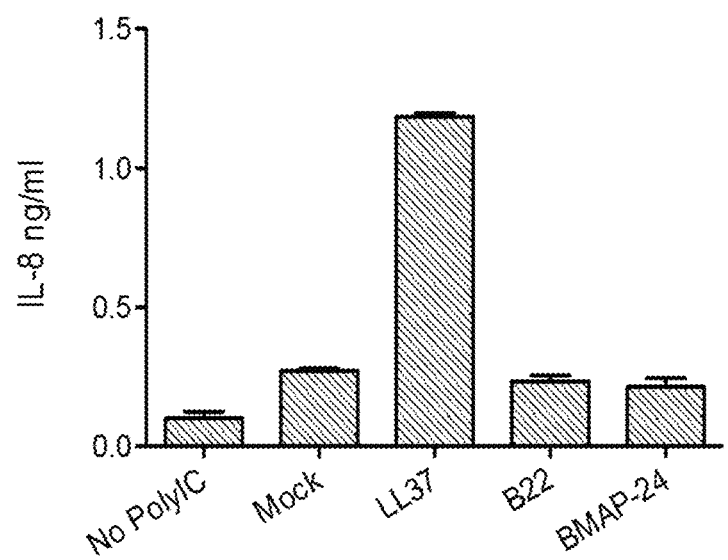

FIGS. 14A-B show that the antimicrobial peptides B22 and BMAP-24 do not enhance the activation of the production of proinflammatory cytokine IL-6 (FIG. 14A) and the proinflammatory cytokine IL-8 (FIG. 14B) through the TLR3 signaling pathway. Lung epithelial BEAS-2B cells were induced with poly(I:C) at 0.1 µg/ml and the amount of IL-6 secreted into the media 20 h later was assessed by ELISA. Where present, the antimicrobial peptide was at a final concentration of 2 µM. Each result represents the mean and standard error of three independent assays.

Figure 15:
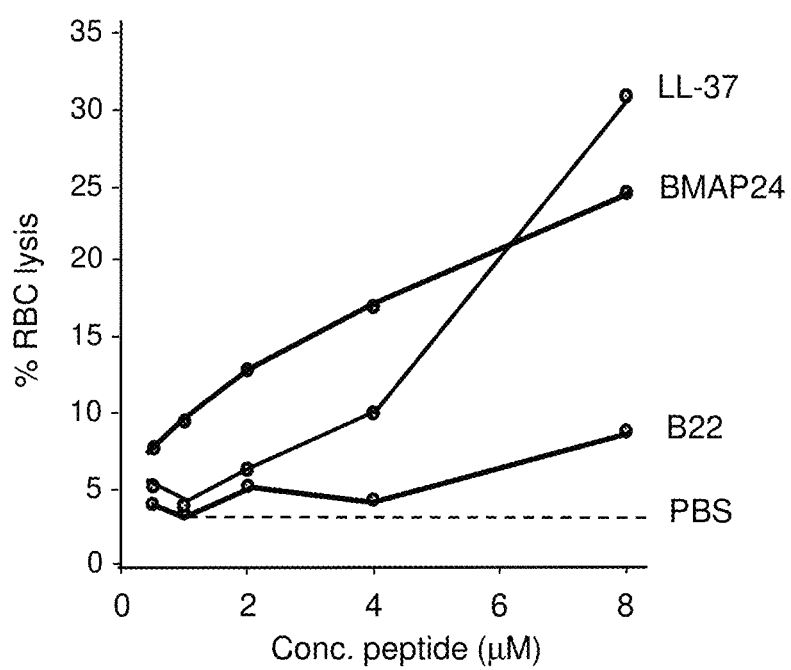

FIG. 15 shows the antimicrobial peptide B22 lyses fewer human red blood cells (hRBCs) and has limited cytotoxicity. The amount of hemoglobin released was measured by the absorbance at 435 nM after a 60-minute incubation with the antimicrobial peptide. The percentage of hRBC lysis was normalized to the amount hemoglobin released by the suspension of the hRBCs in deionized water. The background amount of hRBC lysis was determined by adding phosphate buffered saline (PBS) at the same volume as 8 µM of the peptide to the hRBC for 1 h.

Figure 16:
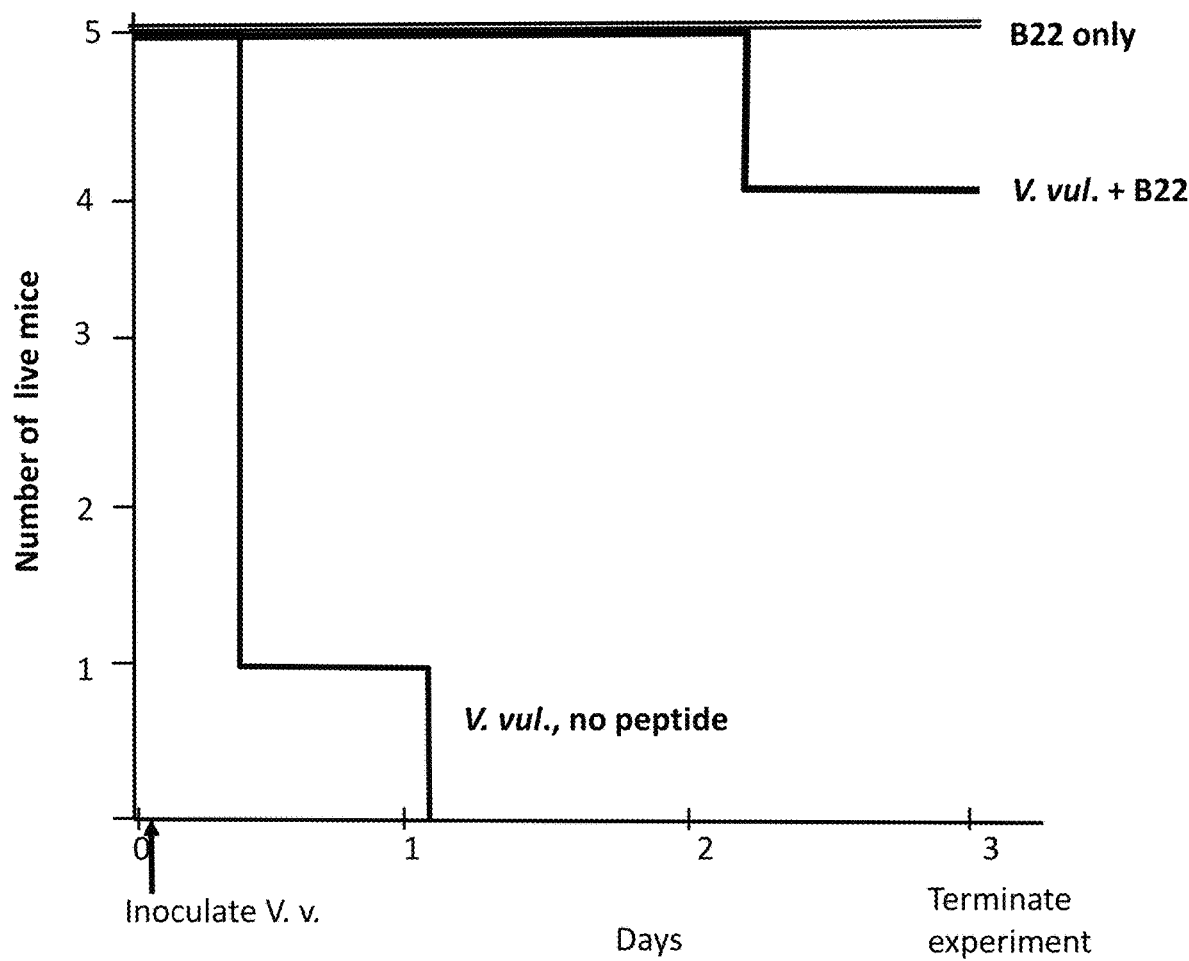

FIG. 16 shows the antimicrobial peptide B22 can reduce the lethal sepsis by Vibrio vulnificus. The number of symptom-less mice in cages of 5 mice were recorded as a function of time. About 50 colony forming units of V. vulnificus were introduced into a surgical incision. The antimicrobial peptide B22 was introduced into the incision at 5 µM 1 h after the introduction of V. vulnificus to the surgical incision.

Figure 17:
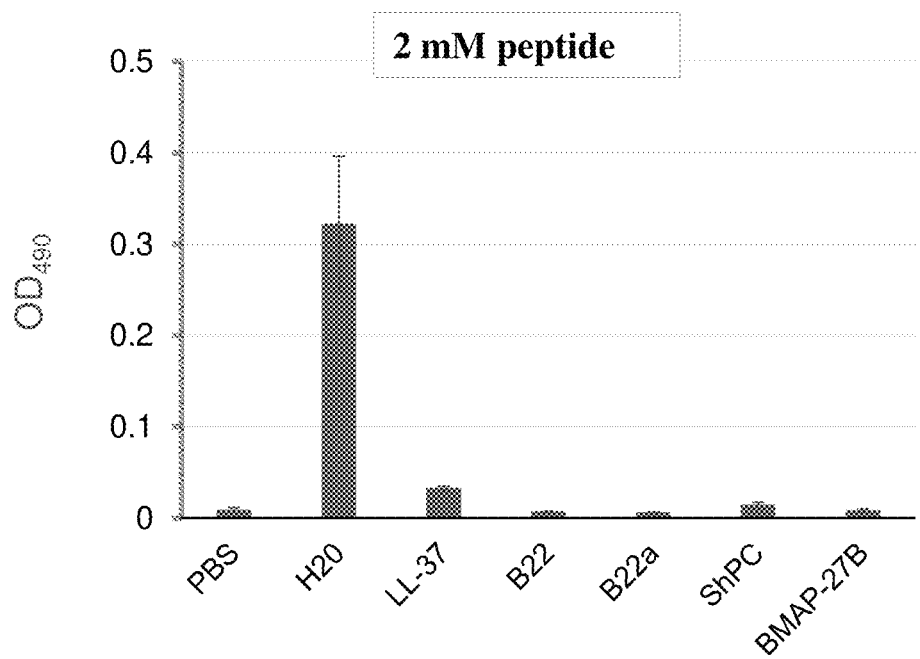

FIG. 17 shows a comparative amount of hemoglobin released by human red blood cells (hRBC) treated with antimicrobial peptides.

Figure 18:
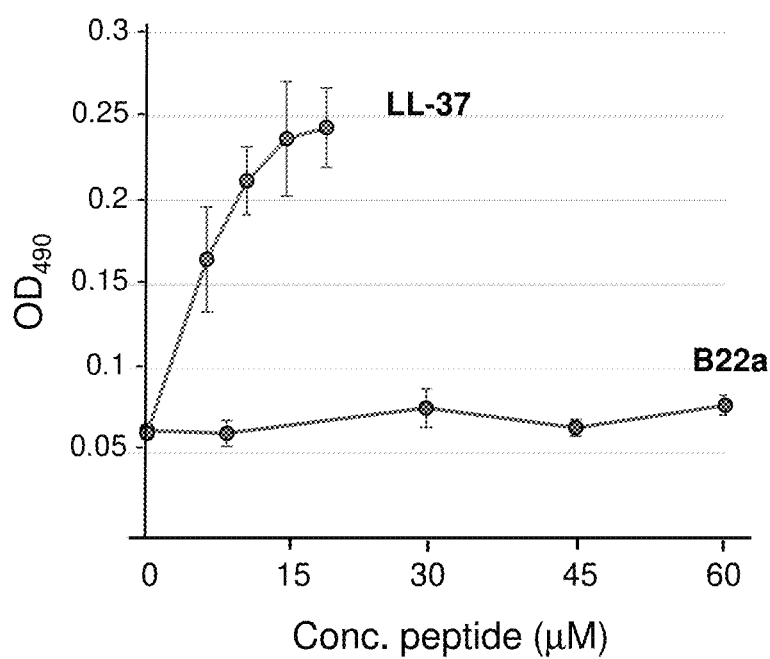

FIG. 18 shows the release of hemoglobin from human red blood cells (hRBC), treated with antimicrobial peptides, as a function of peptide concentration.

Figure 19:
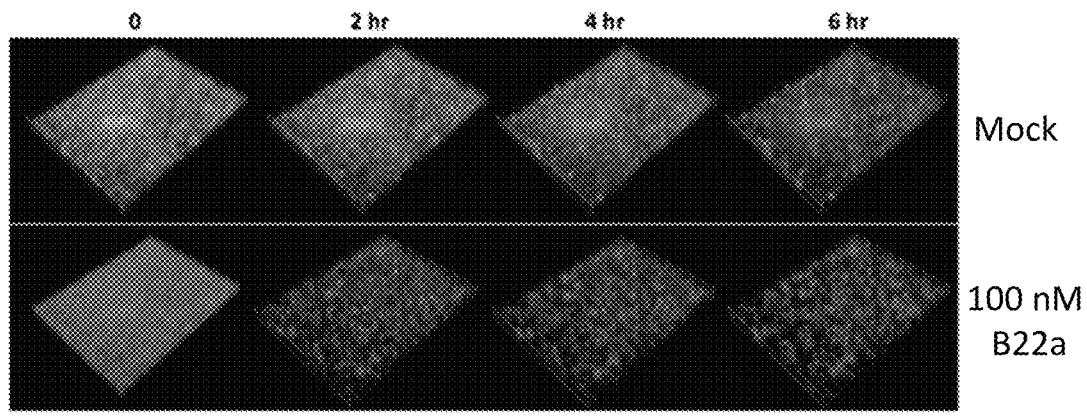

FIG. 19 is time lapse image showing LIVE/DEAD staining at one (1) hour intervals of *V. cholerae* biofilms without (top panels) and following treatment with 100 nM of B22a (bottom row). The amount of death of the *V. cholera* cells in the biofilms increase over time.

Figure 20:
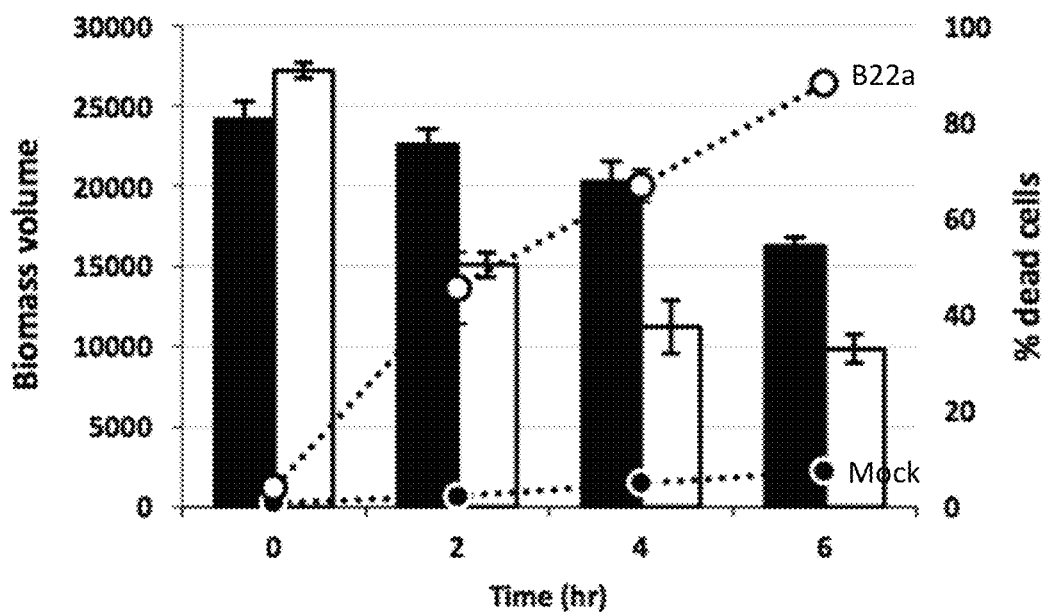

FIG. 20 is a graph showing the quantification of the total biomass for untreated (black bars) and treated (white bars) *V. cholerae* biofilms, and the percentage of dead cells within the *V. cholerae* biofilms (untreated, black circles; treated white circles).

Figure 21:
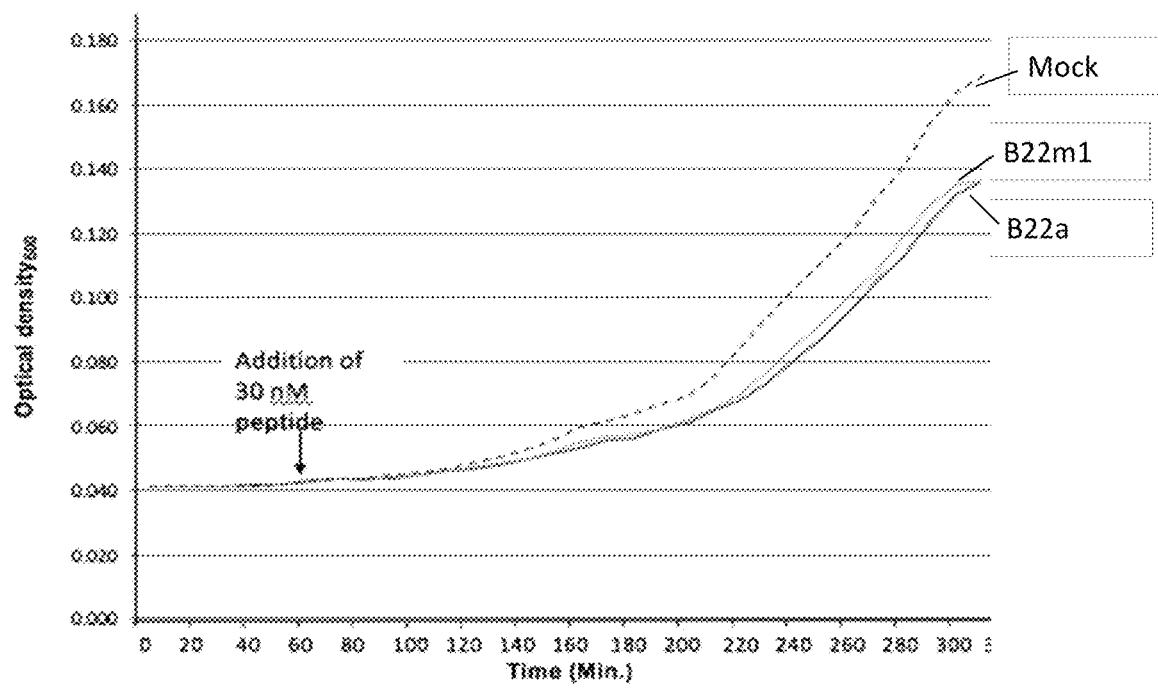

FIG. 21 is a graph showing of peptide B22 (mock), B22a and B22m1 (each at 30 nm) can reduce bacterial growth of *P. aeruginosa*, wherein the bacteria were grown in a plate reader at 37° C. and shaken. Optical density was monitored every ten (10) minutes to track the growth rate.

Figure 22:
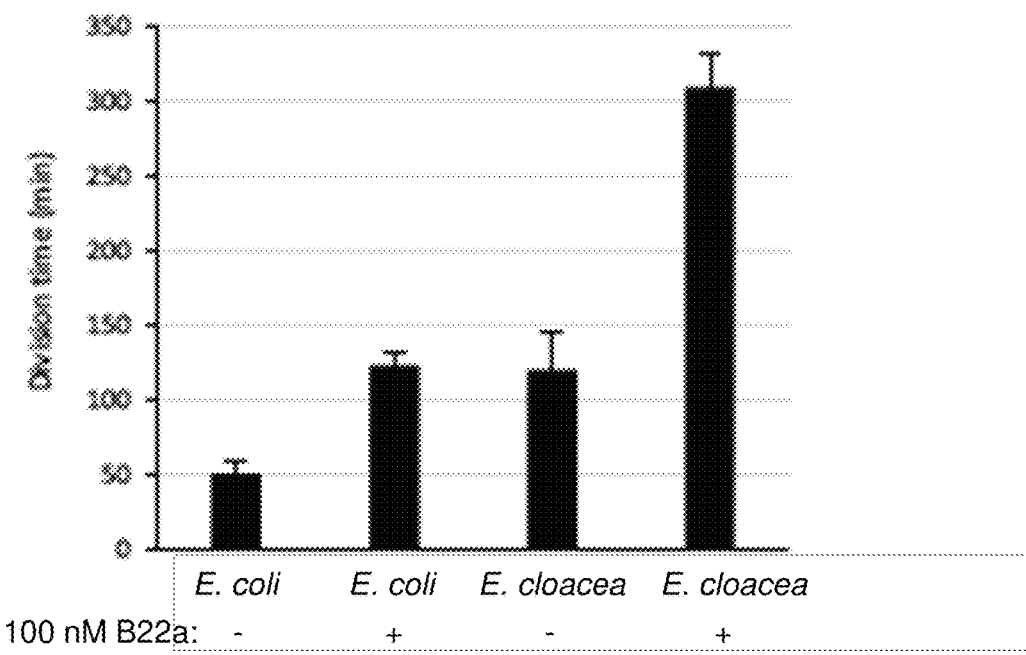

FIG. 22 is a bar graph showing the quantification of cell division time for *E. coli* UTI198 and *Enterobacter cloacae* OC4080 in the presence of 100 nanomolar (nM) B22a, and further showing that B22a increased the cell division time by more than 2-fold.

Figure 23A:
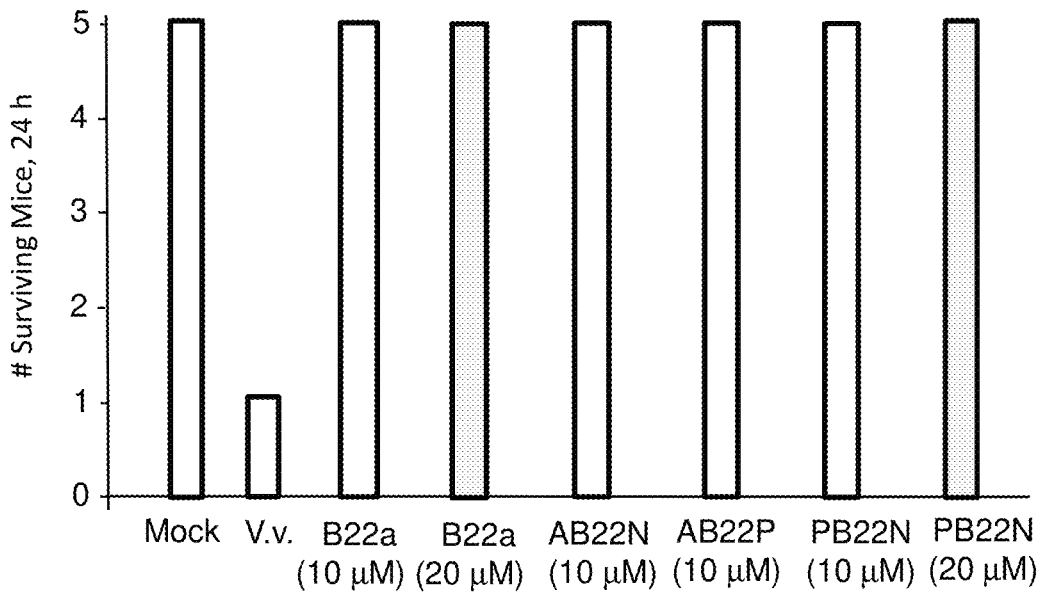
Figure 23B:
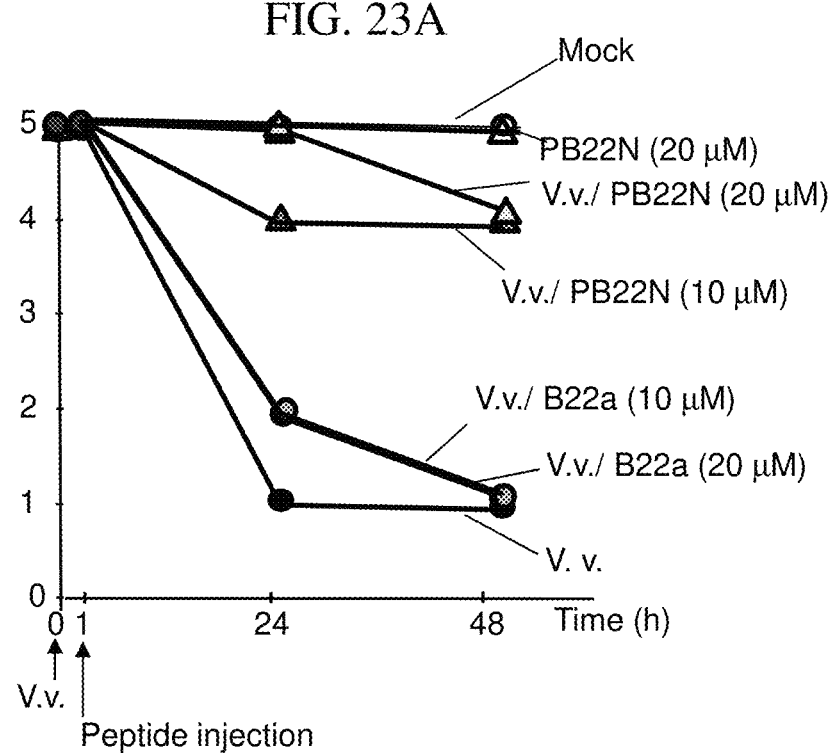

FIGS. 23A, B show the efficacy and toxicity of modified peptides in mice. FIG. 23A shows the effects of modified peptides (AB22N (SEQ ID No: 32); AB22P (SEQ ID No. 33); and PB22N (SEQ ID No: 34)) on mice survival. The survival of mice injected intraperitoneally with iron dextran at 48 h after intraperitoneal injection of 10 or 20 µM of the modified peptides. In all of the injected mice, no obvious symptoms were observed. *Vibrio vulnificus* (*V. v.*) strain CMCP6 was injected at 1×10$^6$ CFU. FIG. 23B shows the survival of mice in an iron-dextran septicemia model. All mice receive iron dextran by intraperitoneal injection. Where indicated, 1 h later 10$^6$ bacterial CFU in 100 µL was injected into the peritoneum (opposite side). 1 h later, 100 µL of the peptide at the indicated concentration was administered on the same side as the bacterial injection.

BRIEF DESCRIPTIONS OF THE SEQUENCES

LL-37
SEQ ID NO: 1
LLGDFFRKSKEKIGKEFKRIVQRIKDFLRNLVPRTES

RL-37
SEQ ID NO: 2
RLGNFFRKVKEKIGGGLKKVGQKIKDFLGNLVPRTAS

CAP-18
SEQ ID NO: 3
GLRKRLRKFRNKIKEKLKKIGQKIQGLLPKLAPRTDY

CRAMP
SEQ ID NO: 4
GLLRKGGEKIGEKLKKIGQKIKNFFQKLVPQPEQ

CAP-11
SEQ ID NO: 5
GLRKKFRKTRKRIQKLGRKIGKTGRKVWKAWREYGQIPYPCRI

SMAP-34
SEQ ID NO: 6
GLFGRLRDSLQRGGQKILEKAERIWCKIKDIFR

BMAP-34
SEQ ID NO: 7
GLFRRLRDSIRRGQQKILEKARRIGERIKDIFRG

PMAP-37
SEQ ID NO: 8
GLLSRLRDFLSDRGRRLGEKIERIGQKIKDLSEFFQS eCATH-3
SEQ ID NO: 9
KRFHSVGSLIQRHQQMIRDKSEATRHGIRIITRPKLLLAS

BMAP-27
SEQ ID NO: 10
GRFKRFRKKFKKLFKKLSPVIPLLHLG

BMAP-27A
SEQ ID NO: 11
GRFKRLRKKFKKLFKKLSPVIPLLHLG

BMAP-27B
SEQ ID NO: 12
GRFKRLRKKLKKLFKKLSPVIPLLHLG

BMAP-27C
SEQ ID NO: 13
GRAKRLRKKLKKLAKKLSPVIPLLHLG

SMAP-29
SEQ ID NO: 14
RGLRRLGRKIAHGVKKYGPTVLRIIRIAG

SMAP-29B
SEQ ID NO: 15
RGLRRLGRKIAHGVKKCGPTVLRIIRIAG

SMAP-29C
SEQ ID NO: 16
RGLRRLGRKIAHGVKKCGPTVLRIIRIAGC

SMAP-29D
SEQ ID NO: 17
RGLRRLGRKIAHGVKKLGPTVLRIIRIAG

BMAP-24
SEQ ID NO: 18
GRFKRFRKKLKKLFKKLSPVIPLL

B22
SEQ ID NO: 19
FRKKLKKLFKKLSPVIPLLKLG

SEQ ID NO: 20
$X_1X_2X_3X_4X_5X_6RKKX_7KKLX_8KKLSPVIPLLX_9X_{10}X_{11}$

SEQ ID NO: 21
$RGLRRLGRKIAHGVKKX_{12}GPTVLRIIRIAGX_{13}$

SEQ ID NO: 22
$X_6RKKX_7KKLX_8KKLSPVIPLLX_9X_{10}X_{11}$

SEQ ID NO: 23
$X_1X_2X_3X_4X_5X_6RKKX_7KKLX_8KKLSPVIPLL$

SEQ ID NO: 24
$X_1X_2X_3X_4X_5X_6RKKX_7KKLX_8KKLSPVIPLLX_9X_{10}X_{11}$

SEQ ID NO: 25
$X_6RKKX_7KKLX_8KKLSPVIPLLX_9X_{10}X_{11}$

SEQ ID NO: 26
$X_1X_2X_3X_4X_5X_6RKKX_7KKLX_8KKLSPVIPLL$

SEQ ID NO: 27
$RGLRRLGRKIAHGVKKX_{12}GPTVLRIIRIAGX_{13}$

B22a
SEQ ID NO: 28
FRKKLKKLFKKLSPVIPLLKLG-NH$_2$

```
B22m1
                                              SEQ ID NO: 29
FRKKLKKLAKKLSPVIPLLKLG-NH2

B22m2
                                              SEQ ID NO: 30
ARKKLKKLAKKLSPVIPLLKLG-NH2

SEQ ID NO: 31
X6RKKX7KKLX8KKLSPVIPLL

AB22a
                                              SEQ ID NO: 32
Acetyl-FRKKLKKLFKKLSPVIPLLKLG-amide AB22P
                                              SEQ ID NO: 33
Acetyl-FRKKLKKLFKKLSPVIPLLKLG-minipolyethylene glycol PB22N
                                              SEQ ID NO: 34
minipolyethylene glycol-PRKKLKKLFKKLSPVIPLLKLGamide
```

DETAILED DESCRIPTION

Unless defined otherwise, the scientific and technology nomenclatures have the same meaning as commonly understood by a person of ordinary skill in the art pertaining to this disclosure.

In some embodiments, an antimicrobial peptide comprises an amino acid sequence of $X_1X_2X_3X_4X_5X_6RKKX_7KKLX_8KKLSPVIPLLX_9X_{10}X_{11}$ (SEQ ID NO: 20), wherein $X_1$ is a non-polar amino acid or absent, $X_2$ is a basic amino acid or absent, $X_3$ is a non-polar amino acid or absent, $X_4$ is a basic amino acid or absent, $X_5$ is a basic amino acid or absent, $X_6$ is a non-polar amino acid, $X_7$ is a non-polar amino acid, $X_8$ is a non-polar amino acid, $X_9$ is a basic amino acid or absent, $X_{10}$ is a non-polar amino acid or absent, and $X_{11}$ is a non-polar amino acid or absent; or a pharmaceutically acceptable salt thereof. In some embodiments, the peptide may comprise as C-terminal modification. In some embodiments, the peptide may be C-terminally amidated. In some embodiments, the peptide may comprise an N-terminal modification.

In some embodiments, an antimicrobial peptide comprises an amino acid sequence of $X_1X_2X_3X_4X_5X_6RKKX_7KKLX_8KKLSPVIPLLX_9X_{10}X_{11}$ (SEQ ID NO: 24), wherein $X_1$ is G or absent, $X_2$ is R or absent, $X_3$ is F, A, or absent, $X_4$ is K or absent, $X_5$ is R or absent, $X_6$ is F or L, $X_7$ is F or L, $X_8$ is F or A, $X_9$ is H, K, or absent, $X_{10}$ is L or absent, and $X_{11}$ is G or absent, provided that when $X_7$ is F, $X_6$ is L; or a pharmaceutically salt thereof. In some embodiments, the peptide may comprise as C-terminal modification. In some embodiments, the peptide may be C-terminally amidated. In some embodiments, the peptide may comprise an N-terminal modification.

In some embodiments, an antimicrobial peptide comprises an amino acid sequence of $X_6RKKX_7KKLX_8KKLSPVIPLLX_9X_{10}X_{11}$ (SEQ ID NO: 22), wherein $X_6$ is a non-polar amino acid, $X_7$ is a non-polar amino acid, $X_8$ is a non-polar amino acid, $X_9$ is a basic amino acid, $X_{10}$ is a non-polar amino acid, and $X_{11}$ is a non-polar amino acid; or a pharmaceutically acceptable salt thereof. In some embodiments, the peptide may comprise as C-terminal modification. In some embodiments, the peptide may be C-terminally amidated. In some embodiments, the peptide may comprise an N-terminal modification.

In some embodiments, an antimicrobial peptide comprises an amino acid sequence of $X_6RKKX_7KKLX_8KKLSPVIPLLX_9X_{10}X_{11}$ (SEQ ID NO: 25), wherein $X_6$ is F or L, $X_7$ is F or L, $X_8$ is F or A, $X_9$ is H or K, $X_{10}$ is L, and $X_{11}$ is G, provided that when $X_7$ is F, $X_6$ is L; or a pharmaceutically salt thereof. In some embodiments, the peptide may comprise as C-terminal modification. In some embodiments, the peptide may be C-terminally amidated. In some embodiments, the peptide may comprise an N-terminal modification.

In some embodiments, an antimicrobial peptide comprises an amino acid sequence of $X_1X_2X_3X_4X_5X_6RKKX_7KKLX_8KKLSPVIPLL$ (SEQ ID NO: 23), wherein $X_1$ is a non-polar amino acid, $X_2$ is a basic amino acid, $X_3$ is a non-polar amino acid, $X_4$ is a basic amino acid, $X_5$ is a basic amino acid, $X_6$ is a non-polar amino acid, $X_7$ is a non-polar amino acid, and $X_8$ is a non-polar amino acid; or a pharmaceutically acceptable salt thereof. In some embodiments, the peptide may comprise as C-terminal modification. In some embodiments, the peptide may be C-terminally amidated. In some embodiments, the peptide may comprise an N-terminal modification.

In some embodiments, an antimicrobial peptide comprises an amino acid sequence of $X_1X_2X_3X_4X_5X_6RKKX_7KKLX_8KKLSPVIPLL$ (SEQ ID NO: 26), wherein $X_1$ is G, $X_2$ is R, $X_3$ is F or A, $X_4$ is K, $X_5$ is R, $X_6$ is F or L, $X_7$ is F or L, and $X_8$ is F or A, provided that when $X_7$ is F, $X_6$ is L; or a pharmaceutically salt thereof. In some embodiments, the peptide may comprise as C-terminal modification. In some embodiments, the peptide may be C-terminally amidated. In some embodiments, the peptide may comprise an N-terminal acetyl group.

In some embodiments, an antimicrobial peptide comprises an amino acid sequence of RGLRRLGRKIAHGVKKX$_{12}$GPTVLRIIRIAGX$_{13}$ (SEQ ID NO: 21), wherein $X_{12}$ is a polar amino acid or a non-polar amino acid and $X_{13}$ is a polar amino acid or absent; or a pharmaceutically acceptable salt thereof. In some embodiments, the peptide may comprise as C-terminal modification. In some embodiments, the peptide may be C-terminally amidated. In some embodiments, the peptide may comprise an N-terminal acetyl group.

In some embodiments, an antimicrobial peptide comprises an amino acid sequence of RGLRRLGRKIAHGVKKX$_{12}$GPTVLRIIRIAGX$_{13}$ (SEQ ID NO: 27), wherein $X_{12}$ is Y, C, or L and $X_{13}$ is C or absent, provided that when $X_{12}$ is Y, $X_{13}$ is C; or a pharmaceutically acceptable salt thereof. In some embodiments, the peptide may comprise as C-terminal modification. In some embodiments, the peptide may be C-terminally amidated. In some embodiments, the peptide may comprise an N-terminal acetyl group.

In some embodiments, an antimicrobial peptide comprises an amino acid sequence selected from the group consisting of SEQ ID NO: 11, SEQ ID NO: 12, SEQ ID NO: 13, SEQ ID NO: 15, SEQ ID NO: 16, SEQ ID NO: 17, SEQ ID NO: 18, SEQ ID NO: 19, and a combination thereof. In some embodiments, the peptide may comprise as C-terminal modification. In some embodiments, the peptide may be C-terminally amidated. In some embodiments, the peptide may comprise an N-terminal acetyl group.

Cathelicidin-related antimicrobial peptides are a family of peptides produced by macrophages and polymorphonuclear leukocytes (PMNs), and epithelial cells such as keratinocytes. cathelicidins serve a critical role in mammalian innate immune defense against invasive bacterial infection. The peptides of cathelicidin family are classified as antimicrobial peptides.

Antimicrobial peptides are produced by organisms in all three kingdoms of life on earth to decrease the establishment of other microbes. Cathelicidins are a class of peptides typically of ~25-40 amino acids in length that have a high frequency of basic amino acids. They interact with the membranes of susceptible bacteria, form higher order structures to cause leakage of ions and the death of the bacteria. Cathelicidins could also bind bacterial cell wall materials, including lipopolysaccharide (LPS) molecules that are potent inducers of the inflammatory responses. These properties have made antimicrobial peptides attractive molecules to replace antibiotics.

LL-37 is the only cathelicidin antimicrobial peptide produced by humans. The 37-residue LL-37 is generated by proteolytic cleavage of the C-terminal portion of the hCAP-18 protein. As is the case with antimicrobial peptides, LL-37 has a large array of biological activities. For example, in addition to suppressing bacterial infection and suppressing the pro-inflammatory responses, LL-37 can promote wound healing and decreasing fibrosis.

Cathelicidin peptides have been isolated from many different species of mammals, including but not limited to humans, monkeys, mice, rats, rabbits, guinea pigs, pandas, pigs, cattle, frogs, sheep, goats, chickens, and horses. Some species produce more than one Cathelicidins. Illustratively, cathelicidins are enriched for positively-charged amino acids, but the sequences for the cathelicidins produced by different animals vary.

Currently identified cathelicidins include but not limited to the following:
  Human: hCAP-18/LL-37
  Rhesus Monkey: RL-37
  Mice: CRAMP, (Cathelicidin-related Antimicrobial Peptide)
  Rats: rCRAMP
  Rabbits: CAP-18
  Guinea Pig: CAP-11
  Pigs: PR-39, Prophenin, PMAP-23,36,37
  Cattle: BMAP-27,28,34 (Bovine Myeloid Antimicrobial Peptides); Bac5, Bac7
  Horses: eCATH-1, eCATH-2, eCATH-3
  Frogs: cathelicidin-AL (found in *Amolops loloensis*)
  Sheep: SMAP-29
  Chickens: Four cathelicidins, fowlicidins 1,2,3 and cathelicidin Beta-1

Previous studies have shown a consensus of how to engineer some of the known peptides in nature into a more potent bacteria-killing agent, yet reduce the human cell toxicity caused by their respective natural products. A detailed description and list of such engineered peptides are found in the PCT International Application No. PCT/US16/63612, filed on Nov. 23, 2016, the disclosure of which is hereby incorporated by reference in its entirety.

*Vibrio* is a genus of Gram-negative bacteria, possessing a curved-rod shape (comma shape), several species of which can cause foodborne infection, usually associated with eating undercooked seafood.

Several species of *Vibrio* are human pathogens. Most disease-causing strains are associated with gastroenteritis, but can also infect open wounds and cause septicemia. They can be carried by numerous marine animals, such as crabs or prawns, and have been known to cause fatal infections in humans during exposure. Pathogenic *Vibrio* species include *V. cholerae* (the causative agent of cholera), *V. parahaemolyticus*, and *V. vulnificus*. *V. cholerae* is generally transmitted by contaminated water. Pathogenic *Vibrio* species can cause foodborne illness (infection), usually associated with eating undercooked seafood. The pathogenic features can be linked to quorum sensing where bacteria are able to express their virulence factor via their signaling molecules.

Foodborne *Vibrio* infections are most often associated with eating raw shellfish. *V. vulnificus* is an extremely virulent pathogen found in marine environments. *V. vulnificus* outbreaks commonly occur in warm climates and small, generally lethal, outbreaks occur regularly. An outbreak occurred in New Orleans after Hurricane Katrina, and several lethal cases occur most years in Florida. *V. vulnificus* can cause gastroenteritis when ingested in oysters, septicemia in undercooked shellfish, and necrotic wounds are found with 25% mortality, 50% with septicemia.

Currently, infection with *V. vulnificus* is treated with antibiotics such as Cephalosporin and a Tetracycline (Ceftriaxone and doxycycline).

*V. parahaemolyticusis* also associated with the Kanagawa phenomenon, in which strains isolated from human hosts (clinical isolates) are hemolytic on blood agar plates, while those isolated from nonhuman sources are not hemolytic.

Many *Vibrio* species are also zoonotic. Illustratively, many *Vibrio* can cause disease in fish and shellfish and are common causes of mortality among domestic marine life.

Several antimicrobial peptides have been identified and tested as described herein. Antimicrobial peptides in accordance with the present disclosure are efficient at killing a number of foodborne Gram-negative bacteria. In some embodiments, the Gram-negative bacteria are particularly those found in the *Vibrio* genus. In some embodiments, the antimicrobial peptide has reduced cytotoxicity for human cells. For example, a low concentration of an antimicrobial peptide in accordance with the present disclosure is required to kill effectively various Gram-negative bacteria. When selective peptides such as the SMAP-29 variants or the BMAP-27 variants are tested for their bacterial killing effects, the colony forming units for various Gram-negative bacteria, including *E. cloacae* 4080, *E. coli* IU 342, *K. pneumonia* 8893, and *K. pneumoniae* C-2 were reduced dramatically within minutes of the antimicrobial peptide application. The fold change can be from hundreds to thousands folds reduction (See FIGS. 6A-B). Further, various *vibrio* species are highly sensitive to these selective peptides, such as SMAP-29 variants and BMAP-27 variants. In some embodiments, SMAP-29D and BMAP-27B efficiently kill *V. angustum*, *V. fischeri*, and *V. vulnificus* as shown in FIGS. 8-11.

Figure 1A:
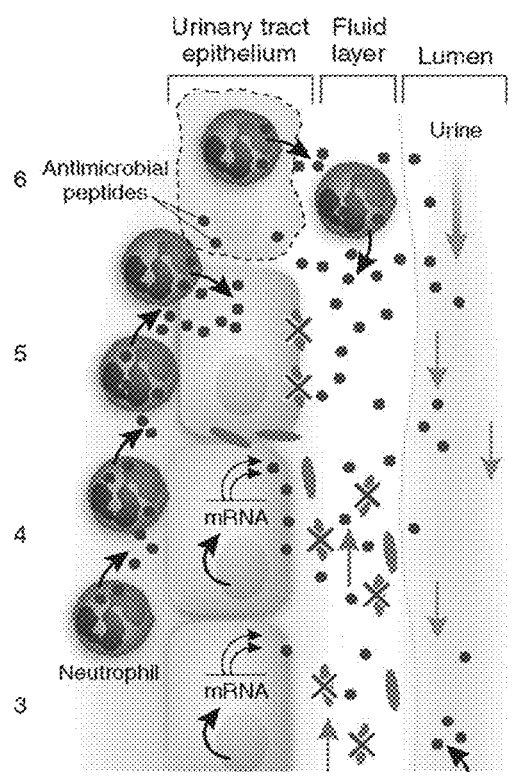
Figure 1B:
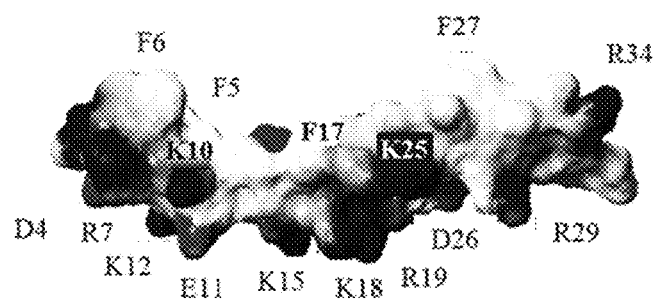
Figure 1C:
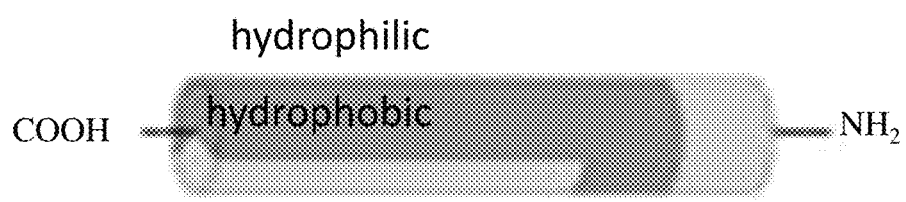
Figure 2A:
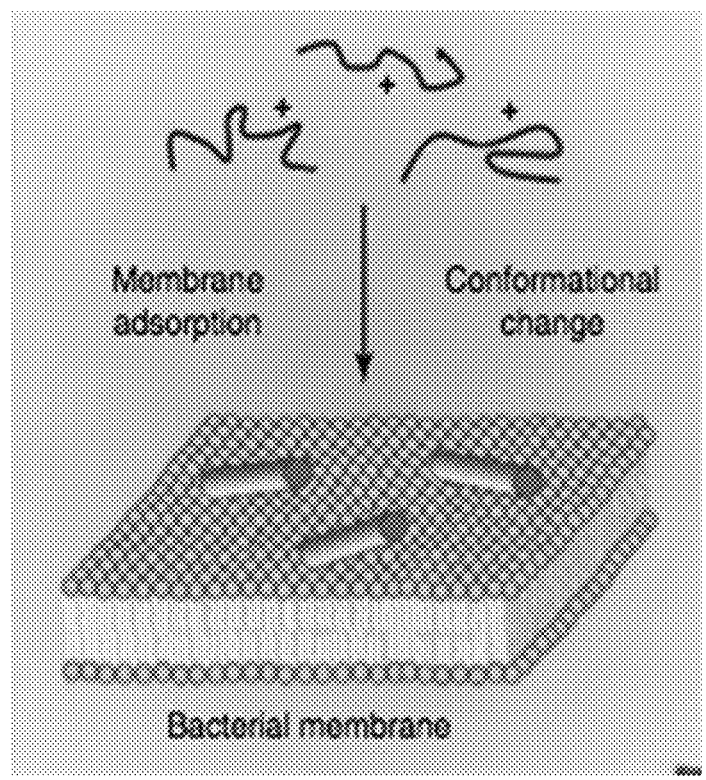
Figure 2B:
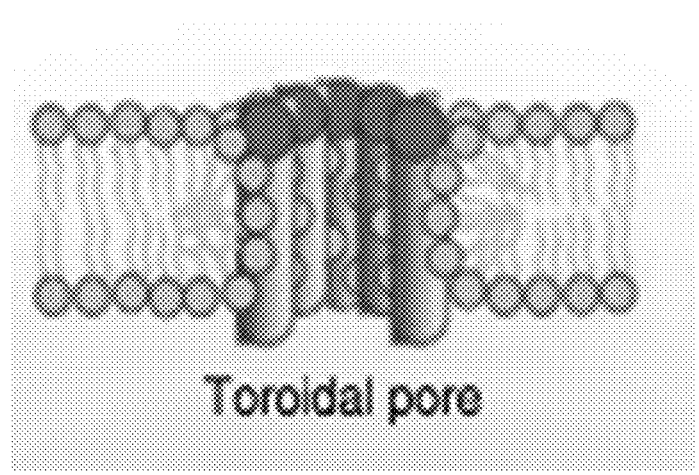
Figure 2C:
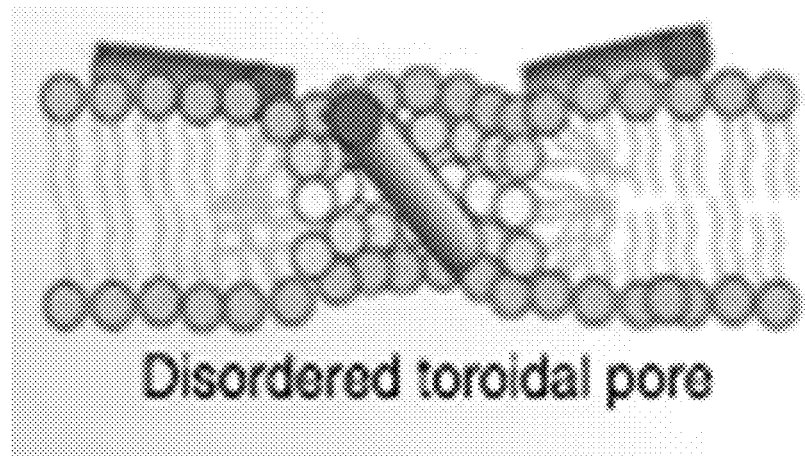
Figure 2D:
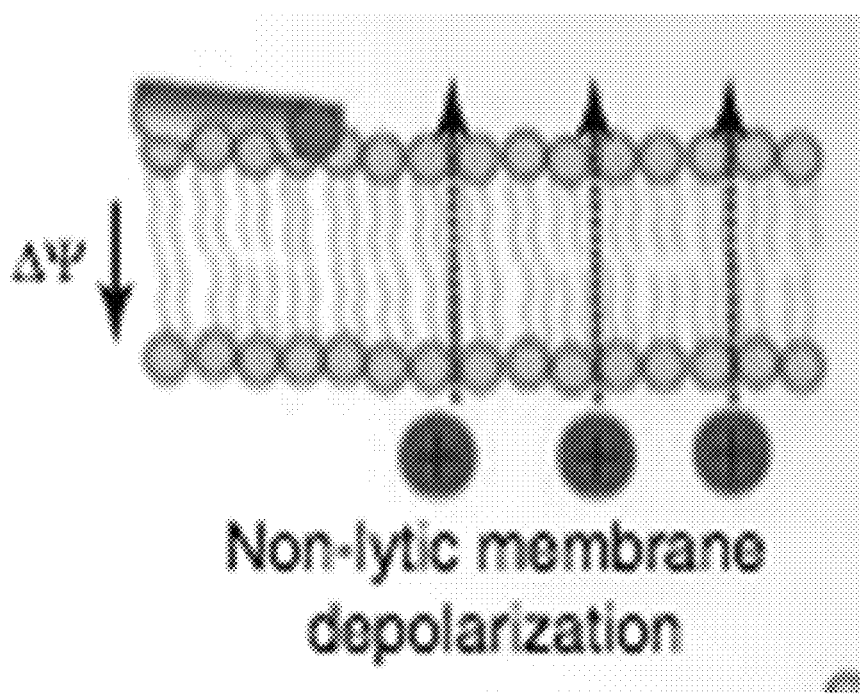
Figure 4D:
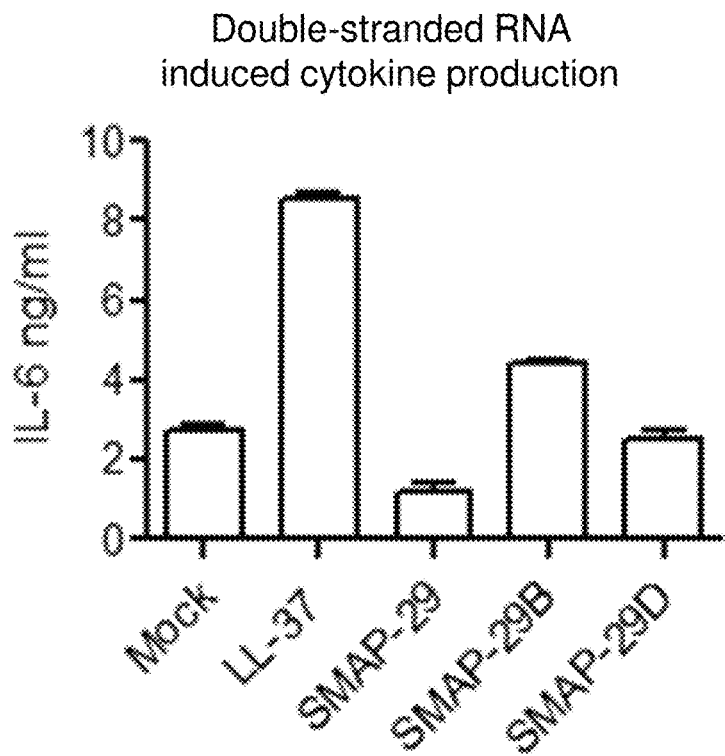
Figure 4E:
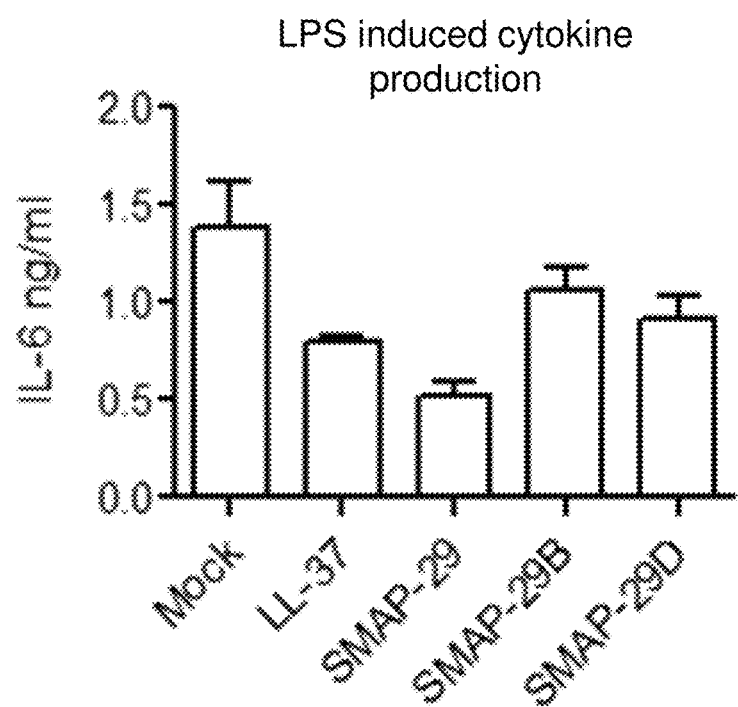
Figure 5D:
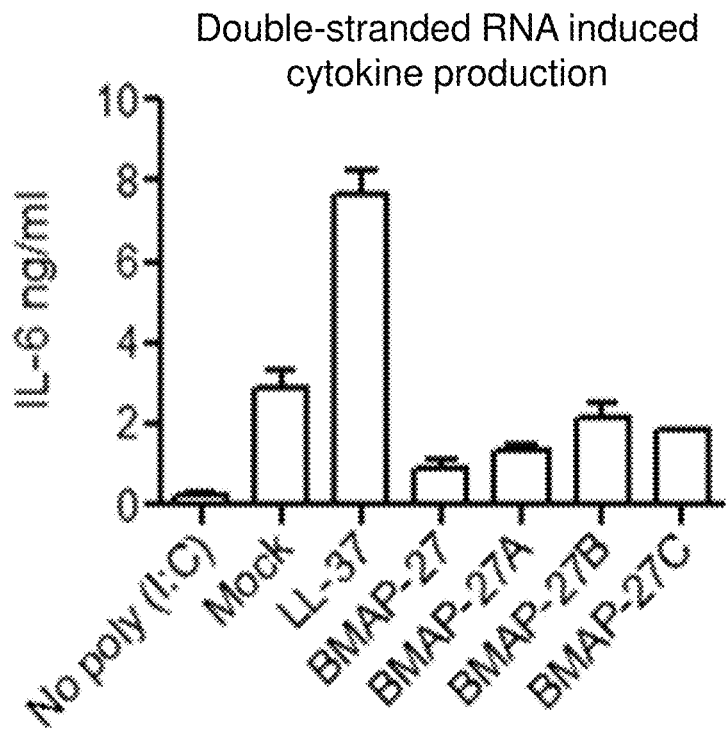
Figure 5E:
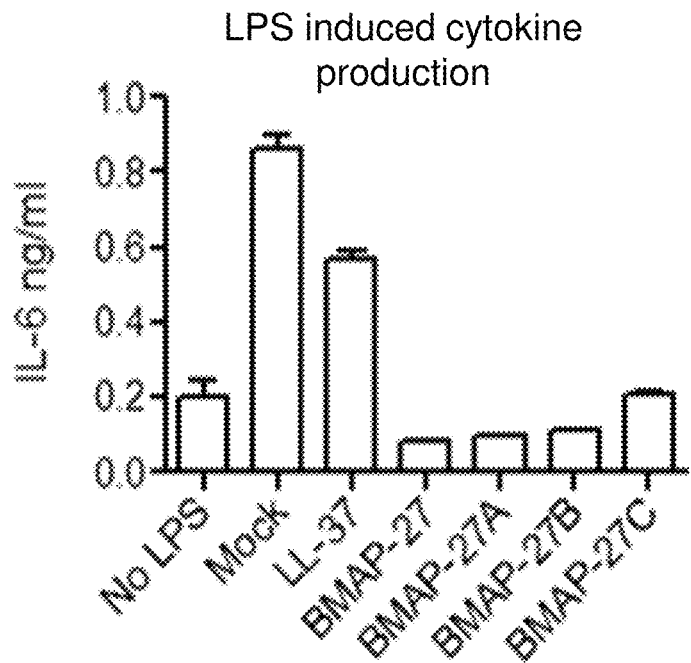

In some embodiments, antimicrobial peptides in accordance with the present have reduced cytotoxicity to human cells. In some embodiments, the induction of red blood cell lysis is decreased compared to other similar peptides, such as LL-37. In some embodiments, the TLR3/FLPR-1 mediated autoimmune response is reduced when IL-6 production was assessed in the presence of double-stranded RNA and these peptides. In some embodiments, toxin-related inflammation is inhibited by the presence of these selective antimicrobial peptides. In some embodiments, the cell metabolism rate in the presence and absence of these antimicrobial peptides are not distinguishable, as shown for example, in FIGS. 4C and 5C.

As one skilled in the art will appreciate, in some embodiments the antimicrobial peptides are degradable to become non-toxic amino acids. It is contemplated that these antimicrobial peptides can be used to treat raw seafood that is infected by a Gram-negative bacterium.

In some embodiments, the antimicrobial peptides may be used to treat aquaculture. As the effective killer of the fish pathogen *Vibrios*, these antimicrobial peptides can also be used in the fish pond to prevent or cure infections in farm-raised fish or shellfish, etc. One advantage of such use is that the peptides do not need to be removed after the treatment since it can be degraded into non-toxic amino acid. Thus, the application of these identified antimicrobial peptides (or the variants thereof that possess the similar bacterial killing effect) can become a useful tool in the food processing industry. For example, *Vibrios* associated with uncooked shellfish and fish have had particularly significant consequences on foodborne illness. The peptides produced in this disclosure can be used to decrease the bacterial load and render uncooked shellfish and fish safer for consumption.

In some embodiments, antimicrobial peptides in accordance with the present disclosure can be used to treat farm-harvested or wild-caught seafood. Illustratively, the seafood may be a fish or a shellfish. Illustrative shellfish include crabs, prawns, oysters, and clams.

In some embodiments, antimicrobial peptides in accordance with the present disclosure can be used to treat an infection in a subject. In some embodiments, the infection is in a wound. In some embodiments, the infected wound may be treated by contacting the infected wound with a composition comprising an antimicrobial peptide or a pharmaceutically acceptable salt thereof.

As described herein, the antimicrobial peptides and variants thereof kill Gram-negative bacteria within minutes and effectively (with several orders of magnitude reduction in viable bacterial numbers). The mechanism of action is likely due to perforation of the bacterial membrane. The reduction in viable bacterial number will decrease the infection of the aquaculture product and potential consumers of the aquaculture product. Application of these anti-microbial peptides in seafood preparation and aquafarming is contemplated within this disclosure.

Antimicrobial peptides and variants thereof may comprise polar amino acids. In some embodiments, polar amino acids are selected from the group consisting of asparagine (Asn, N), cysteine (Cys, C), glutamine (Gln, Q), serine (Ser, S), threonine (Thr, T), and tyrosine (Tyr, Y). It should be understood that acceptable polar amino acid variants include D-amino acids, peptoids, synthetic peptides, and any suitable alternative thereof.

Antimicrobial peptides and variants thereof may comprise non-polar amino acids. In some embodiments, the non-polar amino acids are selected from the group consisting of alanine (Ala, A), glycine (Gly, G), isoleucine (Ile, I), leucine (Leu, L), methionine (Met, M), phenylalanine (Phe, F), proline (Pro, P), tryptophan (Trp, W), and valine (Val, V). It should be understood that acceptable non-polar amino acid variants include D-amino acids, peptoids, synthetic peptides, and any suitable alternative thereof.

Antimicrobial peptides and variants thereof may comprise basic amino acids. In some embodiments, the basic amino acids are selected from the group consisting of arginine (Arg, R), lysine (Lys, K), and histidine (His, H). In some embodiments, the basic amino acids comprise functional groups capable of being positively charged at physiological pH. Representative basic functional groups include amines, guanidines, and heteroaromatic rings capable of being ionized at physiological pH. It should be understood that acceptable basic amino acid variants include D-amino acids, peptoids, synthetic peptides, and any suitable alternative thereof.

Antimicrobial peptides and variants thereof may comprise acidic amino acids. In some embodiments, acidic amino acids are selected from aspartic acid (Asp, D) glutamic acid (Glu, E), and derivatives thereof. In some embodiments, acidic amino acids comprise carboxylates or any other common functional group that is negatively charged at physiological pH. It should be understood that acceptable acidic amino acid variants include D-amino acids, peptoids, synthetic peptides, and any suitable alternative thereof.

Antimicrobial peptides may comprise modified or substituted residues. In some embodiments, the antimicrobial peptide may comprise a C-terminal modification, an N-terminal modification, or both. In some embodiments, the C-terminal modification is a C-terminal amidation such as $C(O)NH_2$ as opposed to the carboxylic acid $C(O)OH$.

In some embodiments, the antimicrobial peptide comprises C-terminal modification such as a C-terminal amide. Illustratively, a C-terminal amide may be represented in a formula as $Xaa-NH_2$, where Xaa is any amino acid, unnatural amino acid, or derivative thereof. In some embodiments, if the antimicrobial peptide has a C-terminal glycine, the C-terminal amidation may be represented as $G-NH_2$.

In some embodiments, the C-terminus of the peptide is substituted to form (peptide)-C(O)R, wherein R is a $-OR^A$, $-NR^AR^B$, $C_{1-18}$ alkyl, or $C_{1-18}$ heteroalkyl, wherein each $R^A$ and $R^B$ is individually H, $C_{1-18}$ alkyl, $C_{1-18}$ heteroalkyl, or polyethylene glycol (PEG), wherein each hydrogen atom on $C_{1-18}$ alkyl or $C_{1-18}$ heteroalkyl is optionally substituted with halo, hydroxy, or amino, provided that when R is $OR^A$, $R^A$ is not H. In some embodiments, $C_{1-18}$ alkyl includes methyl, ethyl, and straight chained or branched propyl, butyl, pentyl, hexyl, or heptyl. In some embodiments $C_{1-18}$ alkyl is methyl. In some embodiments, $C_{1-18}$ heteroalkyl is a PEG. In some embodiments, $C_{1-18}$ heteroalkyl is 8-amino 3,6-dioxaoctanyl.

In some embodiments, the N-terminus of the peptide is substituted to form RC(O)N(H)-peptide, wherein R is a $-OR^A$, $-NR^AR^B$, $C_{1-18}$ alkyl, or $C_{1-18}$ heteroalkyl, wherein each $R^A$ and $R^B$ is individually H, $C_{1-18}$ alkyl, or $C_{1-18}$ heteroalkyl, wherein each hydrogen atom on $C_{1-18}$ alkyl or $C_{1-18}$ heteroalkyl is optionally substituted with halo, hydroxy, or amino. In some embodiments, $C_{1-18}$ alkyl includes methyl, ethyl, and straight chained or branched propyl, butyl, pentyl, hexyl, or heptyl. In some embodiments $C_{1-18}$ alkyl is methyl. In some embodiments, $C_{1-18}$ heteroalkyl is a PEG. In some embodiments, $C_{1-18}$ heteroalkyl is 8-amino 3,6-dioxaoctanyl.

In some embodiments, the antimicrobial peptide is configured to minimize the formation of higher order structures. Illustratively, the antimicrobial peptide may be configured so that formation of multi-subunit structures or oligomers are minimized Illustratively, substituting a hydrophobic aromatic amino acid for a hydrophobic aliphatic amino acid or alanine may be a way to minimize the formation of multi-subunit structures or oligomers. In some embodiments, an antimicrobial peptide may have 1, 2, or 3 phenylalanines replaced with alanines. In some embodiments, minimizing the formation of a higher order structure or oligomers may allow the antimicrobial peptide to be effective at lower concentrations.

In some embodiments, peptides, sometimes called antimicrobial peptides, kill Gram-negative bacteria. In some embodiments, the Gram-negative bacteria are selected from the group consisting of *Vibrios* genus, an *Escherichia coli*, an *Enterobacter cloacae*, a *Klebsiella pneumoniae*, a *Serratia marcescens*, a *Pseudomonas aeruginosa*, and a mixture thereof. In some embodiments, the Gram-negative bacteria are selected from the group consisting of *Vibrios* genus, an *Escherichia coli*, a *Klebsiella pneumoniae*, a *Pseudomonas aeruginosa*, and a mixture thereof. In some embodiments, the Gram-negative bacteria is from the *Vibrios* genus. In some embodiments, the Gram-negative bacteria is an *Escherichia coli*. In some embodiments, the Gram-negative bacteria is an *Enterobacter cloacae*. In some embodiments, the Gram-negative bacteria is an *Enterococcus faecalis*. In some embodiments, the Gram-negative bacteria is a *Klebsiella pneumoniae*. In some embodiments, the Gram-negative bacteria is a *Serratia marcescens*. In some embodiments, the Gram-negative bacteria is a *Pseudomonas aeruginosa*.

In some embodiments, the *Vibrios* is selected from the group consisting of *V. parahaemolyticus, V. vulnificus, V. fischeri.* and *V. harveyi*. In some embodiments, the *Vibrios* is selected from the group consisting of *V. parahaemolyticus, V. vulnificus,* and *V. fischeri*. In some embodiments, the *Vibrios* is *V. parahaemolyticus*. In some embodiments, the *Vibrios* is *V. vulnificus*. In some embodiments, the *Vibrios* is *V. fischeri*. In some embodiments, the *Vibrios* is *V. harveyi*.

In other embodiments of the methods described herein, pharmaceutically acceptable salts of the compositions described herein are provided. Pharmaceutically acceptable salts of compositions described herein include acid addition and base salts thereof.

Suitable acid addition salts of the compositions described herein are formed from acids which form non-toxic salts. Illustrative examples include the acetate, aspartate, benzoate, besylate, bicarbonate/carbonate, bisulphate/sulphate, borate, camsylate, citrate, edisylate, esylate, formate, fumarate, gluceptate, gluconate, glucuronate, hexafluorophosphate, hibenzate, hydrochloride/chloride, hydrobromide/bromide, hydroiodide/iodide, isethionate, lactate, malate, maleate, malonate, mesylate, methylsulphate, naphthylate, 2-napsylate, nicotinate, nitrate, orotate, oxalate, palmitate, pamoate, phosphate/hydrogen phosphate/dihydrogen phosphate, saccharate, stearate, succinate, tartrate, tosylate and trifluoroacetate salts.

Suitable base salts of the compositions described herein are formed from bases which form non-toxic salts. Illustrative examples include the arginine, benzathine, calcium, choline, diethylamine, diolamine, glycine, lysine, magnesium, meglumine, olamine, potassium, sodium, tromethamine and zinc salts. Hemisalts of acids and bases may also be formed, for example, hemisulphate and hemicalcium salts.

In yet other embodiments, pharmaceutical formulations are provided. Illustratively, a pharmaceutical formulation comprises a peptide, sometimes called an antimicrobial peptide, described in accordance with the present disclosure. In one illustrative embodiment, the pharmaceutical formulation comprises any of the pharmaceutical compositions described herein. The previously described embodiments of the pharmaceutical compositions are applicable to the pharmaceutical formulations described herein.

The type of formulation employed for the administration of the compounds, sometimes called a peptide or an antimicrobial peptide, may be dictated by the particular compounds employed, the type of pharmacokinetic profile desired from the route of administration and the compound(s), and the state of the patient. The peptides may be formulated as pharmaceutical compositions for systemic administration. Such pharmaceutical compositions and processes for making the same are known in the art for both humans and non-human mammals. See, e.g., Remington: The Science and Practice of Pharmacy, (A. Gennaro, et al., eds., 19$^{th}$ ed., Mack Publishing Co., 1995).

In some embodiments, the pharmaceutical formulations described herein further comprise a pharmaceutically acceptable carrier. In some embodiments, the pharmaceutical formulations described herein further comprise a pharmaceutically acceptable diluent. Diluent or carrier ingredients used in the pharmaceutical compositions containing peptides can be selected so that they do not diminish the desired effects of the peptide. Examples of suitable dosage forms include aqueous solutions of the peptides, for example, a solution in isotonic saline, 5% glucose or other well-known pharmaceutically acceptable liquid carriers such as alcohols, glycols, esters, and amides.

As used herein, "carrier" refers to any ingredient other than the active component(s) in a formulation. Pharmaceutically acceptable carriers are determined in part by the particular composition being administered, as well as by the particular method used to administer the composition (see, e.g., Remington's Pharmaceutical Sciences, 17th ed. (1985)). The choice of carrier will to a large extent depend on factors such as the particular mode of administration, the effect of the carrier on solubility and stability, and the nature of the dosage form. In one illustrative aspect, the carrier is a liquid carrier.

As used herein, the term "pharmaceutically acceptable" includes "veterinarily acceptable", and thus includes both human and animal applications independently. For example, a "patient" as referred to herein can be a human patient or a veterinary patient, such as a domesticated animal (e.g., a pet) or a food animal.

In some embodiments, the pharmaceutical formulations described herein optionally include one or more other therapeutic ingredients. As used herein, the term "active ingredient" or "therapeutic ingredient" refers to a therapeutically active compound, as well as any prodrugs thereof and pharmaceutically acceptable salts, hydrates, and solvates of the compound and the prodrugs. Other active ingredients may be combined with the described peptides and may be either administered separately or in the same pharmaceutical formulation. The amount of other active ingredients to be given may be readily determined by one skilled in the art based upon therapy with described peptides.

In some embodiments, the pharmaceutical formulations described herein are a single unit dose. As used herein, the term "unit dose" is a discrete amount of the composition comprising a predetermined amount of the described peptides. The amount of the described peptides is generally equal to the dosage of the described peptides which would be administered to an animal or a convenient fraction of such a dosage such as, for example, one-half or one-third of such a dosage.

In one illustrative aspect, parenteral formulations may be suitably formulated as a sterile non-aqueous solution or as a dried form to be used in conjunction with a suitable vehicle such as sterile, pyrogen-free water. The preparation of parenteral formulations under sterile conditions, for example, by lyophilization, may readily be accomplished using standard pharmaceutical techniques well known to those skilled in the art.

The aqueous preparations according to the invention can be used to produce lyophilisates by conventional lyophilization or powders. The preparations according to the invention are obtained again by dissolving the lyophilisates in water or other aqueous solutions. The term "lyophilization," also known as freeze-drying, is a commonly employed technique for presenting proteins which serves to remove water from the protein preparation of interest. Lyophilization is a process by which the material to be dried is first frozen and then the ice or frozen solvent is removed by sublimation in a vacuum environment. An excipient may be included in pre-lyophilized formulations to enhance stability during the freeze-drying process and/or to improve the stability of the lyophilized product upon storage. For example, see Pikal, M. Biopharm. 3(9)26-30 (1990) and Arakawa et al., Pharm. Res., 8(3):285-291 (1991).

In some embodiments, the peptides in accordance with the present disclosure are described as antimicrobial peptides. In one embodiment, the solubility of the antimicrobial peptides used in the preparation of a parenteral formulation may be increased by the use of appropriate formulation techniques, such as the incorporation of solubility-enhancing agents.

In various embodiments, formulations for parenteral administration may be formulated to be for immediate and/or modified release. Modified release formulations include delayed, sustained, pulsed, controlled, targeted and programmed release formulations. Thus, a peptide may be formulated as a solid, semi-solid, or thixotropic liquid for administration as an implanted depot providing modified release of the active compound.

In other various embodiments, the administration according to the described methods is performed as a single dose administration. In other embodiments, the administration according to the described methods is performed as a multiple dose administration.

The formulations can be presented in unit-dose or multi-dose sealed containers, such as ampules and vials. The formulations can also be presented in syringes, such as prefilled syringes.

In various embodiments, the dosages of the antimicrobial peptides can vary significantly depending on the patient condition and the severity of the disease to be treated. The effective amount to be administered to a patient is based on body surface area, patient weight or mass, and physician assessment of patient condition.

As used herein, the term "effective amount" refers to an amount of an antimicrobial peptide, peptide, drug, or pharmaceutical agent that elicits the biological or medicinal response in a subject (i.e. a tissue system, animal or human) that is being sought by a researcher, veterinarian, medical doctor or other clinician, which includes, but is not limited to, alleviation of the symptoms of the disease or disorder being treated. In one aspect, the effective amount is that amount of an active which may treat or alleviate the disease or symptoms of the disease at a reasonable benefit/risk ratio applicable to any medical treatment. In another aspect, the effective amount is that amount of an inactive prodrug which when converted through normal metabolic processes to produce an amount of active drug capable of eliciting the biological or medicinal response in a subject that is being sought.

It is also appreciated that the dose, whether referring to monotherapy or combination therapy, is advantageously selected with reference to any toxicity, or other undesirable side effects, that might occur during administration of one or more of the antimicrobial peptides described herein. Further, it is appreciated that the co-therapies described herein may allow for the administration of lower doses of antimicrobial peptides that show such toxicity, or other undesirable side effects, where those lower doses are below thresholds of toxicity or lower in the therapeutic window than would otherwise be administered in the absence of a co-therapy.

As used herein, "administering" includes all means of introducing the antimicrobial peptides and compositions described herein to the host animal, including, but are not limited to, oral (po), intravenous (iv), intramuscular (im), subcutaneous (sc), transdermal, inhalation, buccal, ocular, sublingual, vaginal, rectal, and the like. The antimicrobial peptides and compositions described herein may be administered in unit dosage forms and/or formulations containing conventional nontoxic pharmaceutically-acceptable carriers, adjuvants, and/or vehicles.

As used herein "pharmaceutical composition" or "composition" refers to a mixture of one or more of the antimicrobial peptides described herein, or pharmaceutically acceptable salts, solvates, hydrates thereof, with other chemical components, such as pharmaceutically acceptable excipients. The purpose of a pharmaceutical composition is to facilitate administration of an antimicrobial peptide to a subject. Pharmaceutical compositions suitable for the delivery of antimicrobial peptides described and methods for their preparation will be readily apparent to those skilled in the art. Such compositions and methods for their preparation may be found, for example, in 'Remington's Pharmaceutical Sciences', 19th Edition (Mack Publishing Company, 1995).

Suitable dosages of the antimicrobial peptides can be determined by standard methods, for example by establishing dose-response curves in laboratory animal models or in humans in clinical trials. Illustratively, suitable dosages of antimicrobial peptides (administered in a single bolus or over time) include from about 1 pg/kg to about 10 μg/kg, from about 1 pg/kg to about 1 μg/kg, from about 100 pg/kg to about 500 ng/kg, from about 1 pg/kg to about 1 ng/kg, from about 1 pg/kg to about 500 pg/kg, from about 100 pg/kg to about 500 ng/kg, from about 100 pg/kg to about 100 ng/kg, from about 1 ng/kg to about 10 mg/kg, from about 1 ng/kg to 1 mg/kg, from about 1 ng/kg to about 1 μg/kg, from about 1 ng/kg to about 500 ng/kg, from about 100 ng/kg to about 500 μg/kg, from about 100 ng/kg to about 100 μg/kg, from about 1 μg/kg to about 500 μg/kg, or from about 1 μg/kg to about 100 μg/kg. In each of these embodiments, dose/kg refers to the dose per kilogram of a patient's or animal's mass or body weight.

The make and use of these peptides to sterilize raw fish and shellfish for food consumption are within the scope of the protection.

This disclosure identifies effective compositions for killing bacteria. In some embodiments, the bacteria are foodborne bacteria. In some embodiments, the bacteria are foodborne bacteria found in seafood. In some embodiments, these compositions are selected from the peptides group consisting of SEQ ID NO:11 (BMAP-27A), SEQ ID NO:12 (BMAP-27B), SEQ ID NO:13 (BMAP-27C), SEQ ID NO:15 (SMAP-29B), SEQ ID NO:16 (SMAP-29C), SEQ ID NO:17 (SMAP-29D), SEQ ID NO:18 (BMAP-24), and SEQ ID NO:19 (B22).

Material and Method

Cells and Reagents—

The BEAS-2B cell line was from the American Type Culture Collection and cultured in BEGM media with its supplements (11; Lonza). Peptides without or with covalently attached fluorophores were custom synthesized (Karybaybio) and purified to at least 95% purity. siRNAs specific to FPRL1 (sc-40123), EGFR (sc-29301), or a non-specific control siRNA (sc-37007) were from Santa Cruz Biotechnology.

Quantification of IL-6—

IL-6 production was quantified by ELISA using the OptEIA™ kit (BD Biosciences). A typical assay used $2 \times 10^4$ BEAS-2B cells/well grown for 24 h in flat-bottom 96-well plates. Poly(I:C) was added to a final concentration of 0.13 µg/ml.

Mic Determination—

Antimicrobial activity was determined using the broth microdilution method based on the general recommendation of the Clinical and Laboratory Standards Institute. Bacteria were grown in Mueller-Hinton broth at 37° C. until $OD_{625}$ reached 0.06, and then bacteria were further diluted into 1:20 for later use. Peptides were diluted in Mueller-Hinton broth at concentrations of 1, 2, 4, 8, 16, and 32 µg/ml. 10 microliter (µL) of diluted bacteria was mixed with 90 µL of peptides at varying concentrations followed by incubation at 37° C. for 16-18 hours. The MIC is the lowest peptide concentration at which visible growth was inhibited. The MIC value was determined at least twice in independent experiments and typically in 3-4 assays.

Hemolytic Activity—

The hemolytic activities of peptides were determined using human red blood cells (hRBCs) (Innovative Research, Inc., cat. # IPLA-WB3-18103). The hRBCs were washed three times with PBS and then resuspended in PBS. The hRBCs solution was mixed with serial dilutions of the peptides in PBS buffer. The reaction mixtures were incubated for 45 min at 37° C. After centrifugation at 94×g for 10 min, the intact hRBCs were pelleted and the hemoglobin released from hRBCs was monitored by measuring the absorbance of the supernatant at 415 nm. The background level of absorbance was measured in sampled incubated with only PBS buffer. 100% hemolysis was determined in sampled incubated with water. The percentage of hemolysis was calculated according to the following equation.

Percentage of hemolysis=$[(A_{sample}-A_{blank})/A_{water}]$*100%

Vibrios Killing Activity—

Vibrios bacteria such as *V. angustum* or *V. fischeri* were cultured in LM at 30° C. The *V. angustum* culture was 200× diluted, *V. fischeri* culture was 40× diluted. For *V. angustum* culture, peptides SMAP-29C and BMAP-27B at concentrations of 0.1 µM, 0.5 µM, and 1 µM were prepared. For *V. fischeri* culture, peptides SMAP-29 C and BMAP-27B at concentrations of 0.5 µM, 1 µM, and 2 µM were prepared.

The peptides were incubated with the bacteria for 1 hour at 30° C. before plated into the bacteria culture (100 µL peptides and 20 µL mock). The cultures were incubated overnight and Colony Forming Units (CFUs) were counted.

Selective antimicrobial peptides have effective activity against various species of Gram-negative bacterium, particularly to fish/human pathogens from *Vibrios* genus, as will be exemplified below.

The high efficiency of bacterial killing and the low toxicity of these peptides provide insights to alternative solutions to serve food processing industry and aquafarming, which is of great value to the entire consumer industry.

EXAMPLES

The following examples present features, aspects and advantages of the present invention. They are for illustrative purposes only. Any and all changes and modifications that come within the spirit of the disclosure are desired to be protected.

Example 1

Selective antimicrobial peptides against 19 Gram-Negative strains of bacteria

Various antimicrobial peptides required minimal inhibitory concentrations against 19 Gram-negative strains bacteria. Table 1 shows that SMAP 29 and BMAP 27 variants have low concentration requirement (16 µg/ml) to effectively inhibit almost all or at least majority of Gram-negative strains of bacteria. For example, BMAP-27, BMAP-27A, and BMAP-27B were able to completely inhibit all tested strains at or below 16 µg/ml of peptide. SMAP-29, SMAP-29B, and SMAP-29D were able to inhibit 16/19 strains tested at or below 16 µg/ml of peptide. This provides an opportunity to use SMAP-29 and BMAP-27 variants to contain infection by the Gram-negative bacteria in applicable situations. For Gram-positive bacteria, little inhibitory effects were observed. Thus, the peptides can be considered to have a more narrow spectrum of bacterial killing (Table 2).

TABLE 1

Minimal inhibitory concentrations of select antimicrobial peptides against 19 Gram-negative strains

| Organism IU or OC # | LL-37 | RL-37 | LL-29 | LL-29V | LL-29V2 | CAP-11 | CAP-11V1 | CAP-11V2 | CAP-11V3 | SMAP-29 |
|---|---|---|---|---|---|---|---|---|---|---|
| E. cloacae 4080 | 32 | 16 | 16 | 16 | 16 | 4 | 4 | 4 | 8 | 4 |
| E. cloacae 4092 | >32 | >32 | >32 | 32 | >32 | 8 | 4 | 16 | 16 | 4 |
| E. coli 4075 | >32 | >32 | >32 | >32 | >32 | >32 | >32 | >32 | >32 | >32 |
| E. coli ATCC 25922 | 32 | 16 | 16 | 8 | 16 | 4 | 4 | 8 | 16 | 4 |
| E. coli ATCC 35218 | 32 | 8 | 16 | 16 | 16 | 8 | 8 | 8 | 16 | 4 |
| E. coli IU0342 | 32 | 32 | 16 | 16 | 16 | 4 | 4 | 16 | 16 | 4 |
| E. coli J53 AzideR | >32 | 16 | 32 | 16 | 32 | 8 | 4 | 4 | 18 | 8 |
| E. coli MC4100 | >32 | >32 | 32 | 32 | >32 | 4 | 8 | 8 | 16 | 8 |
| K. pneumoniae ATCC 700603 | >32 | 16 | 32 | 16 | 32 | 16 | 8 | 16 | 32 | 8 |
| K. pneumoniae C2 | >32 | 16 | >32 | 16 | 32 | 8 | 8 | 8 | 32 | 8 |
| K. pneumoniae 4110 | >32 | >32 | >32 | 16 | >32 | 8 | 8 | 8 | 32 | 16 |
| K. pneumoniae OC8893 | >32 | >32 | >32 | 16 | 32 | 4 | 4 | 8 | >32 | 16 |
| P. aeruginosa ATCC 27853 | >32 | 32 | >32 | 16 | >32 | 4 | 4 | 8 | 32 | 8 |
| P. aeruginosa 4083 | 32 | 16 | >32 | 32 | >32 | 4 | 4 | 8 | 32 | 8 |
| P. aeruginosa PA01 | 32 | >32 | >32 | 32 | >32 | 8 | 2 | 8 | 32 | 8 |
| P. aeruginosa PA01 oprD | 32 | >32 | >32 | 32 | >32 | 8 | 16 | 8 | 32 | 8 |
| S. marcescens 4101 | >32 | >32 | >32 | >32 | >32 | >32 | >32 | >32 | >32 | >32 |
| S. marcescens 4104 | >32 | >32 | >32 | >32 | >32 | >32 | >32 | >32 | >32 | >32 |
| S. marcescens 7553 | >32 | >32 | >32 | 16 | >32 | 16 | 8 | 16 | 32 | 8 |
| Number of strains inhibited at 16 µg/ml: | 0/19 | 7/19 | 4/19 | 11/19 | 4/19 | 16/19 | 16/19 | 16/19 | 7/19 | 16/19 |

TABLE 1-continued

Minimal inhibitory concentrations of select antimicrobial peptides against 19 Gram-negative strains

| Organism IU or OC # | SMAP-29V | SMAP-29B | SMAP-29D | BMAP-27 | BMAP-27A | BMAP-27B | BMAP-27C |
|---|---|---|---|---|---|---|---|
| E. cloacae 4080 | 4 | 8 | 4 | 2 | 2 | 4 | 2 |
| E. cloacae 4092 | 32 | 16 | 8 | 2 | 4 | 4 | 4 |
| E. coli 4075 | >32 | >32 | >32 | 8 | 8 | 16 | 32 |
| E. coli ATCC 25922 | 8 | 8 | 4 | 2 | 2 | 4 | 2 |
| E. coli ATCC 35218 | 16 | 32 | 8 | 2 | 2 | 4 | 4 |
| E. coli IU0342 | 8 | 8 | 4 | 2 | 2 | 4 | 2 |
| E. coli J53 AzideR | 8 | 8 | 8 | 2 | 4 | 4 | 2 |
| E. coli MC4100 | 8 | 8 | 8 | 2 | 4 | 4 | 2 |
| K. pneumoniae ATCC 700603 | 16 | 16 | 16 | 2 | 4 | 4 | 4 |
| K. pneumoniae C2 | 16 | 8 | 8 | 2 | 4 | 4 | 2 |
| K. pneumoniae 4110 | 32 | 8 | 8 | 4 | 4 | 8 | 4 |
| K. pneumoniae OC8893 | 16 | 8 | 8 | 4 | 4 | 8 | 4 |
| P. aeruginosa ATCC 27853 | 16 | 8 | 8 | 2 | 4 | 4 | 2 |
| P. aeruginosa 4083 | 8 | 8 | 8 | 2 | 4 | 4 | 4 |
| P. aeruginosa PA01 | 16 | 8 | 8 | 2 | 4 | 4 | 4 |
| P. aeruginosa PA01 oprD | 8 | 8 | 8 | 2 | 4 | 4 | 2 |
| S. marcescens 4101 | >32 | >32 | >32 | 16 | 16 | 16 | >32 |
| S. marcescens 4104 | >32 | >32 | >32 | 8 | 8 | 18 | 16 |
| S. marcescens 7553 | 32 | 8 | 8 | 2 | 4 | 8 | 8 |
| Number of strains inhibited at 16 µg/ml: | 13/19 | 16/19 | 16/19 | 19/19 | 19/19 | 19/19 | 17/19 |

Example 2

Antimicrobial peptides are not potent inhibitors of Gram-positive bacteria

As described in Example 1, the prepared non-natural BMAP-27 and SMAP-29 variants did not show efficacy against Gram-positive bacteria as shown in Table 2.

TABLE 2

MIC of select peptides to four Gram-positive bacteria.

| Peptide | E. faecalis 51299 | E. faecalis 29212 | S. aureus 25923 | S. aureus 29213 |
|---|---|---|---|---|
| BMAP-27 | >32 | >32 | 16 | 16 |
| BMAP-27A | >32 | >32 | 16 | 16 |
| BMAP-27B | >32 | >32 | 32 | 32 |
| BMAP-27C | >32 | >32 | >32 | 32 |
| SMAP-29 | 32 | 32 | 8 | 8 |
| SMAP-29B | >32 | >32 | >32 | >32 |
| SMAP-29D | 32 | >32 | 16 | 16 |

This example shows in Table 2 that the peptides that are effective killing or inhibiting Gram-negative bacteria are not potent inhibitors of Gram-Positive strains, as the minimum required concentration is or larger than 16 µg/ml, as compared to the Gram-negative bacteria MIC shown in Table 1.

Example 3

SMAP-29 variants have efficient bacterial killing and reduced cytotoxicity

SMAP-29 and its non-natural variants SMAP-29B and SMAP-29D were able to kill various strains of Gram-negative bacteria efficiently with reduced cytotoxicity to the human cells (see FIGS. 4A-E and its legend).

As described above in FIGS. 4A-E, SMAP-29 and its non-natural variants SMAP-29B and SMAP-29D were able to inhibit majority of tested Gram-negative strains. However, the cytotoxicity of these peptides was reduced, or at least not worse than the control that causes cytotoxicity, as measured by red blood cell lysis, double-strand RNA induced IL-6 production (pro-inflammation cytokine), the inhibitory effect to LPS induced cytokine production, and cell metabolism rate of MTT assay.

Example 4

The non-natural SMAP-27 variants have efficient bacterial killing and reduced cytotoxicity BMAP-27 and its variants BMAP-27B and BMAP-27D were able to kill various strains of Gram-negative bacteria efficiently with reduced cytotoxicity to the human cells (see FIGS. 5A-E and its legend).

As described above in FIGS. 5A-E, BMAP-27 and its variants BMAP-27A, B and C were able to inhibit all of tested Gram-negative strains. However, the cytotoxicity of these peptides was reduced, as measured by red blood cell lysis, double strand RNA-induced IL-6 production (pro-inflammation), the inhibitory effect to LPS induced cytokine production, and cell metabolism rate of MTT assay.

Example 5

SMAP-29D and BMAP-27B have very rapid bacterial killing

Figures 6A, 6B:
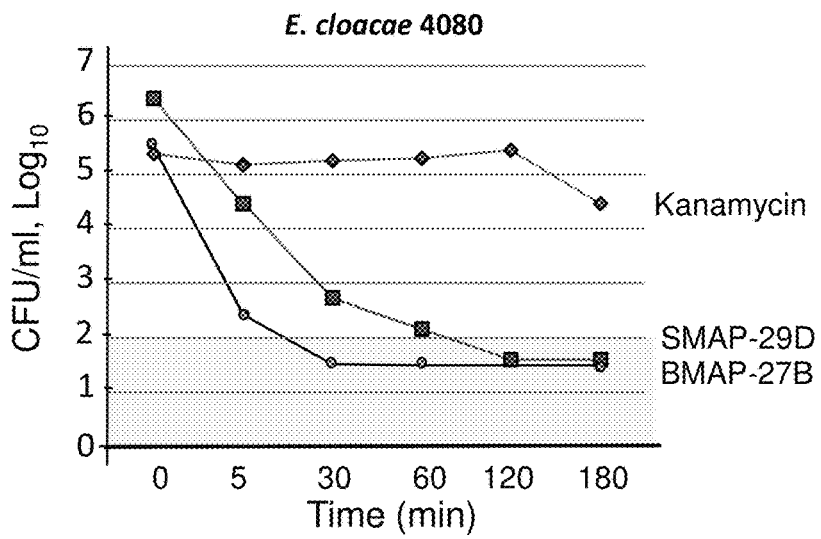

Variants SMAP-29D and BMAP-27B have more efficient bacterial killing ability as compared to the antibiotics, such as Kanamycin (See FIG. 6A). The rate of bacterial killing or these peptides are measured in terms of minutes, reflected by the colony forming unit reduction within 5 minutes. The bacterial fold reduction for various Gram-negative strains ranges from hundreds to thousands within 5 minutes and by 3 hours of application, the visible colonies are down to tens for most of the bacterial strains tested. (See FIG. 6B).

Example 6

Multiple Vibrio Species are highly sensitive to SMAP-29C

Figure 7:
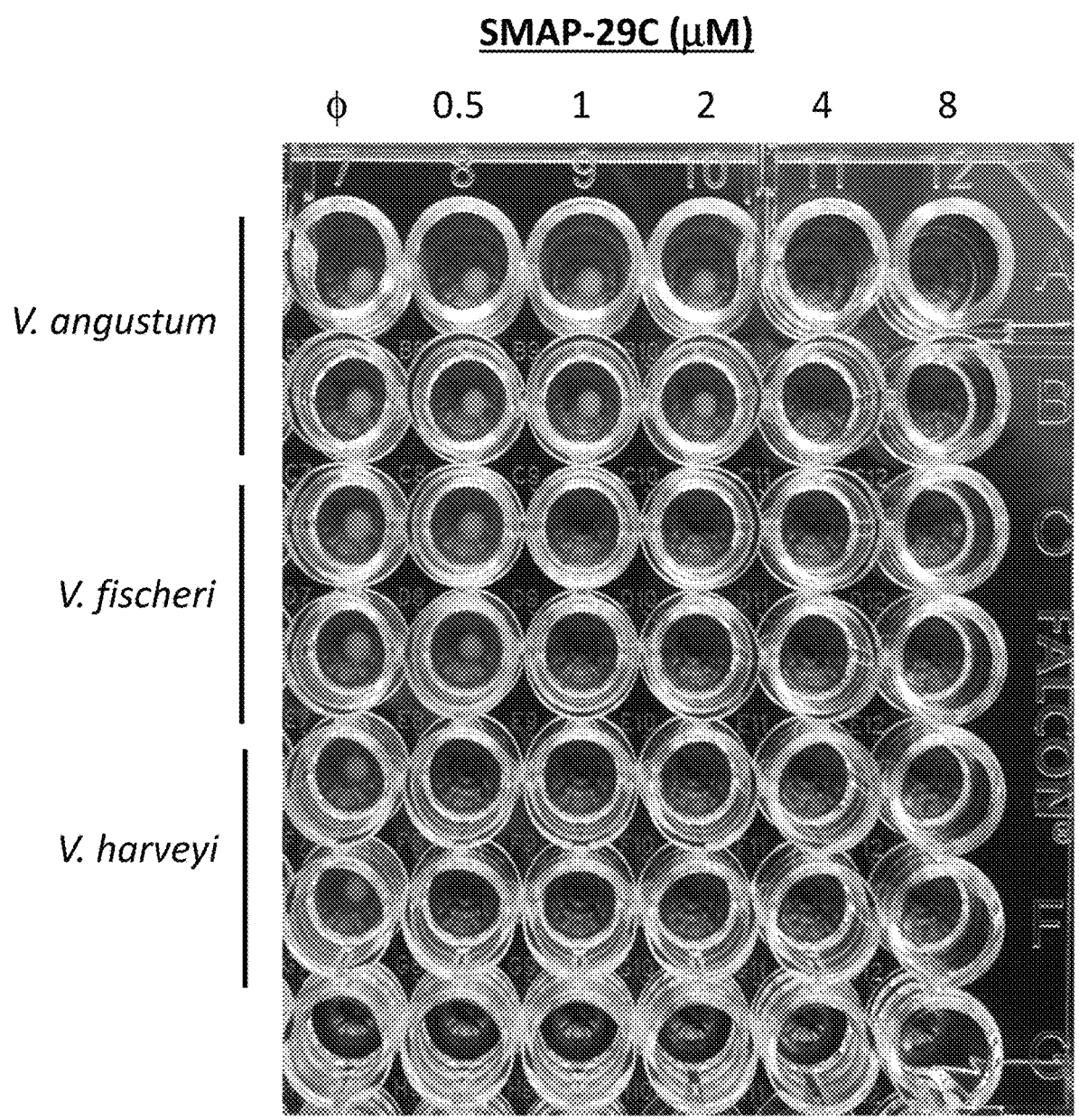
FIG. 7 shows multiple Vibrio species are highly sensitive to SMAP-29C.

Bacteria within Vibrio genus are highly sensitive to the SMAP-29C peptide. Various strains of Vibrio were treated with increasing concentrations of SMAP-29C (See FIG. 7). V. angustum, V. fischeri, and V. harveyi all showed growth reduction correlation to the concentration of SMAP-29C. This indicates that SMAP-29C is killing *vibrio* bacteria in a dose dependent manner.

Example 7

SMAP-29D and BMAP-27B killing of *V. angustum*

A fold reduction of *V. angustum* in the bacteria cultures with SMAP-29D or BMAP-27B was measured, indicating that *V. angustum* is highly sensitive to these two antimicrobial peptide variants. See FIG. 8. The fold change compared to mock controls are tens of thousands of folds. This indicates that SMAP-29D and BMAP-27B can be effective in treating a raw fish product that is infected by *V. angustum*.

Example 8

SMAP-29D and BMAP-27B killing of *V. fischeri*

A fold reduction of *V. fischeri* in the bacteria cultures with SMAP-29D or BMAP-27B was measured, indicating that *V. fischeri* is highly sensitive to these two antimicrobial peptide variants. See FIG. 9. The fold change compared to mock controls are tens of thousands of folds. These results indicate that SMAP-29D and BMAP-27B can be effective in treating a raw fish product that is infected by *V. fischeri*.

Example 9

*V. vulnificus* growth curve YJ106 is greatly reduced by BMAP-27B or SMAP-29D

*V. vulnificus* growth measured by OD600 was inhibited in a dose-dependent manner, especially by BMAP-27B at 1 µM concentration. The nearly complete inhibition by BMAP-27B to *V. vulnificus* at 1 µM suggests that the peptide can be an efficient tool to sterilize a raw fish product.

Example 10

Mechanism of action for bacterial killing by the cathelicidins

Illustratively, BMAP-27B and SMAP-29D may interact with the Gram-negative membrane and cause the loss of the integrity of the cellular content. To confirm that this is the case, phase contrast fluorescence microscopy with *V. vulnificus* treated for 5 min was performed with 4 µM fluorescein-labeled SMAP-29D (FIG. 11). The FAM-labeled SMAP-29D had comparable bactericidal activity as SMAP-29D. The *V. vulnificus* cells treated with FAM-SMAP-29D all exhibited a bulge in the membrane that typically located close to the midpoint of the cells, the site expected for bacterial binary fission to take place. Within the membrane, it is clear that FAM-SMAP-29D is concentrated. When stained with DAPI to localize the *V. vulnificus* chromosome, the bacterial chromosome appears to be partially displaced into the membrane-encased bulge. These results suggest the SMAP-29D interacts with the cytoplasmic membrane of the bacteria, weakens its ability to withstand osmolysis that then cause a relocation of the bacterial chromosomal DNA.

Example 11

BMAP-27B and SMAP-29D can kill colistin-resistant bacteria.

Recently, plasmid-mediated polymyxin resistance encoded by the mcr-1 gene was found in multiple Gram-negative bacteria first in Southeastern China, then in many other countries including the United States. Whether BMAP-27B and SMAP-29D could kill the *E. coli* strain harboring the mcr-1 gene on a plasmid named pHNSHP45 in southern China named pHNSHP45 was examined *E. coli* Top10 harboring pHNSHP45 (Top10pHNSHP45) was resistant to colistin, as expected, but killed by 2 µM BMAP-27B and SMAP-29D with only a 5 minute incubation (FIG. 12A). Top10 lacking the mcr-1 plasmid was sensitive to all three antibiotics. BMAP-27D and SMAP-29C reduced Top10pHNSHP45 colony formation by several logs with only a 5 minute incubation while colistin had little effect (FIG. 12B). BMAP-27 and SMAP-29D had comparable MICs for Top10 and Top10pHNSHP45. These results show that Top10pHNSHP45 apparently does not confer cross-resistance to BMAP-27B or SMAP-29D. Furthermore, BMAP-27B and SMAP-29D could effectively kill colistin-resistant bacteria.

Example 12

Identification of B22 and BMAP-24

Bactericidal peptides shorter than BMAP-27B or SMAP-29D that retain the activities of these peptides were generated. The reduced length should decrease the cost of synthesis and increase the efficiency of synthesis. The sequence of BMAP-27B was used to generate a series of truncated peptides. A number of the peptides with truncations, amino acids substitutions were generated and tested for the killing of colistin-resistant *E. coli*, Top10pHNSHP45. Two peptides were found to have improved bactericidal activity relative to BMAP-27B (FIG. 13). BMAP-24 that contains residues 1-24 of BMAP-27B and B22, which lacks 5 residues at the N-terminal region of BMAP-27B, reduced the number of viable colonies relative to BMAP27B. Both BMAP-24 and B22 had improved MIC against the majority of the 19 strains of Gram-negative bacteria used to select for effective cathelicidins (Table 3). Similar to BMAP-27B, BMAP-24, and B22 had higher MICs against the majority of *Serratia marcescens* strains. The lengths and bactericidal activities of BMAP-24 and B22 were selected for additional characterizations.

TABLE 3

Summary of the minimal inhibitory concentrations (MIC) of B22 and BMAP-24 against 19 strains of Gram-negative bacteria. The MIC of BMAP-27 is provided as a comparator.

| Species | Strain | BMAP27B (µM) | BMAP-24 (µM) | B22 (µM) |
|---|---|---|---|---|
| *Enterobacter cloacae* | OC4080 | 4 | 2 | 2 |
| *Enterobacter cloacae* | OC4092 | 4 | 2 | 2 |
| *Escherichia coli* | ATCC 25922 | 4 | 2 | 2 |
| *Escherichia coli* | ATCC 35218 | 4 | 4 | 2 |
| *Escherichia coli* | IU342 | 2 | 2 | 2 |
| *Escherichia coli* | J53 AzideR | 4 | 2 | 1 |
| *Escherichia coli* | OC4075 | 4 | 2 | 1 |
| *Escherichia coli* | UTI59 | 4 | 2 | 2 |
| *Klebsiella pneumonia* | ATCC 700603 | 4 | 2 | 2 |
| *Klebsiella pneumonia* | C2 | 4 | 2 | 2 |
| *Klebsiella pneumonia* | OC4110 | 8 | 2 | 4 |
| *Klebsiella pneumonia* | OC8893 | 8 | 2 | 2 |
| *Pseudomonas aeruginosa* | ATCC 27853 | 4 | 2 | 2 |
| *Pseudomonas aeruginosa* | OC4083 | 4 | 1 | 2 |
| *Pseudomonas aeruginosa* | PAO1 | 4 | 2 | 2 |
| *Pseudomonas aeruginosa* | PAO1 oprD | 4 | 2 | 2 |
| *Serratia marcescens* | 4075 | 16 | >16 | >16 |
| *Serratia marcescens* | 4101 | 16 | >16 | >16 |
| *Serratia marcescens* | 4104 | 16 | 8 | 2 |
| *Serratia marcescens* | 7553 | 8 | 4 | 2 |

BMAP-24 and B22, like BMAP-27B, remain less able to inhibit Gram-positive bacteria. The MICs for two strains of *S. aureus* were higher than or equal to 64 µM. With two strains of *Enterococcus fecalis*, the MICs were comparable or worse than the MIC for BMAP-27B (Table 4). These results show that B22 and BMAP-24 have reduced ability to kill Gram-positive bacteria; they are more specific to Gram-negative bacteria.

TABLE 4

Minimal inhibitor concentration (MIC) of peptides BMAP-24 and B22 against Gram-positive bacteria.

| Species | Strain | BMAP-24 (µM) | B22 (µM) | BMAP-27B (µM) |
|---|---|---|---|---|
| Escherichia coli | ATCC 25922 | 2 | 2 | 3 |
| Staphylococcus aureus | 29213 | >64 | >64 | >64 |
| Staphylococcus aureus | 25923 | >64 | >64 | >64 |
| Enterococcus faecalis | 51299 | 4 | >32 | 8 |
| Enterococcus faecalis | 29212 | 4 | >32 | 4 |

Clinical isolates of *K. pneumoniae* from healthcare facilities from Indiana healthcare facilities that have been identified to be carbapenem resistance were obtained. Of these, two have been identified to have the NDM1 gene. In a screen for colistin-resistance, three strains were also found to have high MICs for colistin sulfate (Table 5). B22 and BMAP-24 had MICs of 4 µM or lower with the carbapenem-resistant *K. pneumoniae*. These results show that B22 and BMAP-24 can inhibit colistin-resistant and carbapenem-resistant bacteria. BMAP-27B was also demonstrated to inhibit colistin-resistant and carbapenem-resistant bacteria. Thus, B22 and BMAP-24 retained these two important activities.

TABLE 5

Minimal inhibitor concentration (MIC) of peptides BMAP-24 and B22 on bacteria resistance to Colistin sulfate and carbapenems.

| Species | Strain | Antibiotic$^R$ | Colistin sulfate (µM) | BMAP-24 (µM) | B22 (µM)) |
|---|---|---|---|---|---|
| Escherichia coli | ATCC25922 | none | 1 | 2 | 2 |
| Klebsiella pneumonia | 88 | Carbapenem (NDM1+) | 16 | 2 | 4 |
| Klebsiella pneumonia | 262 | Carbapenem (NDM1+) | 16 | 2 | 4 |
| Klebsiella pneumonia | 27 | Carbapenem | >32 | 4 | 4 |
| Klebsiella pneumonia | 49 | Carbapenem | 4 | 2 | 2 |
| Klebsiella pneumonia | 83 | Carbapenem | 2 | 2 | 2 |
| Klebsiella pneumonia | 84 | Carbapenem | 2 | 2 | 2 |

Example 13

B22 has reduced activation of Toll-like receptor 3 in vitro

Previous analysis has shown that BMAP-27B and SMAP-29D have reduced activation of proinflammatory response when compared to that of the human cathelicidin LL-37 (FIG. 4). Given that B22 and BMAP-24 have improved bactericidal activities compared to BMAP-27B, the production of the cytokine interleukin 6 (IL-6) and Interleukin 8 (IL-8) in response to the presence of poly(I:C), a potent agonist of Toll-like receptor 3 that could activate the production of proinflammatory cytokines was measured. The lung epithelial BEAS-2B cells were used and B22 and BMAP-27B at 2 µM had only minimal production of both IL-6 and IL-8 (FIGS. 14A, B). B22 and BMAP-24 are not activators of proinflammatory activity.

Another potential source of cytotoxicity for antimicrobial peptides is the lysis of human cells. To examine this, B22 and BMAP-24 were tested for the lysis of human red blood cells (hRBCs). A range of concentrations from 2 to 8 µM were examined LL-37, which has previously demonstrated hRBC lysis activity, lysed hRBC when present at 4 or 8 µM (FIG. 15). BMAP-24 also was able to lyse hRBC and in a concentration-dependent manner. B22, however, had only minimal hRBC lysis at concentrations up to 8 µM (FIG. 15).

Example 14

B22 can prevent lethal sepsis in mice

The efficacy of B22 as a bacteriocide of Gram-negative bacteria and its inability to activate proinflammatory cytokines and reduced lysis of human red blood cells prompted us to examine its efficacy in an animal-bacterial infection model. A lethal sepsis model from *Vibrio vulnificus* infection of CD-1 mice was selected. *V. vulnificus* has an LD50 of 10 cfu in this model and 300 cfu was introduced to a surgical incision in the back of the mice. Cages of 5 mice were monitored every 2 h. Mice treated with the media for *V. vulnificus* and with B22 alone exhibited no symptom throughout the experiment (FIG. 16). Mice inoculated with *V. vulnificus* but not treated with B22 all succumbed to the infection within 24 h. Mice that had 10 µL of B22 at 5 µM 1 h added to the surgical incision 1 h after the introduction of *V. vulnificus* had 4 mice that exhibited no symptoms and 1 that had to be euthanized. These results show that B22 added at 1 h after the inoculation of the highly lethal pathogen *V. vulnificus* could prevent sepsis induced by *V. vulnificus*.

While the disclosure has been illustrated and described in detail in the foregoing figures and description, the same is to be considered as exemplary and not restrictive in character, it being understood that only illustrative embodiments thereof have been shown and described and that all changes and modifications that come within the spirit of the disclosure are desired to be protected.

Example 15

B22a inhibits Gram-negative bacteria growth

The C-terminus of natural peptides typically contain a carboxyl group that could affect interaction with negatively-charged phospholipids. Therefore, to eliminate the carboxyl group, the B22 peptide was synthesized with a C-terminal amide, resulting in a peptide named B22a (SEQ ID NO. 28). B22a was tested against 20 strains of Gram-negative bacteria using the broth dilution assay to determine the minimal inhibitory concentration (MIC) (CLSI, 2015). B22a was improved for inhibiting the majority of the Gram-negative bacteria of the Enterobacterioacea, including *Enterobacter cloacae, Escherichia coli, Pseudomonas aeruginosa*, and *Klebsiella pneumoniae* (Table 6). *Serratia marcescens*, which was shown to not be sensitive to the progenitors of B22 (Kao et al., 2016), remain insensitive to B22a.

TABLE 6

C-terminally amidated B22 results in more effective inhibition of bacterial growth.

| Species | Strain | Minimal inhibitory concentration (mM) | | |
|---|---|---|---|---|
| | | BMAP-27B | B22 | B22a |
| Enterobacter cloacae | OC4080 | 4* | 4 | 4 |
| Enterobacter cloacae | OC4092 | 4 | 4 | 4 |
| Escherichia coli | ATCC 25922 | 4 | 2 | 2 |
| Escherichia coli | ATCC 35218 | 4 | 4 | 2 |
| Escherichia coli | IU342 | 2 | 4 | 2 |
| Escherichia coli | J53 AzideR | 4 | 4 | 2 |
| Escherichia coli | OC4075 | 4 | 4 | 2 |
| Escherichia coli | MC4100a | 4 | 4 | 4 |
| Escherichia coli | UTI89 | 4 | 2 | 2 |
| Klebsiella pneumonia | ATCC 700603 | 4 | 2 | 2 |
| Klebsiella pneumonia | C2 | 4 | 4 | 2 |
| Klebsiella pneumonia | OC4110 | 8 | 4 | 2 |
| Klebsiella pneumonia | OC8893 | 8 | 4 | 2 |
| Pseudomonas aeruginosa | ATCC 27853 | 4 | 4 | 2 |
| Pseudomonas aeruginosa | OC4083 | 4 | 2 | 2 |
| Pseudomonas aeruginosa | PAO1 | 4 | 4 | 2 |
| Pseudomonas aeruginosa | PAO1 oprD | 4 | 4 | 2 |
| Serratia marcescens | 4075A | 16 | >32 | NT |
| Serratia marcescens | 4101 | 16 | >32 | >32 |
| Serratia marcescens | 4104 | 16 | >32 | >32 |

Example 16

B22a inhibits Gram-negative bacteria growth.

The broth dilution assay tested for the inhibition of growth. To determine whether B22a has bactericidal activity, viable colonies that formed after bacteria were treated with 2 μM of B22a for 30 min were enumerated (Table 7). Peptide B22a reduced viable colony formation by *E. coli* by over 2 orders of magnitude. B22a reduced viable colony formation by *P. aeruginosa* by over 3 orders of magnitudes. B22a, like its predecessor B22, is a bactericidal for Gram-negative bacteria.

TABLE 7

Bactericidal activity of B22a and other C-terminally amidated peptides on *E. coli* and *P. aeruginosa* viable colony formation.

| | E. coli ATCC 25922 | Fold reduction | P. aeruginosa PAO1 | Fold reduction |
|---|---|---|---|---|
| Mock | $8 \times 10^5$ | 1 | $1.2 \times 10^5$ | 1 |
| B22a | $1.3 \times 10^3$ | 615 | <20 | >6000 |
| B22m1 | $4.7 \times 10^5$ | 170 | <20 | >6000 |
| B22m2 | $8.7 \times 10^4$ | 9 | $7.3 \times 10^3$ | 164 |

Example 17

B22a effects antibiotic resistant bacteria

Antibiotic resistant Enterobacteriacea is a growing concern. Resistant bacteria have recently overcome the two lines of antibiotics that have been put in reserve for use only when necessary: carbapenems and polymyxins. *Klebsiella pneumoniae* is especially concerning, as strains isolated from patients have been documented to become resistant to either or both carbapenems and the polymyxin named colistin (Sanchez et al., 2013). Since B22a can effectively kill members of the Enterobacteriacea, B22a was tested against 20 clinical isolates of *K. pneumoniae* that have been characterized for resistance to carbapenems (imipenem or meropenem) and/or Colistin. For all 19 of the 20 clinical isolates strains, the minimal inhibitory concentrations of B22a appear to be unchanged from *K. pneumoniae* that have not acquired drug resistance. The remaining strain, Isolate 361, had only a two-fold increase in the MIC value. These results show that B22a is capable of inhibiting multi-drug resistant clinical isolates of *K. pneumoniae*.

Example 18

B22a does not significantly increase human red blood cell lysis

The increased efficacy of B22a to kill bacteria raises the possibility that it is also capable of interacting with mammalian cells and cause cell damage. Mammalian cells are thought to be less susceptible to cathelicidin peptides in part because the composition of their membrane will be less likely to interact with the peptides. To address this directly, human red blood cells (hRBCs) were tested for lysis after a 45-minute incubation with the peptides. The total lysis of hRBCs was determined by adding water to the cells. The amount of lysis during handling was determined by the addition of phosphate buffered saline at the same volume as that of the peptides. At a final concentration of 2 micromolar of LL-37, a low abundance of hemoglobin outside of the cells was detected (FIG. 17). B22, B22a, ShpC (cathelicidin from sheep) and BMAP-27B (cathelicidin from cows) all caused a minimal amounts of hemoglobin release from hRBCs.

To better assess hRBC lysis, increasing concentrations of the peptides were added. LL-37 resulted in significantly higher hRBC lysis as its concentration increased to beyond a final concentration of 10 micromolar (FIG. 18). In contrast, B22a did not significantly increase hRBC lysis at even a final concentration of 60 micromolar (FIG. 18). These results suggest that the chemically modified B22a can selectively target bacteria without significantly harmful effects on human cells.

Example 19

B22a affects bacteria in biofilms

Bacteria growing in biofilms can resist antibiotics due to the formation of extracellular matrix and changes in growth of the bacteria (Hoiby et al., 2010). Several of the bacteria that were killed by either B22 or B22a formed an abundance of extracellular polysaccharides, suggesting that it and similar peptides can penetrate dense extracellular matrix of bacteria. To examine this directly, *Vibrio cholerae* were grown into biofilms on a glass surface in a microfluidic chamber and monitored using microscopy. The bacterial cells were stained for 5 min to detect live cells and dead ones at 1 hour intervals. Treatment with either 100 nM of B22 flowed onto the biofilm resulted in rapid death of the bacteria in biofilms (FIGS. 19 and 20). These results show that B22 can kill bacteria growing in biofilms.

The inhibition of biofilm bacteria growth at 100 nM concentrations of the peptides was unexpected. The dogma in the field is that these AMPs are effective at micromolar concentrations where they could intercalate in bacterial membrane, oligomerize, and form a structure in the membrane that enables the influx of water to kill bacteria (Wang 2008). The low concentration of B22a that could result in the killing of biofilm bacteria suggests that B22a has an additional activity distinct from the formation of a multi-subunit pore in bacteria.

Example 20

B22a can kill bacteria without the formation of a multi-subunit structure.

To examine further whether B22a can kill bacteria without the formation of a multi-subunit structure, two additional peptides were chemically synthesized. B22m1 (SEQ ID NO. 29 and B22m2 (SEQ ID NO. 30) both have C-terminal amides. In addition, B22m1 has the phenylalanine at the 9th residue substituted with alanine. B22m2 has two substitutions of the phenylalanines at the 1st and 9th residue with alanines. The replacements of the hydrophobic phenylalanines with the smaller and less hydrophobic alanines should reduce the hydrophobic interactions between peptides that will generate a stable oligomer. When tested for bactericidal activity, B22m1 had comparable killing of E. coli and P. aeruginosa as did B22a. B22m2, with two amino acid substitutions from B22a, had reduced killing, but was still able to reduce viable colony formation by P. aeruginosa by more than 2 logs. In the broth dilution assay, B22m1 had the same minimal inhibitory concentration for the clinical isolates of Klebsiella pneumoniae and for E. coli and P. aeruginosa as does B22a (Table 8 and Table 9). All of these results support the idea that oligomerization of B22a to form a pore in the bacterial membrane is not required for its bactericidal activity.

TABLE 8

B22a can inhibit the growth of multi-drug resistance clinical isolates of Klebsiella pneumoniae.

| K. pneumoniae Strain | MIC (mg/ml) | | | B22a Medium MIC (mM) | B22m1 Medium MIC (mM) |
|---|---|---|---|---|---|
| | Imipenem | Meropenem | Colistin | | |
| 88 (NDM1+) | 16 | >16 | NT | 2 | 2 |
| 92 | >64 | >16 | NT | 2 | 2 |
| 109 | 16 | >16 | NT | 2-4 | NT |
| 113 | 16 | >16 | NT | 4 | NT |
| 116 | 8 | >16 | NT | 2-4 | NT |
| 118 | 32 | >16 | NT | 2-4 | NT |
| 136 | 8 | >16 | NT | 4 | NT |
| 170 | NT | >32 | NT | 2 | NT |
| 256 | ≥16 | 4 | NT | 2 | NT |
| 262 (NDM1+) | >16 | ≥6 | >8 | 4 | NT |
| 265 | 48 | ≥64 | NT | 4 | NT |
| 280 | ≥16 | ≥64 | NT | 4 | NT |
| 281 | 4 | ≥64 | NT | 2-4 | NT |
| 284 | 8 | ≥64 | 16 | 4 | NT |
| 286 | ≥16 | ≥64 | NT | 2 | NT |
| 328 | NT | ≥16 | NT | 4 | NT |
| 330 | 4 | ≥16 | >16 | 4 | NT |
| 361 | >16 | ≥16 | >16 | 8 | NT |
| 365 | NT | ≥16 | NT | 2-4 | NT |
| 399 | NT | ≥16 | NT | 2 | NT | bacterial growth, 30 nM of the peptides was added to growing cultures of P. aeruginosa. This low concentration of the peptide should further decrease the possibility of peptide oligomerization, as oligomerization should be dependent on the concentration of the peptide. The growth of the bacterial culture was then monitored over time. After the addition of the B22a or B22m1, the growth rate of P. aeruginosa was perceptibly reduced (FIGS. 21 and 22). The cell division time of E. coli and Enterobacter cloacae were also in the absence or presence of 100 nM of B22a. The presence of B22a increased the doubling time of both bacterial by more than 2-fold. These result shows that B22a and B22m1 will decrease bacterial growth. Should B22a and B22m1 inhibit bacteria growth as well as kill bacteria through the formation of higher order structures in the membrane, the peptides may have multiple mechanisms to act against bacteria survival. Peptides that act by multiple mechanisms may result in lower bacterial resistance to the peptides.

Example 21

B22a can kill bacteria without the formation of a multi-subunit structure.

Since B22a was effective in preventing infection of V. vulnificus in a surgical incision model, we tested it for efficacy for systemic infection in a mouse septicemia model (1). Groups of mice (strain CD-1) were first injected with iron sulfate, followed 1 h later with an intraperitoneal injection of 1×10e6 colony forming units of V. vulnificus strain CMCP1. The B22a was then injected intraperitoneally 1 h later and morbidity was monitored hourly for two days. Control mice injected with B22a did not exhibit distress or signs of toxicity for during the experiment (FIG. 23A). However, at either 10 or 20 µM, B22a did not prevent septicemia (FIG. 23B).

The lack of efficacy of B22a in inhibiting systemic bacterial infection may have been due to it not being sufficiently stable in vivo. Therefore, three peptides were synthesized that contain the B22 amino acid sequence with additional modifications. Peptide AB22a (SEQ ID No. 32) has an N-terminal acetyl group ($CH_3C(O)$) and a C-terminal amide ($NH_2$). Peptide AB22P (SEQ ID No. 33) has an N-terminal acetyl group and a C-terminal polyethyleneglycol (PEG) (PEG=conjugated 8-amino 3,6-dioxaoctanoic acid). Peptide PB22N (SEQ ID No. 34) has a PEG at the N-terminus. In vitro, PB22N was effective in inhibiting the growth of the majority of the Gram-negative bacteria of the Enterobacteriacea. The MICs were approximately two-fold better than that of B22a (Table 10). PB22N was also

TABLE 9

Amino acid substitutions in B22m1 did not affect the MIC against E. coli and P. aeruginosa. (Table 9 discloses SEQ ID NOS 28-30, respectively, in order of appearance)

| | | MIC (µM) | |
|---|---|---|---|
| Name | Sequence | E. coli ATCC 25922 | P. aeruginosa PAO1 |
| B22a | FRKKLKKLFKKLSPVIPLLKLGNH$_2$ | 2 | 2 |
| 322m1 | FRKKLKKLAKKLSPVIPLLKLGNH$_2$ | 2 | 2 |
| B22m2 | ARKKLKKLAKKLSPVIPLLKLGNH$_2$ | 4 | 4 |

To further support the idea that B22a and comparable peptides do not need to form higher order structures to affect efficacious in inhibiting antibiotic-resistant clinical isolates of Klebsiella pneumoniae (Table 11).

PB22N and other modified peptides were tested in a septicemic mouse model. *V. vulnificus* is a highly-pathogenic bacterium, causing septicemia and high mortality. In mice injected intraperitoneally with *V. vulnificus*, the majority of the mice had to be euthanized within 24 h due to severe symptoms associated with septicemia (FIG. 23B). Notable, mice injected with *V. vulnificus* and then injected 1 h later with a single dose of either 10 or 20 μM of PB22N survived and did not exhibit symptoms of infection (FIG. 23B). Furthermore, mice injected with peptides AB22a, AB22P and PB22N all had no obvious effects on mice behavior or appearance, indicating that these modified peptides are not obviously toxic. PB22N was effective in preventing mice from succumbing to systemic infection by the highly virulent *V. vulnificus*.

TABLE 10

The MIC of select peptides against twenty representative Gram-negative bacteria of the Enterobacteriacea.

| | | Minimal inhibitory concentration (μM) | | | | |
|---|---|---|---|---|---|---|
| Species | Strain | LL-37 | BMAP-27B | B22 | B22a | PB22N |
| *Enterobacter cloacae* | OC4080 | 32 | 4 | 4 | 4 | 0.5 |
| *Enterobacter cloacae* | OC4092 | >32 | 4 | 4 | 4 | 1 |
| *Escherichia coli* | ATCC 25922 | 32 | 4 | 2 | 2 | 1 |
| *Escherichia coli* | ATCC 35218 | 32 | 4 | 4 | 2 | 1 |
| *Escherichia coli* | IU342 | 32 | 2 | 4 | 2 | 1 |
| *Escherichia coli* | J53 AzideR | >32 | 4 | 4 | 2 | 1 |
| *Escherichia coli* | OC4075 | >32 | 4 | 4 | 2 | 1 |
| *Escherichia coli* | MC4100a | >32 | 4 | 4 | 4 | 1 |
| *Escherichia coli* | UT189 | >32 | 4 | 2 | 2 | 1 |
| *Klebsiella pneumonia* | ATCC 700603 | >32 | 4 | 2 | 2 | 1 |
| *Klebsiella pneumonia* | C2 | >32 | 4 | 4 | 2 | 1 |
| *Klebsiella pneumonia* | OC4110 | >32 | 8 | 4 | 2 | 1 |
| *Klebsiella pneumonia* | OC8893 | >32 | 8 | 4 | 2 | 1 |
| *Pseudomonas aeruginosa* | ATCC 27853 | >32 | 4 | 4 | 2 | 1 |
| *Pseudomonas aeruginosa* | OC4083 | >32 | 4 | 2 | 2 | 1 |
| *Pseudomonas aeruginosa* | PAO1 | 32 | 4 | 4 | 2 | 1 |
| *Pseudomonas aeruginosa* | PAO1 oprD | 32 | 4 | 4 | 2 | 1 |
| *Serratia marcescens* | 4075A | >32 | >16 | >32 | NT | 32 |
| *Serratia marcescens* | 4101 | >32 | >16 | >32 | >32 | 32 |
| *Serratia marcescens* | 4104 | >32 | >16 | >32 | >32 | >32 |

TABLE 11

MIC of B22 and PB22N against 20 drug-resistant clinical isolates of *K. pneumoniae*

| *K. pneumoniae* | MIC (μg/ml) | | | B22a | PB2N |
|---|---|---|---|---|---|
| Strain | Imipenem | Meropenem | Colistin | (μM) | (μM) |
| 88 (NDM1+) | 16 | >16 | NT | 2 | 2 |
| 92 | >64 | >16 | NT | 2 | 1-2 |
| 10916 | >16 | | NT | 2-4 | 1 |
| 110113 | 16 | >16 | NT | 4 | NT |
| 116 | 8 | >16 | NT | 2-4 | 0.5 |
| 118 | 32 | >16 | NT | 2-4 | 1 |
| 136 | 8 | >16 | NT | 4 | 2 |
| 170 | NT | >32 | NT | 2 | 1 |
| 256 | ≥16 | 4 | NT | 2 | 1-2 |
| 262 (NDM1+) | >16 | ≥64 | NT | 4 | 2 |
| 265 | 48 | ≥64 | >8 | 4 | 2-4 |
| 280 | ≥16 | ≥64 | NT | 4 | 2 |
| 281 | 4 | >64 | NT | 2-4 | 1 |
| 284 | 8 | ≥64 | 16 | 4 | 1 |
| 286 | ≥16 | ≥64 | NT | 2 | 2 |
| 328 | NT | ≥16 | NT | 4 | 2 |
| 330 | 4 | ≥16 | >16 | 4 | 1 |
| 361 | >16 | ≥16 | >16 | 8 | 8 |
| 365 | NT | ≥16 | NT | 2-4 | 1 |
| 399 | NT | ≥16 | NT | 2 | 2 |

REFERENCES

Nguyen, L. T. et al., "The expanding scope of antimicrobial peptide structures and their modes of action," Trends in Biotechnology, 2011, 9, 464-472.

Zasloff, M. "Defending the epithelium," Nature Medicine, 2006, 12, 607-608.

Wang, G. "Structures of Human Host Defense Cathelicidin LL-37 and its smallest antimicrobial peptide KR-12 in lipid micelles," J. Biol. Chem., 2008, 283, 32637-32643.

Zanetti, M., "Cathelicidins, multifunctional peptides of the innate immunity," J. of Leukocyte Biology, 2004, 75, 39-48.

Liu Y Y et al, "Emergence of plasmid-mediated colistin resistance mechanism MCR-1 in animals and human beings in China: a microbiological and molecular biological study," Lancet Inf Dis, 2016, 16, 161-168.

Rhouma M et al., "Colistin in pig production: chemistry, mechanism of antibacterial action, microbial resistance, and one health perspectives," Fron. Microb., 2016, 7, 1789, 22 pages.

Mediavilla J. R., et al., "Colistin and carbapenem-resistance *Escherichia coli* harboring mcr-1 and bla NDM-5 causing a complicated urinary tract infection in a patient in the United States," mBio, 2016, 7(4), e01191-16, 4 pages.

Li H., Estabrook M., Jacoby G. A. Nichols W. W., Testa R. T. Bush K. 2015. In vitro susceptibility of characterized β-lactamase-producing strains tested with Avibactam combinations. Antimicro. Agents Chemother. 59: 1789-1793.

Starks A M et al, "Pathogenesis of infection by clinical and environmental strains of *Vibrio vulnificus* in iron-dextran-treated mice," Infection and Immunity, 2000; 68:5785-5793.

Clinical and Laboratory Standards Institute. 2015. Performance standards for antimicrobial susceptibility testing, 24th informational supplement. CLSI document M100-S25. Clinical and Laboratory Standards Institute, Wayne, Pa.

Kao, C., Lin X., G. Yi, Zhang Y., D. Rowe-Magnus, and K. Bush. 2016. Cathelicidin antimicrobial peptides with reduced activation of Toll-like receptor signaling have potent bactericidal activity against colistin-resistant bacteria. mBio 4: e01418-16.

Sanchez G. V., R. N. Master. R. B. Clark, M. Fyyaz, P. Duvvuri, G. Ekta, and J. Bordon. 2013. *Klebsiella pneumoniae* antimicrobial drug resistance, United States, 1998-2010. Emerging infectious Diseases. 19: 133-136.

Hoiby N., Bjarnsholt T., Givskov M., Molin S, and Ciofu O. 2010. Antibiotic resistance of bacterial biofilms. Intern. J Antimicrobial Agents. 35: 322-332.

Wang G. 2008. Structures of human host defense cathelicidin LL-37 and its smallest antimicrobial peptide KR-12 in lipid micelles. J Biol Chem 283:32637-32643.

Wright A. C., Simpson L. M., and Oliver J. D. 1981. Role of iron in the pathogenesis of *Vibrio vulnificus* infection. Infect. Immun 34: 503-507.

The invention claimed is:

1. An antimicrobial compound comprising a peptide comprising the amino acid sequence of
(SEQ ID NO: 20)
$X_1X_2X_3X_4X_5X_6RKKX_7KKLX_8KKLSPVIPLLX_9X_{10}X_{11}$
wherein $X_1$ is a non-polar amino acid or absent, $X_2$ is a basic amino acid or absent, $X_3$ is a non-polar amino acid or absent, $X_4$ is a basic amino acid or absent, $X_5$ is a basic amino acid or absent, $X_6$ is a non-polar amino acid, $X_7$ is a non-polar amino acid, $X_8$ is a non-polar amino acid, $X_9$ is a basic amino acid or absent, $X_{10}$ is a non-polar amino acid or absent, and $X_{11}$ is a non-polar amino acid or absent; or a pharmaceutically acceptable salt thereof,
wherein if $X_7$ is F, $X_6$ is not F.

2. The antimicrobial compound of claim 1, wherein the peptide comprises the amino acid sequence of
(SEQ ID NO: 24)
$X_1X_2X_3X_4X_5X_6RKKX_7KKLX_8KKLSPVIPLLX_9X_{10}X_{11}$
wherein
$X_1$ is G or absent, $X_2$ is R or absent, $X_3$ is F, A, or absent, $X_4$ is K or absent, $X_5$ is R or absent, $X_6$ is F or L, $X_7$ is F or L, $X_8$ is F or A, $X_9$ is H, K, or absent, $X_{10}$ is L or absent, and $X_{11}$ is G or absent, provided that when $X_7$ is F, $X_6$ is L; or a pharmaceutically salt thereof.

3. The antimicrobial compound of claim 1, wherein the peptide comprises the amino acid sequence of
(SEQ ID NO: 24)
$X_1X_2X_3X_4X_5X_6RKKX_7KKLX_8KKLSPVIPLLX_9X_{10}X_{11}$
wherein $X_7$ is F or L, provided that if $X_7$ is F, $X_6$ is not F; or a pharmaceutically salt thereof.

4. The antimicrobial compound of claim 1, wherein the peptide comprises a C-terminal substitution, an N-terminal substitution, or both a C-terminal substitution and an N-terminal substitution.

5. The antimicrobial compound of claim 4, wherein the peptide is N-terminally substituted to form RC(O)N(H)-peptide, wherein R is a —$OR^A$, —$NR^AR^B$, $C_{1-18}$ alkyl, or $C_{1-18}$ heteroalkyl, wherein each $R^A$ and $R^B$ is individually H, $C_{1-18}$ alkyl, or $C_{1-18}$ heteroalkyl, wherein each hydrogen atom on $C_{1-18}$ alkyl or $C_{1-18}$ heteroalkyl is optionally substituted with halo, hydroxy, or amino.

6. The antimicrobial compound of claim 4, wherein the peptide is C-terminally substituted to form (peptide)-C(O)R, wherein R is a —$OR^A$, —$NR^AR^B$, $C_{1-18}$ alkyl, or $C_{1-18}$ heteroalkyl, wherein each $R^A$ and $R^B$ is individually H, $C_{1-18}$ alkyl, $C_{1-18}$ heteroalkyl, or polyethylene glycol (PEG), wherein each hydrogen atom on $C_{1-18}$ alkyl or $C_{1-18}$ heteroalkyl is optionally substituted with halo, hydroxy, or amino, provided that when R is $OR^A$, $R^A$ is not H.

7. The antimicrobial compound of claim 1, wherein $X_7$ is L; or a pharmaceutically acceptable salt thereof.

8. The antimicrobial compound of claim 1, wherein the peptide comprises a sequence that is at least 90%, at least 93%, or at least 95% identical to a sequence selected from the group consisting of SEQ ID NO:11, SEQ ID NO:12, SEQ ID NO:13, SEQ ID NO:18, and SEQ ID NO:19; or a pharmaceutically acceptable salt thereof.

9. A method of treating a Gram-negative bacterial infection in a subject in need thereof, the method comprising administering to the subject an effective amount of an antimicrobial compound according to claim 1; or a pharmaceutically acceptable salt thereof.

10. The method of claim 9, wherein the subject is an animal from an aquaculture.

11. The method of claim 10, wherein the animal from an aquaculture is a fish or a shellfish.

12. The method of claim 9, wherein the subject is a mammal.

13. The method of claim 12, wherein the subject is a mouse or a human.

14. The method of claim 9, wherein the Gram-negative bacteria are a species in the *Vibrios* genus, an *Escherichia coli*, a *Klebsiella pneumoniae*, a *Pseudomonas aeruginosa*, or a mixture thereof.

15. The method of claim 9, wherein the Gram-negative bacteria are resistant to antibiotics.

16. The method of claim 15, wherein the Gram-negative bacteria are resistant to polymyxins.

17. The method of claim 15, wherein the Gram-negative bacteria are resistant to colistin.

18. An antimicrobial compound comprising a peptide comprising the amino acid sequence of $X_6RKKX_7KKLX_8KKLSPVIPLL$ (SEQ ID NO: 31)

wherein $X_6$ is a non-polar amino acid, $X_7$ is a non-polar amino acid, $X_8$ is a non-polar amino acid, provided that if $X_7$ is F, $X_6$ is not F, and wherein the N-terminus and the C-terminus of the amino acid sequence is optionally substituted.

19. The antimicrobial compound of claim 18, wherein the N-terminus, the C-terminus, or both the N-terminus and the C-terminus of the peptide is substituted.

20. The antimicrobial compound of claim 19, comprising a peptide selected from the group consisting of

FRKKLKKLFKKLSPVIPLLKLG-NH$_2$; (SEQ ID NO: 28)

FRKKLKKLAKKLSPVIPLLKLG-NH$_2$; (SEQ ID NO: 29)

ARKKLKKLAKKLSPVIPLLKLG-NH$_2$; (SEQ ID NO: 30)

Ac-FRKKLKKLFKKLSPVIPLLKLG-NH$_2$; (SEQ ID NO: 32)

Ac-FRKKLKKLFKKLSPVIPLLKLG-PEG; (SEQ ID NO: 33)
and

PEG-FRKKLKKLFKKLSPVIPLLKLG-NH$_2$; (SEQ ID NO: 34)

or a pharmaceutically acceptable salt thereof.

* * * * *

SEQUENCE LISTING

```
<160> NUMBER OF SEQ ID NOS: 34

<210> SEQ ID NO 1
<211> LENGTH: 37
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 1

Leu Leu Gly Asp Phe Phe Arg Lys Ser Lys Glu Lys Ile Gly Lys Glu
1               5                   10                  15

Phe Lys Arg Ile Val Gln Arg Ile Lys Asp Phe Leu Arg Asn Leu Val
            20                  25                  30

Pro Arg Thr Glu Ser
        35

<210> SEQ ID NO 2
<211> LENGTH: 37
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 2

Arg Leu Gly Asn Phe Phe Arg Lys Val Lys Glu Lys Ile Gly Gly Gly
1               5                   10                  15

Leu Lys Lys Val Gly Gln Lys Ile Lys Asp Phe Leu Gly Asn Leu Val
            20                  25                  30

Pro Arg Thr Ala Ser
        35

<210> SEQ ID NO 3
<211> LENGTH: 37
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 3

Gly Leu Arg Lys Arg Leu Arg Lys Phe Arg Asn Lys Ile Lys Glu Lys
1               5                   10                  15

Leu Lys Lys Ile Gly Gln Lys Ile Gln Gly Leu Leu Pro Lys Leu Ala
            20                  25                  30

Pro Arg Thr Asp Tyr
        35

<210> SEQ ID NO 4
<211> LENGTH: 34
<212> TYPE: PRT
<213> ORGANISM: Artificial Sequence
```

```
<220> FEATURE:
<223> OTHER INFORMATION: Description of Artificial Sequence: Synthetic
      polypeptide

<400> SEQUENCE: 4

Gly Leu Leu Arg Lys Gly Gly Glu Lys Ile Gly Glu Lys Leu Lys Lys
1               5                   10                  15

Ile Gly Gln Lys Ile Lys Asn Phe Phe Gln Lys Leu Val Pro Gln Pro
            20                  25                  30

Glu Gln

<210> SEQ ID NO 5
<211> LENGTH: 43
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 5

Gly Leu Arg Lys Lys Phe Arg Lys Thr Arg Lys Arg Ile Gln Lys Leu
1               5                   10                  15

Gly Arg Lys Ile Gly Lys Thr Gly Arg Lys Val Trp Lys Ala Trp Arg
            20                  25                  30

Glu Tyr Gly Gln Ile Pro Tyr Pro Cys Arg Ile
        35                  40

<210> SEQ ID NO 6
<211> LENGTH: 33
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 6

Gly Leu Phe Gly Arg Leu Arg Asp Ser Leu Gln Arg Gly Gly Gln Lys
1               5                   10                  15

Ile Leu Glu Lys Ala Glu Arg Ile Trp Cys Lys Ile Lys Asp Ile Phe
            20                  25                  30

Arg

<210> SEQ ID NO 7
<211> LENGTH: 34
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 7

Gly Leu Phe Arg Arg Leu Arg Asp Ser Ile Arg Arg Gly Gln Gln Lys
1               5                   10                  15

Ile Leu Glu Lys Ala Arg Arg Ile Gly Glu Arg Ile Lys Asp Ile Phe
            20                  25                  30

Arg Gly

<210> SEQ ID NO 8
<211> LENGTH: 37
<212> TYPE: PRT
<213> ORGANISM: Artificial Sequence
<220> FEATURE:
<223> OTHER INFORMATION: Description of Artificial Sequence: Synthetic
``` polypeptide

<400> SEQUENCE: 8

Gly Leu Leu Ser Arg Leu Arg Asp Phe Leu Ser Asp Arg Gly Arg
1               5                   10                  15

Leu Gly Glu Lys Ile Glu Arg Ile Gly Gln Lys Ile Lys Asp Leu Ser
            20                  25                  30

Glu Phe Phe Gln Ser
        35

<210> SEQ ID NO 9
<211> LENGTH: 40
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 9

Lys Arg Phe His Ser Val Gly Ser Leu Ile Gln Arg His Gln Gln Met
1               5                   10                  15

Ile Arg Asp Lys Ser Glu Ala Thr Arg His Gly Ile Arg Ile Ile Thr
            20                  25                  30

Arg Pro Lys Leu Leu Leu Ala Ser
        35                  40

<210> SEQ ID NO 10
<211> LENGTH: 27
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 10

Gly Arg Phe Lys Arg Phe Arg Lys Lys Phe Lys Lys Leu Phe Lys Lys
1               5                   10                  15

Leu Ser Pro Val Ile Pro Leu Leu His Leu Gly
            20                  25

<210> SEQ ID NO 11
<211> LENGTH: 27
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 11

Gly Arg Phe Lys Arg Leu Arg Lys Lys Phe Lys Lys Leu Phe Lys Lys
1               5                   10                  15

Leu Ser Pro Val Ile Pro Leu Leu His Leu Gly
            20                  25

<210> SEQ ID NO 12
<211> LENGTH: 27
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 12

Gly Arg Phe Lys Arg Leu Arg Lys Lys Leu Lys Lys Leu Phe Lys Lys

```
                1               5                   10                  15
Leu Ser Pro Val Ile Pro Leu Leu His Leu Gly
            20                  25

<210> SEQ ID NO 13
<211> LENGTH: 27
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 13

Gly Arg Ala Lys Arg Leu Arg Lys Leu Lys Lys Leu Ala Lys Lys
1               5                   10                  15

Leu Ser Pro Val Ile Pro Leu Leu His Leu Gly
            20                  25

<210> SEQ ID NO 14
<211> LENGTH: 29
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 14

Arg Gly Leu Arg Arg Leu Gly Arg Lys Ile Ala His Gly Val Lys Lys
1               5                   10                  15

Tyr Gly Pro Thr Val Leu Arg Ile Ile Arg Ile Ala Gly
            20                  25

<210> SEQ ID NO 15
<211> LENGTH: 29
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 15

Arg Gly Leu Arg Arg Leu Gly Arg Lys Ile Ala His Gly Val Lys Lys
1               5                   10                  15

Cys Gly Pro Thr Val Leu Arg Ile Ile Arg Ile Ala Gly
            20                  25

<210> SEQ ID NO 16
<211> LENGTH: 30
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 16

Arg Gly Leu Arg Arg Leu Gly Arg Lys Ile Ala His Gly Val Lys Lys
1               5                   10                  15

Cys Gly Pro Thr Val Leu Arg Ile Ile Arg Ile Ala Gly Cys
            20                  25                  30

<210> SEQ ID NO 17
<211> LENGTH: 29
<212> TYPE: PRT
<213> ORGANISM: Artificial Sequence
<220> FEATURE:
```

<223> OTHER INFORMATION: Description of Artificial Sequence: Synthetic
      peptide

<400> SEQUENCE: 17

Arg Gly Leu Arg Arg Leu Gly Arg Lys Ile Ala His Gly Val Lys Lys
1               5                   10                  15

Leu Gly Pro Thr Val Leu Arg Ile Ile Arg Ile Ala Gly
            20                  25

<210> SEQ ID NO 18
<211> LENGTH: 24
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 18

Gly Arg Phe Lys Arg Phe Arg Lys Lys Leu Lys Lys Leu Phe Lys Lys
1               5                   10                  15

Leu Ser Pro Val Ile Pro Leu Leu
            20

<210> SEQ ID NO 19
<211> LENGTH: 22
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 19

Phe Arg Lys Lys Leu Lys Lys Leu Phe Lys Lys Leu Ser Pro Val Ile
1               5                   10                  15

Pro Leu Leu Lys Leu Gly
            20

<210> SEQ ID NO 20
<211> LENGTH: 27
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: Any non-polar amino acid or absent
<220> FEATURE:
<221> NAME/KEY: MOD_RES
<222> LOCATION: (2)..(2)
<223> OTHER INFORMATION: Any basic amino acid or absent
<220> FEATURE:
<221> NAME/KEY: MOD_RES
<222> LOCATION: (3)..(3)
<223> OTHER INFORMATION: Any non-polar amino acid or absent
<220> FEATURE:
<221> NAME/KEY: MOD_RES
<222> LOCATION: (4)..(4)
<223> OTHER INFORMATION: Any basic amino acid or absent
<220> FEATURE:
<221> NAME/KEY: MOD_RES
<222> LOCATION: (5)..(5)
<223> OTHER INFORMATION: Any basic amino acid or absent
<220> FEATURE:
<221> NAME/KEY: MOD_RES
<222> LOCATION: (6)..(6)
<223> OTHER INFORMATION: Any non-polar amino acid
<220> FEATURE:
<221> NAME/KEY: MOD_RES

```
<222> LOCATION: (10)..(10)
<223> OTHER INFORMATION: Any non-polar amino acid
<220> FEATURE:
<221> NAME/KEY: MOD_RES
<222> LOCATION: (14)..(14)
<223> OTHER INFORMATION: Any non-polar amino acid
<220> FEATURE:
<221> NAME/KEY: MOD_RES
<222> LOCATION: (25)..(25)
<223> OTHER INFORMATION: Any basic amino acid or absent
<220> FEATURE:
<221> NAME/KEY: MOD_RES
<222> LOCATION: (26)..(26)
<223> OTHER INFORMATION: Any non-polar amino acid or absent
<220> FEATURE:
<221> NAME/KEY: MOD_RES
<222> LOCATION: (27)..(27)
<223> OTHER INFORMATION: Any non-polar amino acid or absent

<400> SEQUENCE: 20

Xaa Xaa Xaa Xaa Xaa Xaa Arg Lys Lys Xaa Lys Lys Leu Xaa Lys Lys
1               5                   10                  15

Leu Ser Pro Val Ile Pro Leu Leu Xaa Xaa Xaa
            20                  25

<210> SEQ ID NO 21
<211> LENGTH: 30
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (17)..(17)
<223> OTHER INFORMATION: Any polar amino acid or non-polar amino acid
<220> FEATURE:
<221> NAME/KEY: MOD_RES
<222> LOCATION: (30)..(30)
<223> OTHER INFORMATION: Any polar amino acid or absent

<400> SEQUENCE: 21

Arg Gly Leu Arg Arg Leu Gly Arg Lys Ile Ala His Gly Val Lys Lys
1               5                   10                  15

Xaa Gly Pro Thr Val Leu Arg Ile Ile Arg Ile Ala Gly Xaa
            20                  25                  30

<210> SEQ ID NO 22
<211> LENGTH: 22
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: Any non-polar amino acid
<220> FEATURE:
<221> NAME/KEY: MOD_RES
<222> LOCATION: (5)..(5)
<223> OTHER INFORMATION: Any non-polar amino acid
<220> FEATURE:
<221> NAME/KEY: MOD_RES
<222> LOCATION: (9)..(9)
<223> OTHER INFORMATION: Any non-polar amino acid
<220> FEATURE:
<221> NAME/KEY: MOD_RES
<222> LOCATION: (20)..(20)
<223> OTHER INFORMATION: Any basic amino acid
<220> FEATURE:
<221> NAME/KEY: MOD_RES
<222> LOCATION: (21)..(21)
```

<223> OTHER INFORMATION: Any non-polar amino acid
<220> FEATURE:
<221> NAME/KEY: MOD_RES
<222> LOCATION: (22)..(22)
<223> OTHER INFORMATION: Any non-polar amino acid

<400> SEQUENCE: 22

Xaa Arg Lys Lys Xaa Lys Lys Leu Xaa Lys Lys Leu Ser Pro Val Ile
1               5                   10                  15

Pro Leu Leu Xaa Xaa Xaa
            20

<210> SEQ ID NO 23
<211> LENGTH: 24
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: Any non-polar amino acid
<220> FEATURE:
<221> NAME/KEY: MOD_RES
<222> LOCATION: (2)..(2)
<223> OTHER INFORMATION: Any basic amino acid
<220> FEATURE:
<221> NAME/KEY: MOD_RES
<222> LOCATION: (3)..(3)
<223> OTHER INFORMATION: Any non-polar amino acid
<220> FEATURE:
<221> NAME/KEY: MOD_RES
<222> LOCATION: (4)..(4)
<223> OTHER INFORMATION: Any basic amino acid
<220> FEATURE:
<221> NAME/KEY: MOD_RES
<222> LOCATION: (5)..(5)
<223> OTHER INFORMATION: Any basic amino acid
<220> FEATURE:
<221> NAME/KEY: MOD_RES
<222> LOCATION: (6)..(6)
<223> OTHER INFORMATION: Any non-polar amino acid
<220> FEATURE:
<221> NAME/KEY: MOD_RES
<222> LOCATION: (10)..(10)
<223> OTHER INFORMATION: Any non-polar amino acid
<220> FEATURE:
<221> NAME/KEY: MOD_RES
<222> LOCATION: (14)..(14)
<223> OTHER INFORMATION: Any non-polar amino acid

<400> SEQUENCE: 23

Xaa Xaa Xaa Xaa Xaa Xaa Arg Lys Lys Xaa Lys Lys Leu Xaa Lys Lys
1               5                   10                  15

Leu Ser Pro Val Ile Pro Leu Leu
            20

<210> SEQ ID NO 24
<211> LENGTH: 27
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MISC_FEATURE
<222> LOCATION: (1)..(1)
<223> OTHER INFORMATION: May or may not be present
<220> FEATURE:
<221> NAME/KEY: MISC_FEATURE
<222> LOCATION: (2)..(2)
<223> OTHER INFORMATION: May or may not be present

```
<220> FEATURE:
<221> NAME/KEY: MOD_RES
<222> LOCATION: (3)..(3)
<223> OTHER INFORMATION: Phe, Ala or absent
<220> FEATURE:
<221> NAME/KEY: MISC_FEATURE
<222> LOCATION: (4)..(4)
<223> OTHER INFORMATION: May or may not be present
<220> FEATURE:
<221> NAME/KEY: MISC_FEATURE
<222> LOCATION: (5)..(5)
<223> OTHER INFORMATION: May or may not be present
<220> FEATURE:
<221> NAME/KEY: MOD_RES
<222> LOCATION: (6)..(6)
<223> OTHER INFORMATION: Phe or Leu
<220> FEATURE:
<221> NAME/KEY: MOD_RES
<222> LOCATION: (10)..(10)
<223> OTHER INFORMATION: Phe or Leu
<220> FEATURE:
<221> NAME/KEY: MOD_RES
<222> LOCATION: (14)..(14)
<223> OTHER INFORMATION: Phe or Ala
<220> FEATURE:
<221> NAME/KEY: MOD_RES
<222> LOCATION: (25)..(25)
<223> OTHER INFORMATION: His, Lys or absent
<220> FEATURE:
<221> NAME/KEY: MISC_FEATURE
<222> LOCATION: (26)..(26)
<223> OTHER INFORMATION: May or may not be present
<220> FEATURE:
<221> NAME/KEY: MISC_FEATURE
<222> LOCATION: (27)..(27)
<223> OTHER INFORMATION: May or may not be present

<400> SEQUENCE: 24

Gly Arg Xaa Lys Arg Xaa Arg Lys Lys Xaa Lys Lys Leu Xaa Lys Lys
1               5                   10                  15

Leu Ser Pro Val Ile Pro Leu Leu Xaa Leu Gly
            20                  25

<210> SEQ ID NO 25
<211> LENGTH: 22
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: Phe or Leu
<220> FEATURE:
<221> NAME/KEY: MOD_RES
<222> LOCATION: (5)..(5)
<223> OTHER INFORMATION: Phe or Leu
<220> FEATURE:
<221> NAME/KEY: MOD_RES
<222> LOCATION: (9)..(9)
<223> OTHER INFORMATION: Phe or Ala
<220> FEATURE:
<221> NAME/KEY: MOD_RES
<222> LOCATION: (20)..(20)
<223> OTHER INFORMATION: His or Lys

<400> SEQUENCE: 25

Xaa Arg Lys Lys Xaa Lys Lys Leu Xaa Lys Lys Leu Ser Pro Val Ile
1               5                   10                  15

Pro Leu Leu Xaa Leu Gly
            20
```

```
<210> SEQ ID NO 26
<211> LENGTH: 24
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (3)..(3)
<223> OTHER INFORMATION: Phe or Ala
<220> FEATURE:
<221> NAME/KEY: MOD_RES
<222> LOCATION: (6)..(6)
<223> OTHER INFORMATION: Phe or Leu
<220> FEATURE:
<221> NAME/KEY: MOD_RES
<222> LOCATION: (10)..(10)
<223> OTHER INFORMATION: Phe or Leu
<220> FEATURE:
<221> NAME/KEY: MOD_RES
<222> LOCATION: (14)..(14)
<223> OTHER INFORMATION: Phe or Ala

<400> SEQUENCE: 26

Gly Arg Xaa Lys Arg Xaa Arg Lys Lys Xaa Lys Lys Leu Xaa Lys Lys
1               5                   10                  15

Leu Ser Pro Val Ile Pro Leu Leu
            20

<210> SEQ ID NO 27
<211> LENGTH: 30
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (17)..(17)
<223> OTHER INFORMATION: Tyr, Cys or Leu
<220> FEATURE:
<221> NAME/KEY: MISC_FEATURE
<222> LOCATION: (30)..(30)
<223> OTHER INFORMATION: May or may not be present

<400> SEQUENCE: 27

Arg Gly Leu Arg Arg Leu Gly Arg Lys Ile Ala His Gly Val Lys Lys
1               5                   10                  15

Xaa Gly Pro Thr Val Leu Arg Ile Ile Arg Ile Ala Gly Cys
            20                  25                  30

<210> SEQ ID NO 28
<211> LENGTH: 22
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 28

Phe Arg Lys Lys Leu Lys Lys Leu Phe Lys Lys Leu Ser Pro Val Ile
1               5                   10                  15

Pro Leu Leu Lys Leu Gly
            20

<210> SEQ ID NO 29
<211> LENGTH: 22
<212> TYPE: PRT
<213> ORGANISM: Artificial Sequence
```

```
<220> FEATURE:
<223> OTHER INFORMATION: Description of Artificial Sequence: Synthetic
      peptide

<400> SEQUENCE: 29

Phe Arg Lys Lys Leu Lys Lys Leu Ala Lys Lys Leu Ser Pro Val Ile
1               5                   10                  15

Pro Leu Leu Lys Leu Gly
            20

<210> SEQ ID NO 30
<211> LENGTH: 22
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 30

Ala Arg Lys Lys Leu Lys Lys Leu Ala Lys Lys Leu Ser Pro Val Ile
1               5                   10                  15

Pro Leu Leu Lys Leu Gly
            20

<210> SEQ ID NO 31
<211> LENGTH: 19
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: Any non-polar amino acid
<220> FEATURE:
<221> NAME/KEY: MOD_RES
<222> LOCATION: (5)..(5)
<223> OTHER INFORMATION: Any non-polar amino acid
<220> FEATURE:
<221> NAME/KEY: MOD_RES
<222> LOCATION: (9)..(9)
<223> OTHER INFORMATION: Any non-polar amino acid

<400> SEQUENCE: 31

Xaa Arg Lys Lys Xaa Lys Lys Leu Xaa Lys Lys Leu Ser Pro Val Ile
1               5                   10                  15

Pro Leu Leu

<210> SEQ ID NO 32
<211> LENGTH: 22
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 32

Phe Arg Lys Lys Leu Lys Lys Leu Phe Lys Lys Leu Ser Pro Val Ile
1               5                   10                  15

Pro Leu Leu Lys Leu Gly
            20

<210> SEQ ID NO 33
<211> LENGTH: 22
<212> TYPE: PRT
<213> ORGANISM: Artificial Sequence
```

```
<220> FEATURE:
<223> OTHER INFORMATION: Description of Artificial Sequence: Synthetic
      peptide

<400> SEQUENCE: 33

Phe Arg Lys Lys Leu Lys Lys Leu Phe Lys Lys Leu Ser Pro Val Ile
1               5                   10                  15

Pro Leu Leu Lys Leu Gly
            20

<210> SEQ ID NO 34
<211> LENGTH: 22
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 34

Phe Arg Lys Lys Leu Lys Lys Leu Phe Lys Lys Leu Ser Pro Val Ile
1               5                   10                  15

Pro Leu Leu Lys Leu Gly
            20
```